(12) United States Patent
Lamphere et al.

(10) Patent No.: US 8,070,802 B2
(45) Date of Patent: Dec. 6, 2011

(54) MITRAL VALVE SYSTEM

(75) Inventors: David G. Lamphere, Framingham, MA (US); Tuan Anh Nguyen, Woburn, MA (US); Howard C. Herrmann, Bryn Mawr, PA (US); Todd C. Tomba, Columbus, OH (US); Robert C. Gorman, Lower Gwynedd, PA (US); Joseph H. Gorman, III, Lower Gwynedd, PA (US)

(73) Assignees: The Trustees of the University of Pennsylvania, Philadelphia, PA (US); EndoValve, Inc., Princeton, NJ (US)

( * ) Notice: Subject to any disclaimer, the term of this patent is extended or adjusted under 35 U.S.C. 154(b) by 827 days.

(21) Appl. No.: 12/028,572

(22) Filed: Feb. 8, 2008

(65) Prior Publication Data
US 2008/0221672 A1    Sep. 11, 2008

Related U.S. Application Data

(63) Continuation-in-part of application No. 11/869,972, filed on Oct. 10, 2007, now Pat. No. 7,753,949.

(60) Provisional application No. 60/902,988, filed on Feb. 23, 2007.

(51) Int. Cl.
*A61F 2/24*    (2006.01)
*A61F 2/06*    (2006.01)

(52) U.S. Cl. ...................... 623/2.14; 623/1.26

(58) Field of Classification Search .................. 623/1.15, 623/1.36, 1.24, 1.26, 2.14, 2.18, 2.1, 2.12
See application file for complete search history.

(56) References Cited

U.S. PATENT DOCUMENTS
4,454,875 A    6/1984    Pratt et al.
(Continued)

FOREIGN PATENT DOCUMENTS
EP    1281375    2/2003
(Continued)

OTHER PUBLICATIONS

Davies, H., "Catheter-Mounted Valve for Temporary Relief of Aortic Insufficiency," The Lancet, Jan. 30, 1965.
(Continued)

*Primary Examiner* — Alvin J Stewart
(74) *Attorney, Agent, or Firm* — McCarter & English, LLP

(57) ABSTRACT

Valve prostheses are disclosed that are adapted for secure and aligned placement relative to a heart annulus. The valve prostheses may be placed in a non-invasive manner, e.g., via transcatheter techniques. The valve prosthesis may include a resilient ring, a plurality of leaflet membranes mounted with respect to the resilient ring, and a plurality of positioning elements movably mounted with respect to the flexible ring. Each of the positioning elements defines respective proximal, intermediate, and distal tissue engaging regions cooperatively configured and dimensioned to simultaneously engage separate corresponding areas of the tissue of an anatomical structure, including respective first, second, and third elongate tissue-piercing elements. The proximal, distal, and intermediate tissue-engaging regions are cooperatively configured and dimensioned to simultaneously engage separate corresponding areas of the tissue of an anatomical structure so as to stabilize a position of the valve prosthesis with respect to the anatomical structure, including wherein for purposes of so simultaneously engaging the separate corresponding areas of tissue, at least one of the first, second, and third elongate tissue-piercing elements is pointed at least partially opposite the direction of blood flow, and at least another thereof is pointed at least partially along the direction of blood flow. The valve prosthesis may also include a skirt mounted with respect to the resilient ring for sealing a periphery of the valve prosthesis against a reverse flow of blood around the valve prosthesis.

16 Claims, 33 Drawing Sheets

U.S. PATENT DOCUMENTS

| | | | |
|---|---|---|---|
| 4,759,759 A | 7/1988 | Walker et al. | |
| 5,554,185 A | 9/1996 | Block et al. | |
| 5,855,601 A | 1/1999 | Bessler et al. | |
| 6,287,339 B1 | 9/2001 | Vazquez et al. | |
| 6,425,916 B1 | 7/2002 | Garrison et al. | |
| 6,458,153 B1 | 10/2002 | Bailey et al. | |
| 6,551,344 B2 | 4/2003 | Thill | |
| 6,605,102 B1 | 8/2003 | Mazzocchi et al. | |
| 6,676,698 B2* | 1/2004 | McGuckin et al. | 623/1.24 |
| 6,682,559 B2 | 1/2004 | Myers et al. | |
| 6,736,845 B2 | 5/2004 | Marquez | |
| 6,790,229 B1 | 9/2004 | Berreklouw | |
| 6,846,325 B2 | 1/2005 | Liddicoat | |
| 6,893,459 B1 | 5/2005 | Macoviak | |
| 6,896,690 B1 | 5/2005 | Lambrecht | |
| 7,041,128 B2* | 5/2006 | McGuckin et al. | 623/1.36 |
| 7,097,659 B2 | 8/2006 | Woolfson et al. | |
| 7,201,772 B2* | 4/2007 | Schwammenthal et al. | 623/2.18 |
| 7,311,730 B2* | 12/2007 | Gabbay | 623/2.38 |
| 7,320,704 B2 | 1/2008 | Lashinski et al. | |
| 7,524,332 B2* | 4/2009 | Osborne et al. | 623/2.14 |
| 7,566,343 B2* | 7/2009 | Jenson et al. | 623/2.12 |
| 7,604,661 B2* | 10/2009 | Pavcnik et al. | 623/1.24 |
| 7,799,069 B2* | 9/2010 | Bailey et al. | 623/1.26 |
| 7,799,072 B2* | 9/2010 | Greenberg | 623/2.14 |
| 7,871,434 B2* | 1/2011 | Case et al. | 623/2.12 |
| 7,947,075 B2* | 5/2011 | Goetz et al. | 623/2.18 |
| 2001/0002445 A1 | 5/2001 | Vesely | |
| 2001/0021872 A1* | 9/2001 | Bailey et al. | 623/1.24 |
| 2001/0039450 A1* | 11/2001 | Pavcnik et al. | 623/1.24 |
| 2002/0055772 A1* | 5/2002 | McGuckin et al. | 623/1.24 |
| 2002/0055774 A1 | 5/2002 | Liddicoat | |
| 2002/0133226 A1 | 9/2002 | Marquez et al. | |
| 2002/0138138 A1 | 9/2002 | Yang et al. | |
| 2003/0036791 A1 | 2/2003 | Philip et al. | |
| 2003/0125805 A1 | 7/2003 | Johnson et al. | |
| 2003/0149477 A1* | 8/2003 | Gabbay | 623/2.14 |
| 2004/0024451 A1 | 2/2004 | Johnson et al. | |
| 2004/0044406 A1 | 3/2004 | Woolfson et al. | |
| 2004/0092858 A1 | 5/2004 | Wilson | |
| 2004/0097979 A1 | 5/2004 | Svanidze | |
| 2004/0122516 A1 | 6/2004 | Fogarty et al. | |
| 2004/0127981 A1 | 7/2004 | Rahdert | |
| 2004/0127982 A1 | 7/2004 | Machold | |
| 2004/0138745 A1 | 7/2004 | Macoviak | |
| 2004/0186558 A1* | 9/2004 | Pavcnik et al. | 623/1.24 |
| 2004/0186563 A1 | 9/2004 | Lobbi | |
| 2004/0210304 A1 | 10/2004 | Seguin | |
| 2004/0225353 A1 | 11/2004 | McGuckin, Jr. | |
| 2004/0243222 A1* | 12/2004 | Osborne et al. | 623/1.24 |
| 2004/0260393 A1 | 12/2004 | Rahdert | |
| 2005/0010287 A1 | 1/2005 | Macoviak et al. | |
| 2005/0033398 A1 | 2/2005 | Seguin | |
| 2005/0043760 A1 | 2/2005 | Fogarty et al. | |
| 2005/0055089 A1 | 3/2005 | Macoviak | |
| 2005/0070993 A1* | 3/2005 | Boekstegers et al. | 623/1.25 |
| 2005/0075584 A1 | 4/2005 | Cali | |
| 2005/0137681 A1* | 6/2005 | Shoemaker et al. | 623/1.23 |
| 2005/0137697 A1 | 6/2005 | Salahieh et al. | |
| 2005/0182486 A1 | 8/2005 | Gabbay | |
| 2005/0216079 A1 | 9/2005 | Macoviak | |
| 2005/0261759 A1 | 11/2005 | Lambrecht | |
| 2005/0267573 A9 | 12/2005 | Macoviak et al. | |
| 2006/0015179 A1 | 1/2006 | Bulman-Fleming et al. | |
| 2006/0020327 A1 | 1/2006 | Lashinski et al. | |
| 2006/0020332 A1 | 1/2006 | Lashinski et al. | |
| 2006/0020333 A1 | 1/2006 | Lashinski et al. | |
| 2006/0020334 A1 | 1/2006 | Lashinski et al. | |
| 2006/0025854 A1 | 2/2006 | Lashinski et al. | |
| 2006/0025855 A1 | 2/2006 | Lashinski et al. | |
| 2006/0089671 A1 | 4/2006 | Goldfarb et al. | |
| 2006/0161249 A1 | 7/2006 | Realyvasquez et al. | |
| 2006/0190074 A1* | 8/2006 | Hill et al. | 623/1.23 |
| 2006/0212110 A1* | 9/2006 | Osborne et al. | 623/1.24 |
| 2006/0212111 A1* | 9/2006 | Case et al. | 623/1.24 |
| 2006/0229708 A1* | 10/2006 | Powell et al. | 623/1.24 |
| 2006/0253188 A1* | 11/2006 | Case | 623/1.24 |
| 2006/0253191 A1 | 11/2006 | Salahieh et al. | |
| 2006/0271081 A1 | 11/2006 | Realyvasquez | |
| 2006/0276882 A1* | 12/2006 | Case et al. | 623/1.24 |
| 2006/0293759 A1* | 12/2006 | Berg et al. | 623/23.7 |
| 2007/0010877 A1 | 1/2007 | Salahieh et al. | |
| 2007/0016286 A1* | 1/2007 | Herrmann et al. | 623/2.11 |
| 2007/0027518 A1* | 2/2007 | Case et al. | 623/1.1 |
| 2007/0106372 A1* | 5/2007 | Osborne et al. | 623/1.24 |
| 2008/0015687 A1 | 1/2008 | Lashinski et al. | |
| 2008/0046071 A1* | 2/2008 | Pavcnik | 623/1.24 |
| 2008/0133003 A1* | 6/2008 | Seguin et al. | 623/2.11 |
| 2008/0208328 A1 | 8/2008 | Antocci et al. | |
| 2008/0208332 A1 | 8/2008 | Lamphere et al. | |
| 2008/0275550 A1* | 11/2008 | Kheradvar et al. | 623/2.14 |
| 2009/0216313 A1* | 8/2009 | Straubinger et al. | 623/1.17 |
| 2009/0254174 A1* | 10/2009 | Case et al. | 623/1.17 |
| 2009/0270972 A1* | 10/2009 | Lane | 623/1.14 |
| 2009/0287298 A1* | 11/2009 | Jenson et al. | 623/1.24 |
| 2010/0016953 A1* | 1/2010 | Sisken et al. | 623/1.36 |
| 2010/0057191 A1* | 3/2010 | Pavcnik et al. | 623/1.24 |
| 2010/0222871 A1* | 9/2010 | Pollock et al. | 623/1.36 |
| 2010/0249923 A1* | 9/2010 | Alkhatib et al. | 623/2.18 |
| 2010/0312330 A1* | 12/2010 | Majercak et al. | 623/1.36 |
| 2011/0029067 A1* | 2/2011 | McGuckin et al. | 623/1.24 |

FOREIGN PATENT DOCUMENTS

| | | |
|---|---|---|
| WO | WO 98/10719 | 3/1998 |
| WO | WO 00/44311 | 8/2000 |
| WO | WO 03/088873 | 10/2003 |
| WO | WO 2004/043293 | 1/2004 |
| WO | WO 2004/019811 | 3/2004 |
| WO | WO 2004/028558 | 4/2004 |
| WO | WO 2004/030568 | 4/2004 |
| WO | WO 2004/030569 | 4/2004 |
| WO | WO 2004/030570 | 4/2004 |
| WO | WO 2005/112827 | 1/2005 |
| WO | WO 2005/009285 | 2/2005 |
| WO | WO 2005/046528 | 5/2005 |

OTHER PUBLICATIONS

Bonhoeffer, et al., "Precutaneous Insertion of the Pulmonary Valve," J. of the Am. College of Cardiology, 2002, 39(10), 1664-1669.

Cribier, et al., "Precutaneous Transcatheter implantation of an Aortic Valve Prostheses for Calcific Aortic Stenosis," Circulation, 2002, 3006-3008.

Block, P.C., "Precutaneous Mitral Valve Repair for Mitral Regurgitation," J. of Interventional Cardiology, 2003, 16(1) 93-96.

PCT International Search Report dated Feb. 9, 2005.

PCT International Search Report dated Aug. 8, 2008 (PCT/US08/50096).

PCT International Search Report dated Aug. 8, 2008 (PCT/US08/54410).

PCT International Search Report dated Aug. 12, 2008.

European Search Report dated Mar. 28, 2007.

* cited by examiner

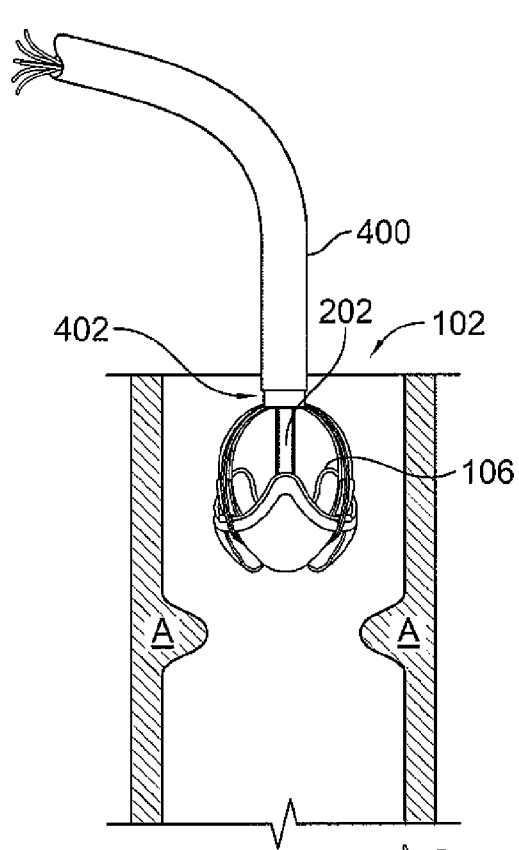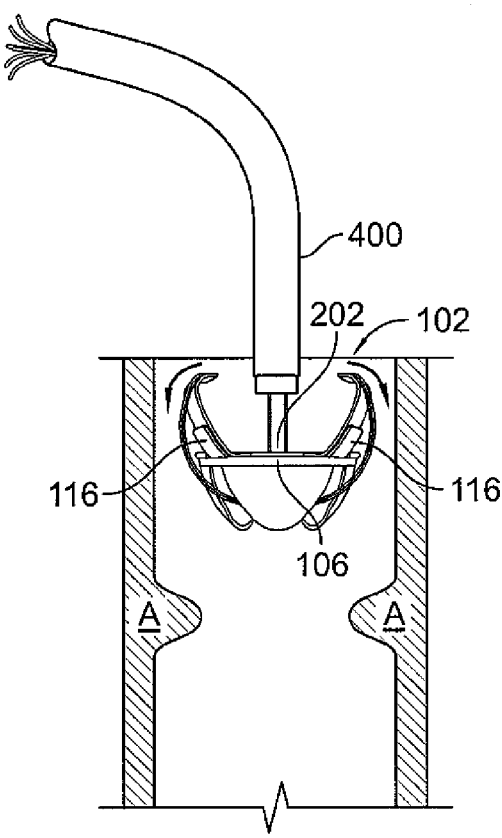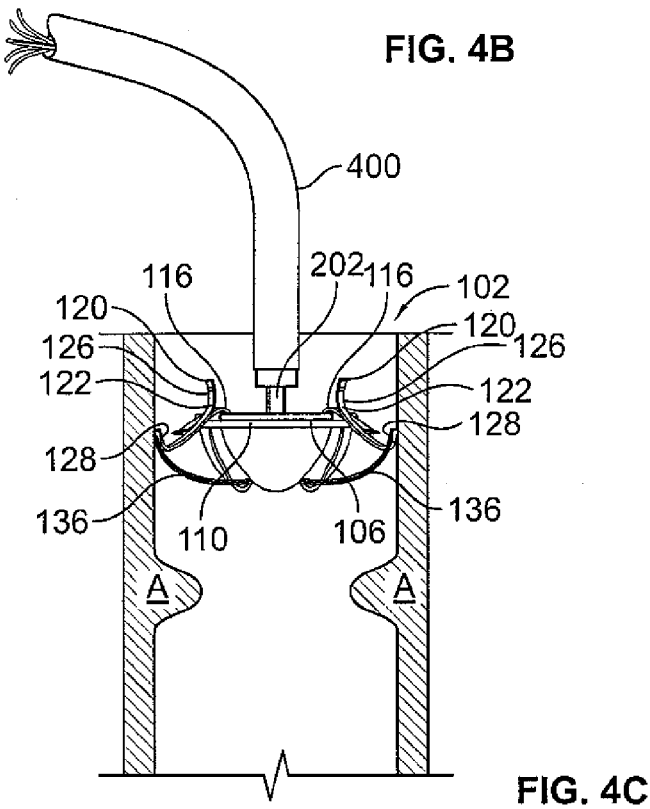

MITRAL VALVE SYSTEM

CROSS-REFERENCE TO RELATED APPLICATIONS

The present application claims the benefit of provisional patent application entitled "Valve Prosthesis System" that was filed on Feb. 23, 2007 and assigned Ser. No. 60/902,988. The present application also claims the benefit of a non-provisional patent application entitled Valve Prosthesis Systems and Methods" that was filed on Oct. 10, 2007 and assigned Ser. No. 11/869,972. The entire contents of the foregoing provisional and non-provisional applications are incorporated herein by reference.

BACKGROUND

1. Technical Field

The present disclosure is directed to advantageous valve prosthesis systems and associated methods/systems for placement of a heart valve prosthesis and, more particularly, to a mitral valve prosthesis that is adapted for secure and aligned placement relative to a heart annulus and associated methods/systems for placement thereof.

2. Background Art

Heart valve regurgitation occurs when the heart valve does not close completely as a result of disease or injury. Mitral regurgitation due to ischemic and degenerative (prolapse) disease has been shown to contribute to left ventricular dilation and dysfunction due to remodeling, and is associated with increased rates of cardiac events and death. Currently, malfunctioning heart valves may be replaced with biologic or mechanical prostheses through open-heart surgery with the attendant significant risk of death, stroke, infection, bleeding, and complications due to the use of general anesthesia and cardiopulmonary bypass.

Based on the success of percutaneous balloon valvuplasty for mitral stenosis, investigators have explored other alternative methods to treat valvular heart disease without surgery. For example, Cribier et al. describe a balloon-expandable stent to which a biologic valve prosthesis is sewn. (See, "Percutaneous Transcatheter Implantation of an Aortic Valve Prosthesis for Calcific Aortic Stenosis," Circulation, Dec. 10, 2002, pages 3006-3008.) The Cribier device is utilized to treat calcific aortic stenosis. Bonhoeffer et al. describe a similar stent approach with a bovine venous (jugular) valve inserted to treat pulmonic valve disease. (See, "Percutaneous Insertion of the Pulmonary Valve," Journal of the American College of Cardiology, Vol. 39, No. 10, May 15, 2002, pages 1664-1669.) Others are developing repair techniques for mitral valve disease that involve placing a clip on the mitral leaflets (U.S. Pat. No. 6,629,534), cinching the mitral annulus from the coronary sinus (U.S. Pat. No. 6,537,314), or deploying an inflatable heart valve that is mechanically held in place (U.S. Pat. No. 5,554,185).

Norred (U.S. Pat. No. 6,482,228) discloses a percutaneous aortic valve replacement in which a heart valve prosthesis having ribs and a circular elastomeric canopy is folded for insertion into a catheter for delivery to the implantation region without surgery. Once in the ascending aorta, the body and leaflets of the heart valve prosthesis are opened like an umbrella by pulling on a central column of suture-like members. Hinge joints are used to create a miniature umbrella. However, the aortic valve prosthesis is anchored using a stent system that is extended in the ascending aorta to anchor the valve in the aortic channel above the biologic aortic valve. The suture-like members used to open the umbrella structure are deployed as part of the stent system. Such a design is not amenable to placement of the heart valve prosthesis at the location of the biologic valve.

Other stented heart valve prostheses are described in the art in which the anchoring system is a passive one that requires either balloon expandable stents or a self-expanding stent design. For example, such stented designs are described in U.S. Pat. No. 6,454,799, US 2002/0138138, U.S. Pat. Nos. 6,582,462, 6,458,153, 6,425,916, and 5,855,601. It will be appreciated that once these stented heart valve prostheses are deployed, they cannot be repositioned, refolded, or easily removed. Furthermore, the rigidity of the stent as it is deployed in calcified positions may allow for regurgitation around the outside of the stent, as has been seen in the early aortic valve deployments which utilize this design. It is also difficult to position these designs as one has to inflate a balloon in a moving column of blood while the heart is beating and one only gets one chance to accurately deploy it.

An additional difficulty occurs when deploying a stented heart valve in an annulus that is not thickened by calcium. The stent design lends itself slightly better to the aortic position where the height of the annulus has been increased and the width thickened by the presence of calcium in calcific aortic stenosis. However, when calcium is not present, as in other causes of aortic valve disease and in the mitral position, the stent may be difficult to anchor on the relatively thin annulus. Furthermore, the nature by which the stent folds on a balloon and then expands with plastic deformability limits the ratio of its initial to final size such that it will, by necessity, have a fairly large profile making percutaneous insertion via catheter more difficult in a valve annulus with a large diameter that has not been reduced by calcium deposition.

Herrmann et al. (US 2007/0016286) disclose a percutaneously inserted bistable heart valve prosthesis that may be folded inside a catheter for delivery to the patient's heart for implantation. The heart valve has an elastic annular ring, a body member having a plurality of legs, each leg connecting at one end to the annular ring, claws that are adjustable from a first position to a second position by application of external force so as to allow ingress of surrounding heart tissue into the claws in the second position, and leaflet membranes connected to the annular ring, the body member and/or the legs. The disclosed leaflet membranes have a first position for blocking blood flow therethrough and a second position for allowing blood flow therethrough. The heart valve is designed such that upon removal of the external force, the claws elastically revert to the first position so as to grip the heart tissue positioned within the claws, thereby holding the heart valve in place. The body member and claws may be integrated into a one-piece design. The heart valve so designed may be used as a prosthesis for the mitral valve, aortic valve, pulmonary valve, or tricuspid valve by adapting the annular ring to fit in a respective mitral, aortic, pulmonary, or tricuspid valve opening of the heart.

Machold et al. (US 2004/0127982) disclose an implant that is sized and configured to attach to the annulus of a dysfunctional heart valve. In use, the implant extends across the major axis of the annulus above and/or along the valve annulus. The implant reshapes the major axis dimension and/or other surrounding anatomic structures and is intended to restore a more functional anatomic shape and tension. Machold et al. contemplate a pair of struts that are joined by a rail and that carry other structures to enhance the anchorage and stabilization of the implant in the heart valve annulus. The anchoring mechanisms may be located below the plane of the annulus to engage infra-annular heart tissue adjoining the annulus in the ventricle and/or may be located at or above the plane of the annulus, to engage tissue on the annulus or in the atrium. Machold et al. further disclose that the struts may be used to simply locate the implant in the valve, imparting little or no force on their own. In this arrangement, the annulus reshaping forces of the Machold design emanate from the rail(s) above the commissures.

Under image guidance, the Machold et al. strut on the leading end of the implant is freed from a sheath and seated retrograde in the posterior commissure of the valve annulus. Anchoring structures or mechanisms associated with the strut are also placed into contact with adjoining tissue below and/ or above the plane of the annulus. As shown in FIG. 25B, the delivery catheter maintains force on the leading strut within the posterior commissure as the sheath is withdrawn in line with the coaptation line in a posterior-to-anterior direction along the coaptation line. Similar structures for positioning an implant relative to an annulus are disclosed by Vazquez et al. (U.S. Pat. No. 6,287,339).

Despite efforts to date, a need remains for an improved heart valve prosthesis design that allows a low profile for insertion via a catheter but, in the absence of a balloon or stent, transforms to a large profile once deployed. A heart valve prosthesis design is also desired that can be deployed, folded, removed, and then redeployed so as to increase the safety as well as the preciseness of prosthesis deployment. Still further, a need remains for heart valve prosthesis design(s) that may be effectively aligned and/or oriented relative to the heart and, most desirably, is substantially self-aligning and/or self-orienting with respect thereto. Reliable and effective deployment systems and methods for such advantageous heart valve prostheses are also needed.

These and other needs are addressed by the disclosed prosthesis designs and deployment systems/methodologies, as will be apparent from the detailed description which follows.

SUMMARY

Advantageous valve prosthesis systems and methods/systems for placement of valve prostheses are disclosed herein. In exemplary embodiments of the present disclosure, a mitral valve prosthesis is provided that is adapted for secure and aligned placement relative to a heart annulus. The disclosed valve prosthesis systems may be placed in a minimally-invasive manner, e.g., via trans-catheter techniques.

An exemplary valve prosthesis includes a resilient ring, a plurality of leaflet membranes mounted with respect to the resilient ring, and a plurality of positioning elements movably mounted with respect to the flexible ring. Each of the positioning elements defines a proximal tissue engaging region including a first elongate tissue-piercing element, a distal tissue engaging region spaced apart from the proximal tissue engaging region along a direction of blood flow through the valve prosthesis and including a second elongate tissue-piercing element, and an intermediate tissue engaging region disposed between the proximal and distal tissue engaging region and including a third elongate tissue-piercing element. The proximal, distal, and intermediate tissue-engaging regions are cooperatively configured and dimensioned to simultaneously engage separate corresponding areas of the tissue of an anatomical structure so as to stabilize a position of the valve prosthesis with respect to the anatomical structure, including wherein for purposes of so simultaneously engaging the separate corresponding areas of tissue, at least one of the first, second, and third elongate tissue-piercing elements is pointed at least partially opposite the direction of blood flow, and at least another thereof is pointed at least partially along the direction of blood flow.

At least one of the first and second elongate tissue-engaging elements may include a fork tine. For example, at least one of the first and second elongate tissue-engaging elements may include a fork defining a pair of closely-spaced, outwardly-extending fork times for cooperatively piercing, connecting, and/or anchoring the valve prosthesis with respect to a particular area of native valve tissue (e.g., such as a valve annulus or one or more valve leaflets), the fork tines being joined by a transversely extending web region for engaging a portion of the native valve tissue area falling between the tines so as to limit a depth to which the latter may become lodged in the former. For another example, at least one of the proximal and distal tissue engaging regions may further define an arcuate surface for engaging the corresponding area of tissue so as to limit a depth to which the respective first or second elongate tissue-piercing element may become lodged therewithin. The third elongate tissue-piercing element may include a chevron-shaped barb.

For purposes of so simultaneously engaging the separate corresponding areas of tissue: 1) the first elongate tissue-piercing element may be pointed at least partially opposite the direction of blood flow, and the third elongate tissue-piercing element may be pointed at least partially along the direction of blood flow, 2) the second elongate tissue-piercing element may be pointed at least partially opposite the direction of blood flow, and the third elongate tissue-piercing element may be pointed at least partially along the direction of blood flow, and/or 3) two of the first, second, and third elongate tissue-piercing elements may be pointed at least partially opposite the direction of blood flow, and the other thereof may be pointed at least partially along the direction of blood flow.

Each of the plurality of positioning elements may be adapted to substantially completely invert by rotating relative to the resilient ring between a first position in which the at least two of the first, second, and third elongate tissue-piercing elements point at least partially along the direction of blood flow for facilitating positioning of the valve prosthesis within a delivery catheter, and a second position in which the at least two of the first, second, and third elongate tissue-piercing elements point at least partially opposite the direction of blood flow for engaging tissue.

The resilient ring may include multiple instances of a hoop segment defining a hoop plane and separated by a corresponding number of instances of a gap within the hoop plane, and/or may include multiple instances of a hoop segment defining a hoop plane for coupling with a separate respective one of the plurality of leaflet membranes and a corresponding number of instances of a retainer for forming separate respective interfaces between respective adjacent ones of the plurality of leaflet membranes. The resilient ring may define a circular or elliptical peripheral geometry.

The valve prosthesis may further include a hub disposed substantially centrally with respect to a peripheral geometry of the resilient ring, and a plurality of legs directed radially with respect to the resilient ring and mounted with respect to (i) the hub and (ii) a corresponding positioning element of the plurality thereof. The leg may be mounted with respect to the positioning element such that the positioning element is substantially rotationally fixed with respect to the leg. The leg may include an intermediate joint and corresponding leg lengths extending from the joint for allowing the leg to collapse against itself for facilitating positioning of the valve prosthesis within a delivery catheter.

Each positioning element of the plurality may include a pair of apertures for permitting the positioning element to be releasably engaged by a corresponding filament looped through the apertures of the pair thereof for remotely controlling a rotational position of the positioning element during implantation of the valve prosthesis. The resilient ring may be adapted to be implanted with respect to a diseased heart valve such that the first tissue-piercing element lodges within tissue associated with an annulus of the diseased heart valve, and the second tissue-piercing element lodges within tissue associated with a leaflet of the diseased heart valve.

The valve prosthesis may further include a skirt mounted with respect to the resilient ring for at least partially sealing against a reverse flow of blood around a periphery of the valve prosthesis.

Additional advantageous features, structures and functions associated with the disclosed valve prosthesis will be apparent from the description of exemplary embodiments which follows, particularly when read in conjunction with the accompanying figures.

BRIEF DESCRIPTION OF THE FIGURES

To assist those of ordinary skill in the art in making and using the disclosed valve prosthesis system and associated deployment systems/methods, reference is made to the accompanying figures wherein:

FIGS. 4A, 4B, 4C, 4D, 4E, 4F, 4G, 4H, and 4I are schematic views illustrating percutaneous placement of a heart valve prosthesis relative to an annulus according to an exemplary embodiment of the present disclosure;

DESCRIPTION OF EXEMPLARY EMBODIMENT(S)

Advantageous valve prosthesis systems and deployment systems/methods are provided according to the present disclosure. The disclosed systems and methods permit surgeons/clinicians to improve heart valve function without invasive surgical intervention. Indeed, the disclosed valve prosthesis systems permit a heart valve prosthesis to be percutaneously delivered to a desired anatomical location. Once located in the desired anatomical region/locale, the disclosed valve prosthesis system facilitates secure and aligned placement of a heart valve prosthesis relative to a heart annulus. Percutaneous delivery of the disclosed heart valve prosthesis as disclosed herein provides for efficient and effective clinical placement of a heart valve prosthesis. The disclosed heart valve prosthesis and associated delivery techniques offer numerous clinical benefits, including enhanced valve function without the need to remove existing valve leaflets, an ability to effectively and efficiently deliver a valve prosthesis percutaneously, and an ability to position a valve prosthesis relative to an annulus to ensure proper orientation relative to anatomical features.

Figure 1:
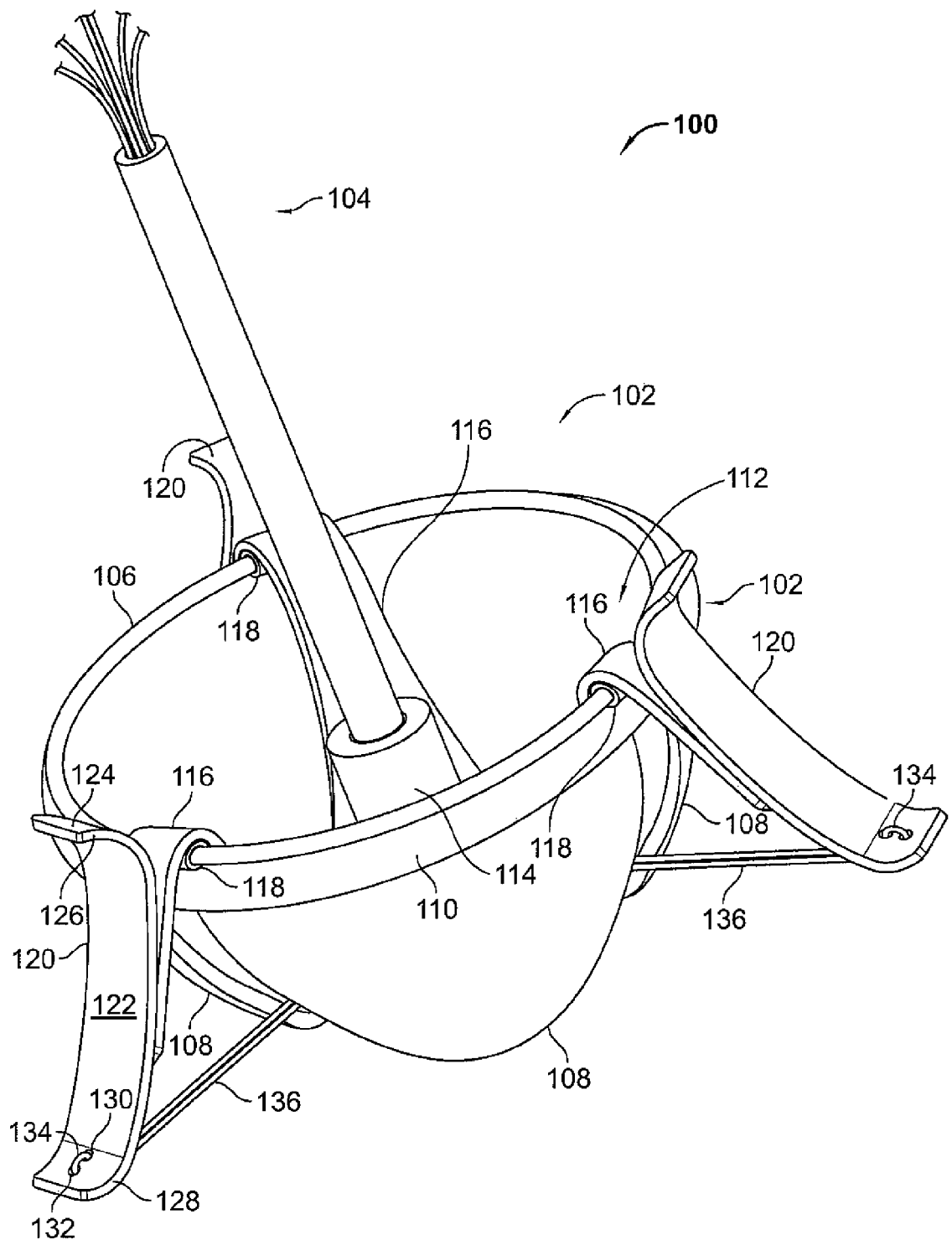
FIG. 1 is a downward perspective of an exemplary valve prosthesis system according to the present disclosure.

With initial reference to FIG. 1, an exemplary valve prosthesis system 100 is schematically depicted. The valve prosthesis system 100 includes a heart valve prosthesis 102 and a delivery structure 104. The valve prosthesis 102 includes a flexible ring 106. Mounted with respect to the flexible ring 106 are a plurality of leaflet membranes 108, a valve skirt 110, and a resilient element 112. The resilient element 112 may include a hub 114 and a plurality of legs 116, each of the legs 116 extending from the hub 114 (e.g., in a regular radial arrangement, as shown in FIG. 1) and being movably mounted with respect to the flexible ring 106 via individual ones of a corresponding plurality of mounting elements 118. The valve prosthesis 102 may further include a corresponding plurality of positioning elements 120, each such positioning element 120 being attached to one of the legs 116 of the resilient element 112.

As shown in the exemplary embodiment of FIG. 1, the valve prosthesis 102 may include three (3) leaflet membranes 108, each leaflet membrane 108 assuming an inwardly bowed orientation when mounted with respect to the flexible ring 106. More or fewer of the leaflet membranes 108 may be employed without departing from the spirit or scope of the present disclosure, provided the desired blood flow functionality is achieved. The leaflet membranes 108 may be fabricated from xenograft tissue, e.g., the valve leaflets may be fabricated from standard biologic or artificial prosthetic material, such as cryo- or chemically-preserved bovine pericardium or porcine heart valve tissue. Synthetic membrane materials may also be employed in the fabrication of the leaflet membranes 108, e.g., fiber-reinforced matrix materials. The leaflet membranes 108 may be secured with respect to the flexible ring 106 through conventional means, e.g., creation of an annulus and/or cuff that surrounds, in whole or in part, the flexible ring 106 such that each of the plurality of leaflet membranes 108 extends downwardly with respect to the flexible ring 106.

With further reference to FIG. 1, the valve skirt 110 may extend to a full extent of the flexible ring 106, e.g., to a fill extent of the circumference of the flexible ring 106. The valve skirt 110 may be formed from a single, contiguous structure, or may be defined by a plurality of adjacent and/or overlapping elements that, together, extend along the circumference of flexible ring 106. According to exemplary embodiments of the present disclosure, the valve skirt 110 may be sutured with respect to the flexible ring 106. Alternatively, a cuff may be formed at an edge of the valve skirt 110, such cuff being adapted to receive the flexible ring 106 therewithin. The cuff may extend along the entire edge of the valve skirt 110 or may be defined at discrete intervals along the length of the valve skirt 110, such that the valve skirt 110 is mounted with respect to the flexible ring 106 at spaced intervals. The valve skirt 110 may be fabricated from a variety of substantially flexible and/or pliable materials, e.g., xenographic tissue or a synthetic material that is compatible with blood flow, e.g., a non-thrombogenic material. Indeed, in an exemplary embodiment of the present disclosure, the valve skirt 110 and the leaflet membranes 108 may be fabricated as integral/contiguous structures, e.g., from a desired xenographic and/or synthetic material, and such integral/continuous structure may be advantageously mounted with respect to the flexible ring 106 such that the functionalities of both elements (i.e., leaflet membrane functionality and valve skirt functionality) are achieved.

The thickness of the valve skirt 110 may be substantially uniform from edge-to-edge or may vary along its length. For example, in an exemplary embodiment of the present disclosure, it is contemplated that the valve skirt 110 would be thicker in a region thereof adjacent the flexible ring 106 and thinner in a region thereof relatively more distant from the flexible ring 106, thereby enhancing the flexibility of the valve skirt 110 in the latter region to provide more effective sealing functionality relative to adjacent anatomical structures/tissue. The thicker region adjacent the flexible ring 106 may serve to reduce the likelihood of the valve skirt 110 disengaging from the flexible ring 106.

Although the exemplary embodiment of FIG. 1 depicts the valve skirt 110 extending in a single direction relative to the flexible ring 106, i.e., downward, it is contemplated according to the present disclosure that the valve skirt 110 may extend both upwardly and downwardly relative to the flexible ring 106. In some such implementation of the valve skirt 110, the attachment means for securing the valve skirt 110 relative to the flexible ring 106 would not necessarily be located at an edge thereof. Rather, such attachment means, e.g., cuff(s) and/or suturing, may be positioned along an intermediate line/region of the valve skirt 110. In this way, a first portion of the valve skirt 110 would be free to extend above the flexible ring 106, and a second portion of the valve skirt 110 would be free to extend below the flexible ring 106. Both portions of the valve skirt 110, i.e., the portions above and below the flexible ring 106, would advantageously function to seal the valve prosthesis 102 relative to a patient's anatomy when the valve prosthesis 102 is deployed relative thereto, as described in greater detail below. Of note, a portion of the valve skirt 110 extending above the flexible ring 106 may include a notch or discontinuity to accommodate structures associated with the positioning elements 120, as described in greater detail below. The valve skirt 110 may have a downward length that is effective to achieve a desired level of sealing relative to surrounding anatomical structures. For Example, the valve skirt 110 may have a downward length of about five (5) millimeters to about fifteen (15) millimeters relative to the flexible ring 106. Similar dimensions are contemplated for the upward extending portion of the valve skirt 110 in implementations wherein the valve skirt 110 extends both above and below the flexible ring 106.

For greater security/stability, the valve skirt 110 may be tacked or otherwise secured in at least some manner relative to the resilient element 112 (e.g., to one or more of the legs 116 of the resilient element 112). In an alternative embodiment, the valve skirt 110 may be positioned radially outward of the positioning elements 120.

As shown in FIG. 1, the resilient element 112 may include three (3) legs 116 mounted in a circumferentially-spaced manner with respect to the flexible ring 106 via the mounting elements 118. Each leg 116 may be configured or adapted to include or assume an arcuate shape or bend in the vicinity of the flexible ring 106. The legs 116 may be spaced by about 120° relative to each other, although an alternative number and/or spacing of the legs 116 may be employed without departing from the spirit or scope of the present disclosure. The mounting elements 118 may be of any suitable shape, design, configuration, and/or attachment technique relative to the legs 116 to permit rotational and/or overturning motion of the legs 116 relative to the hub 114, and/or relative to the flexible ring 106. For example, the mounting elements 118 may be substantially C-shaped, and/or tube shaped. The mounting elements 118 may, for example, be affixed to respective undersides of the legs 116 (e.g., within an arcuate or bent portion thereof) through an appropriate mounting technique, e.g., a tack weld.

Returning to the potential interplay between the legs 116 of the resilient element 114 and the valve skirt 110, the mounting elements 118 may overlay the valve skirt 110 to the extent that the valve skirt 110 is secured to the flexible ring 106 in such circumferential region. Further, the valve skirt 110 may be tacked, adhered or otherwise joined to the underside of one or more of the legs 116 where the same extend over the valve skirt 110.

With further reference to FIG. 1, each of the positioning elements 120 may be shaped, configured, and/or otherwise adapted to engage tissue, and/or to position the valve prosthesis 102 relative to tissue. For example, each positioning element 120 may define an outer surface 122, an inner surface 124 opposite the outer surface 122, an upper arcuate region 126, and a lower arcuate region 128 opposite the upper arcuate region 126. Each of the positioning elements 120 may be coupled (e.g., fixedly joined) to a corresponding leg 116 of the resilient element 112, e.g., through a weld between the inner surface 124 of the positioning element 120 a corresponding outer surface of the leg 116. The positioning elements 120 may be dimensioned such that the upper arcuate regions 126 thereof extend above the flexible ring 106 (e.g., when the valve prosthesis 102 assumes the orientation depicted in FIG. 1). The upper and lower arcuate regions 126, 128 of the positioning elements 120 may be spaced by a distance that facilitates positioning of the valve prosthesis 102 relative to a heart annulus, as described in greater detail below. For example, the upper and lower arcuate regions 126, 128 may be spaced by between about seven (7) millimeters and about twenty-five (25) millimeters. The positioning elements 120 and the legs 116 may be fabricated from a material that permits at least some degree of flexibility/deformation (e.g., elastic deformation), such as stainless steel or Nitinol of an appropriate thickness/gauge. Other materials for the positioning elements 120 and/or the legs 116 are possible.

The lower arcuate regions 128 of the positioning elements 120 may include a pair of spaced apertures 130, 132. The delivery structure 104 may include a plurality of filaments or cords 134, each cord 134 being threaded through a positioning element 120 via the pair of spaced apertures 130, 132 formed therein, such that separate lengths 136 of the cord 134 extend away from the apertures 130, 132 and radially inwardly toward the hub 114 of the resilient element 112. As may be more clearly seen in FIG. 2, the hub 114 of the resilient element 112 may include one or more lumen(s) 200 (e.g., a centrally-located lumen 200), the delivery structure 104 may include a delivery tube 202 having one or more corresponding lumens 204 (e.g., an axially located lumen), and the lengths 136 of the cords 134 may pass from the respective lower arcuate regions 128 of the positioning elements 120 toward the hub 114, into and through the lumen 200 thereof, and into and through the lumen 204 of the delivery tube 202. Such lengths 136 of the cords 134, and/or such routing of such lengths 136 of such cords 134 from the lower arcuate regions 128 of the positioning elements 120 and via the hub 114 and/or the delivery tube 202, may facilitate deployment of the valve prosthesis 102 relative to an annulus and/or associated heart tissue.

The delivery tube 202 may be flexible, and the lumen or lumens 204 may accommodate passage of a plurality of lengths 136 of cords 134. In the exemplary embodiment of FIGS. 1 and 2, three (3) positioning elements 120 are associated with the valve prosthesis 102 and each positioning element 120 interacts with a separate cord 134. Thus, the respective lumen(s) 200, 204 of the hub 114 and the delivery tube 200 may be appropriately sized and/or of an appropriate number to accommodate least six (6) separate lengths 136 of cords 134, based on the looping of each cord 134 through a pair of spaced apertures 130, 132 formed at or near the respective lower arcuate regions 128 of the positioning elements 120.

Figure 2:
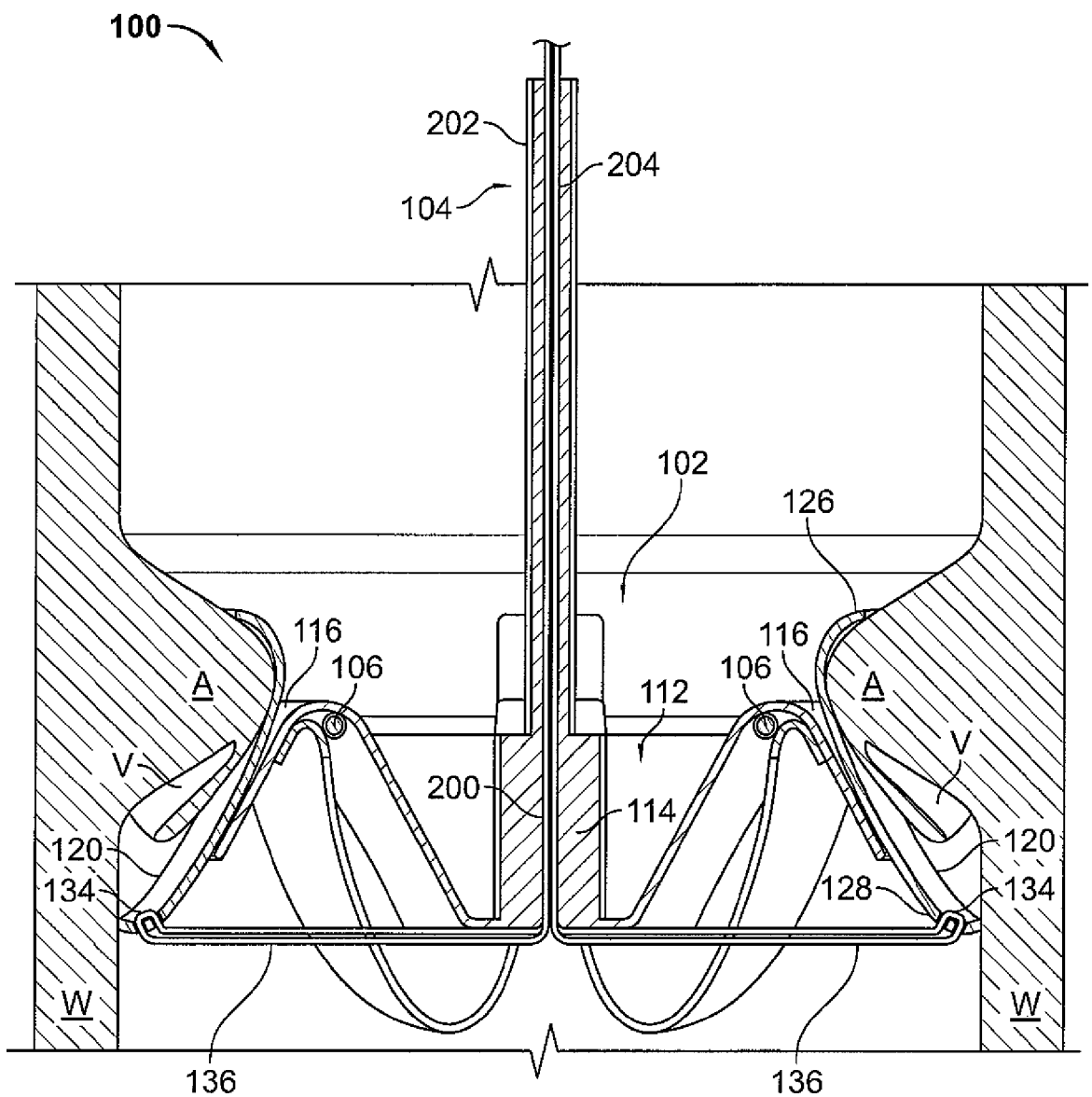
FIG. 2 is a partially-sectional side view of an exemplary valve prosthesis system according to the present disclosure positioned relative to a heart annulus.

As is also apparent from the cross-sectional view of FIG. 2, the legs 116 of the resilient element 112 may cooperate with the hub 114 thereof and/or with the flexible ring 106 to provide stability to the valve prosthesis 102, e.g., during the deployment process, and/or during the useful life of the valve prosthesis 102 in situ. The structural interaction between the legs 116 and the flexible ring 106, and/or between the legs 116 and the hub 114, permits a surgeon/clinician to utilize the lengths 136 of the cords 134 and the delivery structure 104 to remotely operate the valve prosthesis 102 (e.g., to remotely move/rotate the legs 116 relative to the flexible ring 106 and/or relative to the hub 114). Each of the legs 116 may, for example, include one or more joints along its respective length (e.g., one or more living hinges at or near a mid-point thereof) to facilitate collapse of valve prosthesis 102 for catheter-based delivery thereof. In embodiments in accordance with the present disclosure, one or more such joints may store energy so as to facilitate the delivery of a spring force to expand the flexible ring 106 to a full diameter thereof (or at least a substantial fraction thereof), or assist in an otherwise substantially self-powered expansion thereof, upon deployment of the valve prosthesis 102 in situ. In embodiments in accordance with the present disclosure, one or more such joints may further store energy so as to urge the positioning elements 120 radially outward (e.g., toward secure engagement with corresponding tissue, and/or radially outward from a compressed shape associated with intra-catheter delivery). According to at least some exemplary embodiments of the present disclosure, three (3) legs 116 may extend from the hub 114, such that the resilient element 112 assumes a 'tripod'-type shape for expanding and/or supporting the valve prosthesis 102 (e.g., helping the flexible ring 106 to assume and/or maintain a shape consistent with the intended function of the valve prosthesis 102, and/or to urge the positioning elements 120 radially outward) during deployment and/or while implanted in situ.

With further reference to FIG. 2, the valve prosthesis 102 of the valve prosthesis system 100 is depicted in alignment and engagement with an heart valve annulus "A" and a heart wall "W" of a patient. The valve prosthesis 102 is further shown displacing heart valve leaflet structure "V" (e.g., the valve prosthesis 102 is implanted within the annulus A for purposes of providing the valve function for which the valve leaflet structure V is no longer well suited). The annulus A is depicted in an enlarged and symmetric fashion for ease of description. The actual geometric and dimensional details of the relevant anatomical structures are well known to persons skilled in the art. As shown in FIG. 2, each of the upper arcuate regions 126 of the respective positioning elements 120 may be positioned advantageously so as to engage a corresponding part of an upper portion of the annulus A. In this fashion, at least, the positioning elements 120 may be employed in cooperation with each other to align the valve prosthesis 102 relative to the annulus A. As also shown in FIG. 2, each of the lower arcuate regions 128 may be positioned advantageously so as to engage a corresponding part of the wall W below the annulus A. In this fashion, at least, the positioning elements 120 may be employed in cooperation with each other to stabilize and secure the valve prosthesis 102 relative to the overall anatomical environment.

In the event the surgeon/clinician is or becomes dissatisfied with the position/orientation of valve prosthesis 102 relative to the annulus A or the wall W, or has or develops some other concern or uncertainty with respect to the deployment of the valve prosthesis 102, he/she may deflect the lower arcuate regions 128 of the positioning elements 120 inward by pulling or otherwise manipulating or moving the respective lengths 136 of the cords 134 a sufficient extent radially inwardly and/or upwardly through the hub 114 and the delivery tube 202 to cause the lower arcuate regions 128 of the positioning elements 120 to disengage from the wall W. The surgeon/clinician may then reposition the structure of the valve prosthesis 102 relative to the overall anatomical environment by pulling, pushing, or otherwise manipulating or moving the delivery tube 202 to a desired extent with respect to the delivery catheter (not separately shown). Such manipulation may, for example, be translated to the valve prosthesis 102 via the hub 114 and the legs 116 of the resilient element 112. In accordance with embodiments of the present disclosure, after delivering the valve prosthesis 102 to the position with respect to the annulus A shown in FIG. 2, the surgeon/clinician may elect to pull the valve prosthesis 102 at least partially back upward, causing the lower arcuate regions 128 of the positioning elements to engage a corresponding part of a lower portion of the annulus A, and/or to engage the heart valve leaflet structure V, which in at least some instances results in the valve prosthesis 102 to be lodged and/or anchored in a particularly secure fashion within the annulus A.

Once satisfied with the position of the valve prosthesis 102 relative to the annulus A and/or the wall W, the surgeon/clinician may withdraw the cords 134 from the valve prosthesis 102 through the delivery tube 202 by pulling outward on one length 136 thereof to a sufficient extent while leaving the other length 136 loose. The surgeon/clinician may further withdraw the remainder of the delivery structure 104 from the valve prosthesis 102 by separating the delivery tube 202 from the hub 114 of the resilient element 112. Means for disconnecting the delivery tube 202 from the hub 114 may take a variety of forms, e.g., a screw thread arrangement at the end of the delivery tube 202 that may be disengaged from a corresponding socket associated with the hub 114. Still further (e.g., alternative) connection and/or disconnection means are possible, including bayonet lock mechanisms, detent engagement mechanisms, and the like, at least some of which are further described hereinbelow.

Tissue-engaging features, e.g., barbs, tacks or the like, may be formed on, in, and/or through one or more tissue-engaging surfaces of the respective positioning elements 120. For example, such features may be formed on the outer surface 122 of the positioning elements 120, e.g., within the upper and/or lower arcuate regions 126, 128. Additionally, surface treatments and/or adjunct structures may be associated with the positioning elements 120 to promote tissue in-growth, thereby further enhancing the stability/security of an implanted valve prosthesis according to the present disclosure. For example, a biologic coating and/or a material or fabric that promotes tissue in-growth, e.g., DACRON™ material, may be applied to a desired portion/region of the respective outer surfaces 122 of the positioning elements 120.

The disclosed valve prostheses and valve prosthesis systems and methods have applicability in a variety of anatomical regions, e.g., as a prosthesis for the mitral valve, aortic valve, pulmonary valve, or tricuspid valve. Embodiments of the disclosed valve prosthesis have particular applicability for mitral valve applications. Depending on the desired clinical application, the valve prosthesis system 100 and/or the valve prosthesis 102 may be sized and dimensioned to accommodate such use by adapting the annular ring to fit in the requisite anatomical space, e.g., a mitral, aortic, pulmonary, or tricuspid valve opening of the heart.

Figures 3A, 3B:
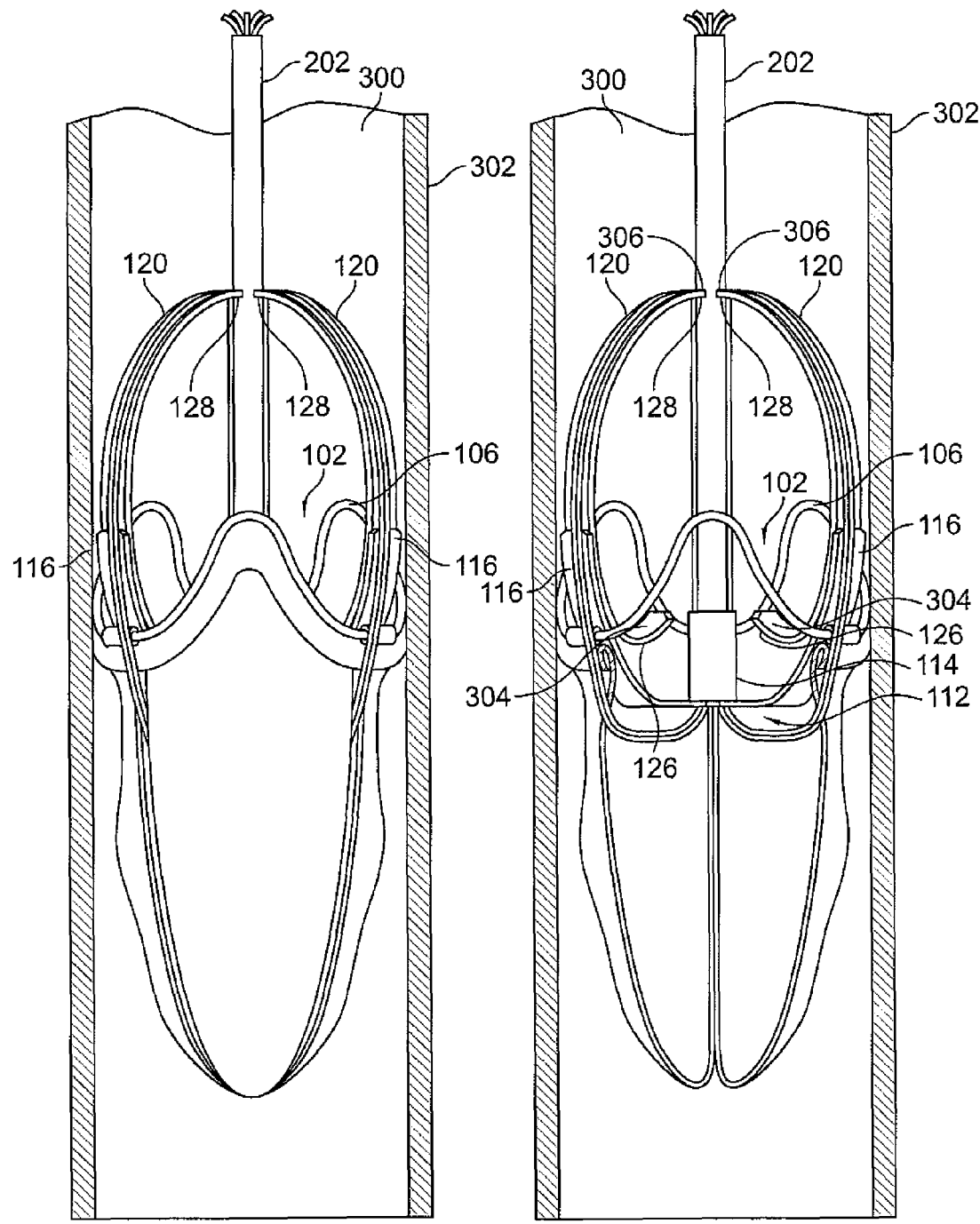
FIG. 3A is a side view of an exemplary prosthesis system according to the present disclosure, wherein an exemplary heart valve prosthesis is positioned within an exemplary delivery structure.
FIG. 3B is a partially-sectional side view of the exemplary prosthesis system of FIG. 3A, also shown positioned within the exemplary delivery structure.

Turning to FIGS. 3A and 3B, the heart valve prosthesis 102 may assume a collapsed configuration within a lumen 300 of a catheter 302. Additionally, the positioning elements 120 may be substantially inverted, e.g., rotated approximately 180° relative to the flexible ring 106 to which they are mounted and relative to the hub 114 of the resilient element 112, as compared to the relative positions or orientations the positioning elements 120 may tend to occupy with respect to such structure (e.g., as shown in FIG. 1) when not being subjected to the application of opposing outside forces. The flexible ring 106 may also be substantially deformed and the legs 116 of the resilient element 112 may be deflected so as to permit the valve prosthesis 102 to fit within the catheter 302. In this inverted orientation, the upper and lower arcuate regions 126, 128 associated with the respective positioning elements 120 may be inwardly directed toward the delivery tube 202. In an exemplary embodiment of the present disclosure, the upper and lower arcuate portions 126, 128 of the respective positioning elements 120 may be associated with and/or terminate in respective tips 304, 306, and such tips 304, 306 may feature cut-outs (not shown in FIGS. 3A and 3B), e.g., arcuate notches, such cut-outs being adapted to cooperate with a substantially cylindrical geometry of the delivery tube 202 when the positioning elements 120 are in the substantially inverted orientations depicted in FIGS. 3A and 3B.

Figure 4D:
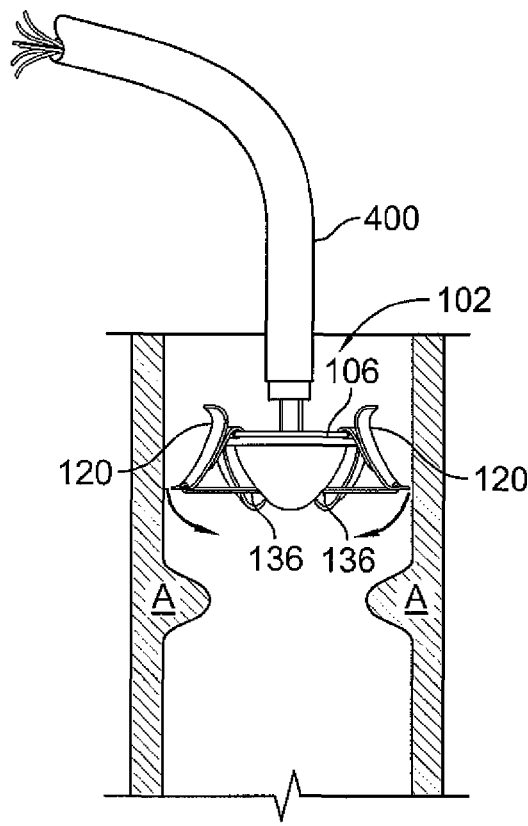

Turning to FIGS. 4A-4I, an exemplary sequence of steps for percutaneously delivering and positioning the disclosed valve prosthesis 102 in a desired anatomical location are schematically depicted. As shown in FIGS. 4A-4C, the valve prosthesis 102 may be navigated to the desired anatomical location, e.g., adjacent a mitral valve, aortic valve, pulmonary valve, or tricuspid valve, within a delivery catheter 400 having a distal end 402. In accordance with embodiments of the present disclosure, the valve prosthesis 102 may be delivered to the mitral valve cavity transseptally or by direct venous or arterial delivery to the aortic valve, pulmonary valve, or tricuspid valve cavities. In exemplary embodiments, the valve prosthesis may be navigated to a desired location using a guide wire (not shown) that cooperates with a corresponding guide wire lumen (not shown) formed in or otherwise present within the delivery catheter 400. The valve prosthesis 102 may be advanced through the delivery catheter 400 along an associated guide wire in a collapsed/inverted orientation (by being pushed, for example, by the delivery tube 202) to the implantation position (e.g., left atrium for mitral valve) where the valve prosthesis 102 is deployed adjacent the diseased valve for subsequent implantation therein. Alternatively, the valve prosthesis 102 may be pre-positioned within the delivery catheter 400 at or near the distal end 402, and both the valve prosthesis 102 and the distal end 402 of the delivery catheter 400 may be so advanced in unison along an associated guide wire.

Once a distal end 402 of the delivery catheter 400 has been delivered to within the necessary proximity of the desired anatomical location, e.g., annulus "A", the delivery tube 202 may be extended relative to the delivery catheter 400 to push the valve prosthesis 102 outward of the catheter 400 via a corresponding opening in the distal end 402. Upon the valve prosthesis 102 exiting the distal end 402, resilient properties of several components of the valve prosthesis 102, particularly the flexible ring 106 and the legs 116 of the resilient element 112 (FIG. 2), may cause at least the flexible ring 106 to automatically resume its non-deformed/uncompressed shape (e.g., as seen in FIG. 4B as well as all later figures in the sequence of FIGS. 4A-4I), which may be, for example, a circle, an ellipse, or the like. As best seen in FIG. 4C, upon the surgeon/clinician allowing the valve prosthesis 102 to emerge from the delivery catheter 400, yet without any her positive action on the part of the surgeon/clinician, the valve prosthesis 102 may tend eventually to fully relax, and assume a generally non-deformed orientation, wherein the positioning elements 120 are seen to have overturned or become inverted by rotating both outwardly and downwardly past the horizontal (e.g., so that the outer surfaces 122 thereof face generally outward again, and the upper and lower arcuate regions 126, 128 thereof are, once again, outwardly directed). The valve skirt 110 may be appropriately substantially downwardly oriented and positioned for performing an advantageous sealing function (e.g., as against valve prolapse) upon being positioned in a desired anatomical position.

Figure 4E:
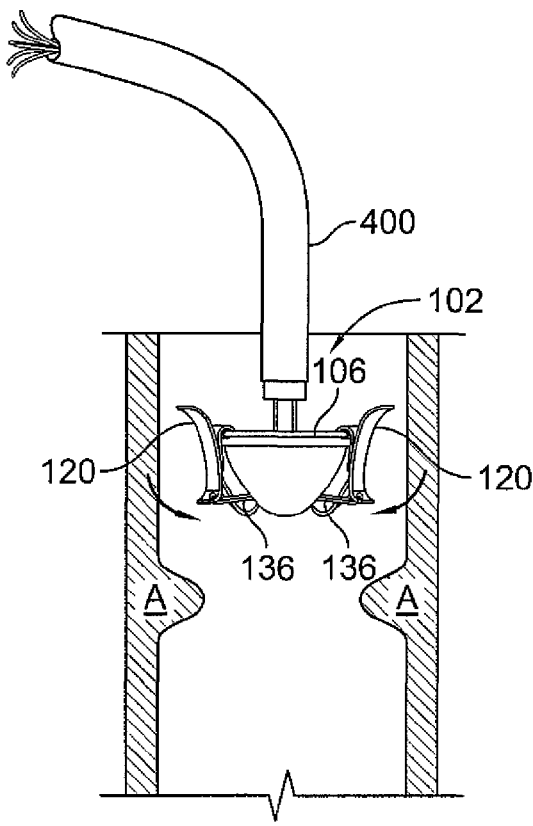
Figure 4F:
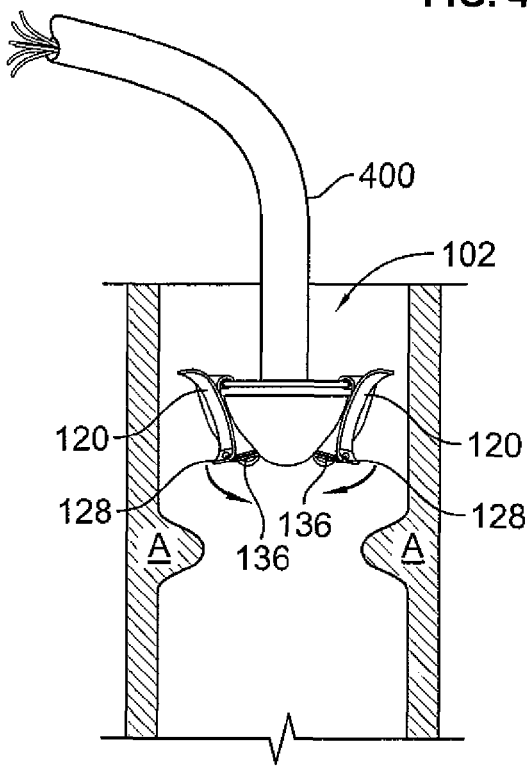

From the orientation of the valve prosthesis 102, and more particularly, of the positioning elements 120 thereof, shown in FIG. 4C, the surgeon/clinician may deflect the lower arcuate regions 128 of the positioning elements 120 inward by pulling the respective lengths 136 of the cords 134 (FIG. 2) a sufficient extent radially inward toward, and/or upward through, the hub 114 (FIG. 2) and the delivery tube 202 in such a way as to continue (see FIG. 4D) an overturning or inverting motion of the positioning elements 120 relative to the flexible ring 106 and the hub 114 (FIG. 2), progressing through sequential orientations as depicted in FIGS. 4D and 4E and arriving at the particularly notable orientation depicted in FIG. 4F. For example, in accordance with embodiments of the present disclosure, the surgeon/clinician may be permitted to accomplish such deflection of the positioning elements 120 by grasping or otherwise seizing respective proximal ends (not shown) of the lengths 136 of the plurality of cords 134 (FIG. 2) disposed outside the delivery catheter 400 and outside the patient's body and pulling such ends outward of the delivery catheter 400 and the patient's body.

Figure 4G:
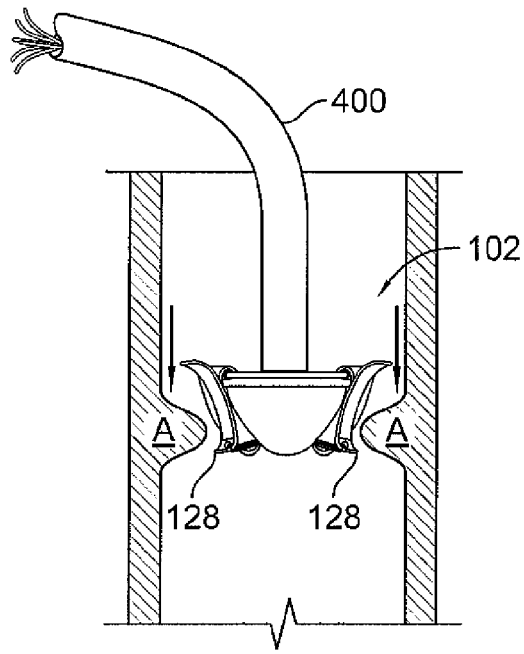
Figure 4H:
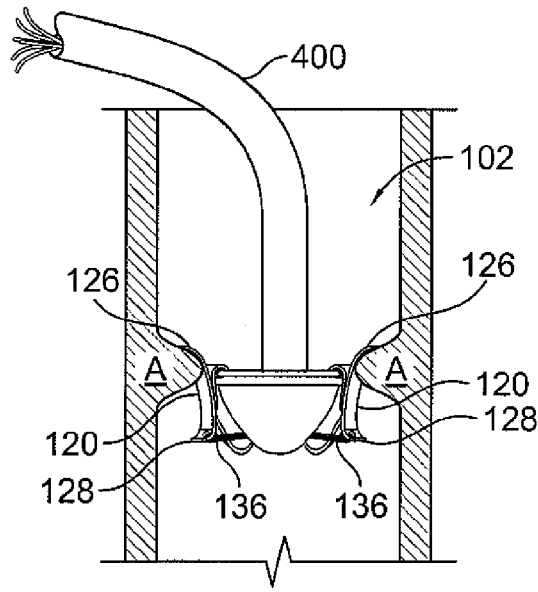

Such withdrawal of the lengths 136 of the cords 134 results in the lower arcuate regions 128 of the positioning elements 120 being pulled radially inwardly, e.g., to a point where the tips 306 of the lower arcuate regions 128 extend at least partially downwardly toward the diseased valve. As shown in FIG. 4G and 4H, such downwardly-directed and relatively more closely spaced lower arcuate regions 128 may be utilized in the manner of a probe or 'plow' to deflect the patient's leaflet membranes (see, e.g., valve structure V in FIG. 2) and/or otherwise facilitate advancing the valve prosthesis 102 downward into the patient's diseased valve such that the valve prosthesis 102 is able to be positioned at an appropriate implantation elevation and an appropriate lateral position relative to the annulus A, As best shown in FIG. 4H, the upper arcuate regions 126 of the respective positioning elements 120 may be cooperatively adapted to be contained within a common plane, e.g., in the manner of a "top hat", so as to facilitate positioning/alignment of the valve prosthesis 102 relative to the annulus A. The circumferentially interrupted aspect exhibited by of the valve prosthesis 102 and collectively defined by the positioning elements 120 may facilitate both inversion of the positioning elements 120 during percutaneous introduction, and effective alignment and tissue engagement/stability upon final implantation and in situ valve function. For example, upon each of the plurality of upper arcuate regions 126 substantially engaging a corresponding part of the upper portion of the annulus A, the valve prosthesis 102 may be generally aligned in a desirable fashion.

Figure 4I:
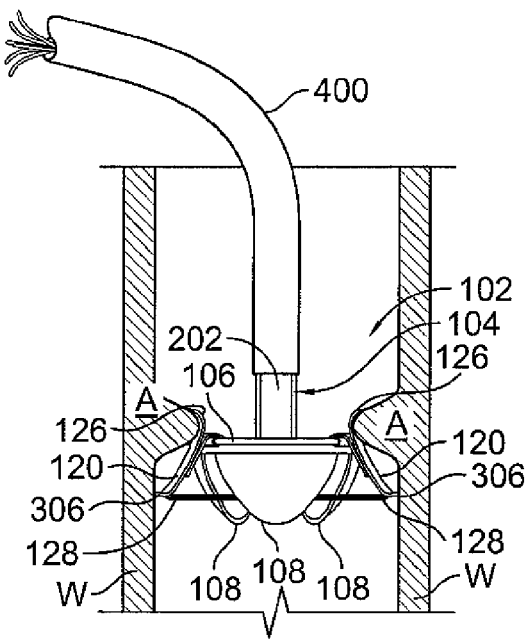

The valve prosthesis 102 may now be further positioned and/or spatially oriented relative to the annulus A in the manner desired by the surgeon/clinician, e.g., as viewed through conventional imaging instrumentation. (Of note, the positioning elements 120 (and particularly, the upper arcuate regions 126 thereof) may be substantially radio-opaque to facilitate imaging identification thereof to confirm proper positioning and spatial orientation of the valve prosthesis 102 relative to the annulus A.) For example, at such time the surgeon/clinician may begin to relax an accumulated degree of tension within the lengths 136 of the plurality of cords 134 (FIG. 2), and thereby begin to allow a corresponding accumulation of energy/spring force contained in the legs 116 (FIG. 2) of the resilient element 112 (FIG. 2) and/or in the positioning elements 120 to cause the lower arcuate regions 128 of the positioning elements 120 to, once again, begin to rotate radially outwardly. Also for example, and as seen in FIG. 4I, the lower arcuate regions 128 may be allowed to rotate radially outward to an extent sufficient to permit the respective tips 306 thereof to contact and/or engage the cardiac tissue comprising the wall W. Having retracted to an extent sufficient to permit such tissue engagement, the legs 116 of the resilient element 112 and/or the positioning elements 120 may still retain sufficient energy/spring force to further cause the respective tips 306 to collectively press against and/or become substantially embedded in place with respect to the wall W. Such collective spring force may be sufficient to permit the lower arcuate regions 128 of the positioning elements 120 to offer a degree of resistance against vertically upward pullout or displacement of the valve prosthesis 102, e.g., a degree of resistance at least comparable to a naturally strong degree of resistance against vertically downward displacement thereof offered by the upper arcuate elements 126 positioned across and/or against the annulus A.

As also seen in FIG. 4I, upon the valve prosthesis 102 being determined to be properly positioned and oriented relative to the annulus A, the cords 134 (FIG. 2) may be withdrawn from the positioning elements 120. Thereafter, the remainder of the delivery structure 104 may be disconnected and/or separated from the valve prosthesis 102 (e.g., the delivery tube 202 may be disconnected from the hub 114 (FIG. 2), thereby leaving the valve prosthesis 102 in an appropriate position relative to the patient's diseased heart valve to serve as a functional replacement thereof. The positioning elements 120 may serve to maintain the native leaflet membranes (see valve structure V in FIG. 2) in an open position, and each of the leaflet membranes 108 and the valve skirt 110 mounted with respect to the flexible ring 106 may function to ensure appropriate directional control of blood flow therethrough.

The disclosed valve prosthesis and associated delivery structures/methods offer numerous advantages relative to existing systems. For example, the positioning elements associated with the disclosed valve prosthesis valve include upper and lower arcuate regions that may advantageously function to engage the annulus as well as the wall of the ventricular chamber below the annulus, thereby securely aligning and stabilizing the valve prosthesis (e.g., in a redeployable manner) relative thereto. In addition, the invertible and collapsible aspects of the valve prosthesis (e.g., for purposes of catheter introduction and the automatic expansion of the valve prosthesis upon exiting the catheter) may facilitate efficient percutaneous delivery and in situ manipulation of the disclosed valve prosthesis system. Further, the disclosed valve skirt may enhance sealing functionality of the disclosed valve prosthesis when positioned in situ as compared to that which might otherwise be the case (e.g., without such a skirt and/or the annular sealing function provided thereby). Still further, the "top-hat" geometry and/or functionality of the upper arcuate regions of the positioning elements may advantageously function to accurately and securely position the valve prosthesis relative to an annulus and associated anatomical structures.

It will be appreciated that the disclosed design and implantation methodology may not require extensive surgery, and that the disclosed positioning elements may function to provide stable and well aligned implantation, central blood flow, and/or a stable platform for the leaflet membranes. Moreover, positioning may be more precise than with a balloon expandable device, such as a stent. Additionally, and also unlike a stent, the positioning may potentially be repeated (e.g., until the desired implantation position and/or orientation is achieved). The heart valve prosthesis described herein may also allow anchoring relative to the valve annulus in states of the diseased valve in which a stent may not encounter sufficient tissue to which to adhere (e.g., as is commonly the case with respect to mitral valve disease).

In accordance with exemplary embodiments of the present disclosure, the heart valve prosthesis may be placed squarely at the site of a diseased heart valve, as distinct from certain existing heart valve prosthesis implementations characterized by the use of stents configured for placement in the connecting blood vessels adjacent to and/or near the diseased heart valve, and, as such, are designed to be disposed in spaced relation therewith, whether during or after implantation, or during in situ operation. As a result, the ability of the operator or surgeon to reposition and/or re-anchor the heart valve prosthesis in order to more accurately position the heart valve prosthesis in the opening of the diseased heart valve, such as may be provided in accordance with embodiments of the present disclosure, may be of increased significance.

Figure 5:
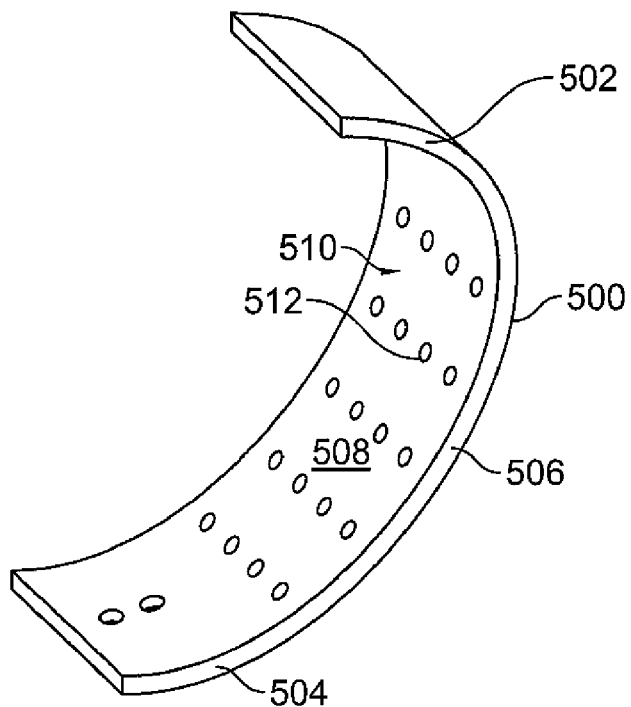
FIGS. 5, 6, and 7 are schematic perspective views of variations of a positioning element according to the present disclosure.
Figure 6:
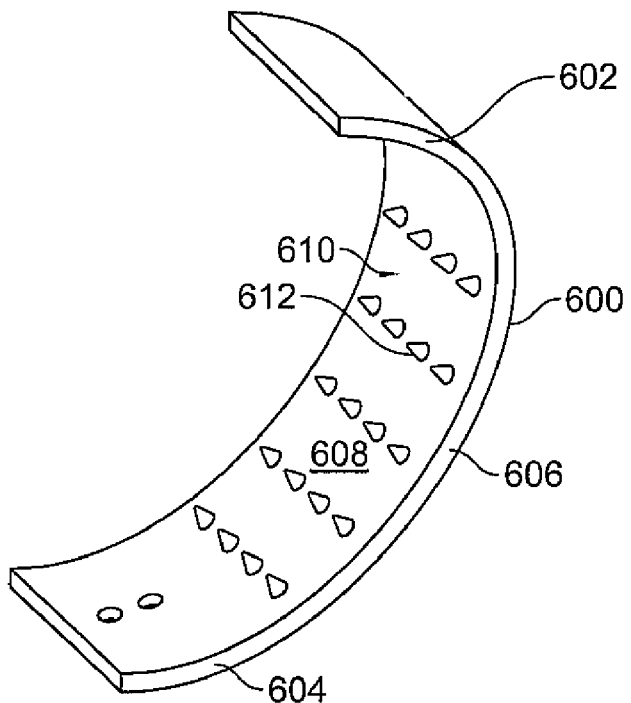
Figure 7:
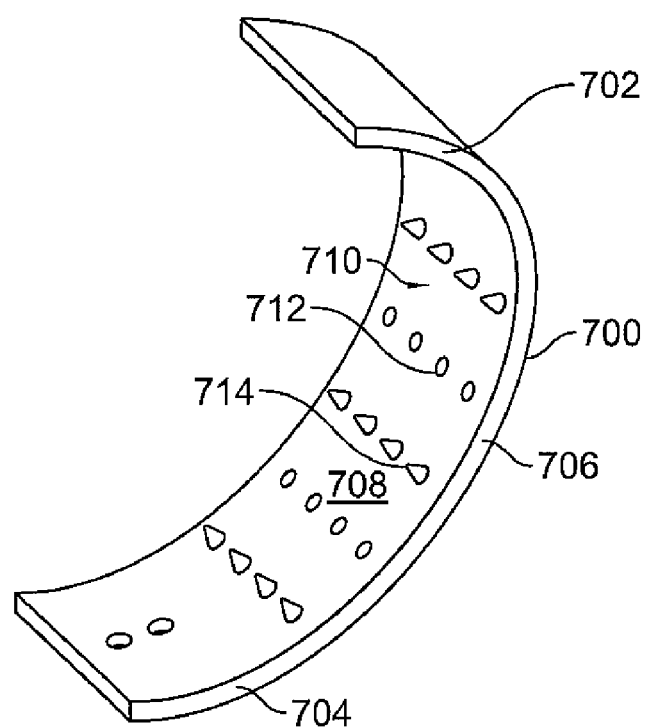

The positioning elements 120 of the present disclosure may be implemented by one or more of a plurality of variations, including those depicted in FIGS. 5-7. More particularly, a positioning element 500 depicted in FIG. 5 is one such variation of the positioning element 120. The positioning element 500 may include upper and lower arcuate regions 502, 504, an intermediate region 506 disposed therebetween, and an outer surface 508. An array 510 of holes 512 may be formed in the outer surface 508 in a vicinity of the intermediate region 506 to encourage in-growth of tissue, increasing positional and orientational stability in situ. Referring now to FIG. 6, a positioning element 600 is another such variation of the positioning element 120. The positioning element 600 may include upper and lower arcuate regions 602, 604, an intermediate region 606 disposed therebetween, and an outer surface 608. An array 610 of spikes or spurs 612 may be provided, extending from the outer surface 608 in a vicinity of the intermediate region 606 to facilitate secure engagement of tissue, similarly increasing positional and orientational stability in situ. A positioning element 700 depicted in FIG. 7 is yet another variation of the positioning element 120. The positioning element 700 may include upper and lower arcuate regions 702, 704, an intermediate region 706 disposed therebetween, and an outer surface 708. An array 710 of holes 712 may be formed in, and spikes or spurs 714 may be provided so as to extend from, the outer surface 708 in a vicinity of the intermediate region 706 to facilitate both in-growth of tissue and secure engagement of tissue, also increasing positional and orientational stability in situ. While the holes 512 and 712 and the spurs 612 and 714 are shown in FIGS. 5-7 as appearing in the respective intermediate regions 506, 606, 706 of the respective positioning elements 500, 600, 700, such features may alternatively, and/or in addition, be positioned in one or both of the upper 502, 602, 702 and lower 504, 604, 704 arcuate regions thereof.

Figure 8:
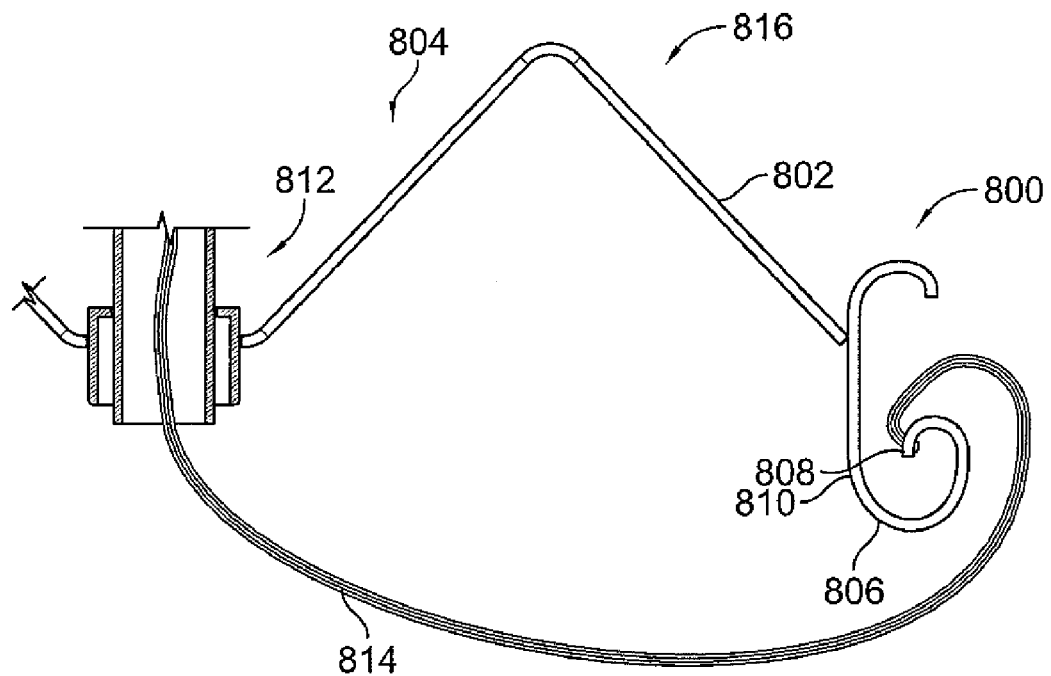
FIGS. 8, 9, 10, 11 and 12 are schematic side elevational and perspective views of variations of a prosthetic heart valve in accordance with the present disclosure.

Another variation of the positioning element 120 is embodied by the positioning element 800 of FIG. 8. A leg 802 of a resilient element 804 may support the positioning element 800, which may in turn include a lower arcuate region 806 having a tissue-engaging tip 808 that, in a retracted state of the lower arcuate region 806, may be coiled or 'rolled up' so as to extend inward toward an intermediate region 810 of the positioning element and/or downward toward itself. A deployment structure 812 may include a cord 814 attached to the lower arcuate region 806 (e.g., near the tip 808 thereof) to uncoil the lower arcuate region 806 so as to permit the tip 808 to be redirected outward so as to be capable of engaging with a the cardiac tissue comprising a patient's heart wall (not shown). A surgeon/clinician may be permitted to pull outward on the cord 814 during positioning of the positioning element 800, and once the tip 808 has begun to engage the cardiac tissue, to release the cord 814, allowing an accumulated energy/spring force inherent in the lower arcuate region 806 (e.g., the same having a coil-spring configuration) to impinge with additional force upon the cardiac tissue. Multiple instances of the positioning element 800 may be provided in a valve prosthesis 816 (not otherwise shown) such that at least some balancing of reaction forces can be achieved, and an upper arcuate region 818 of the positioning element 800 may have a similar coiled configuration (not separately shown) to that of the lower arcuate region 806.

Figure 9:
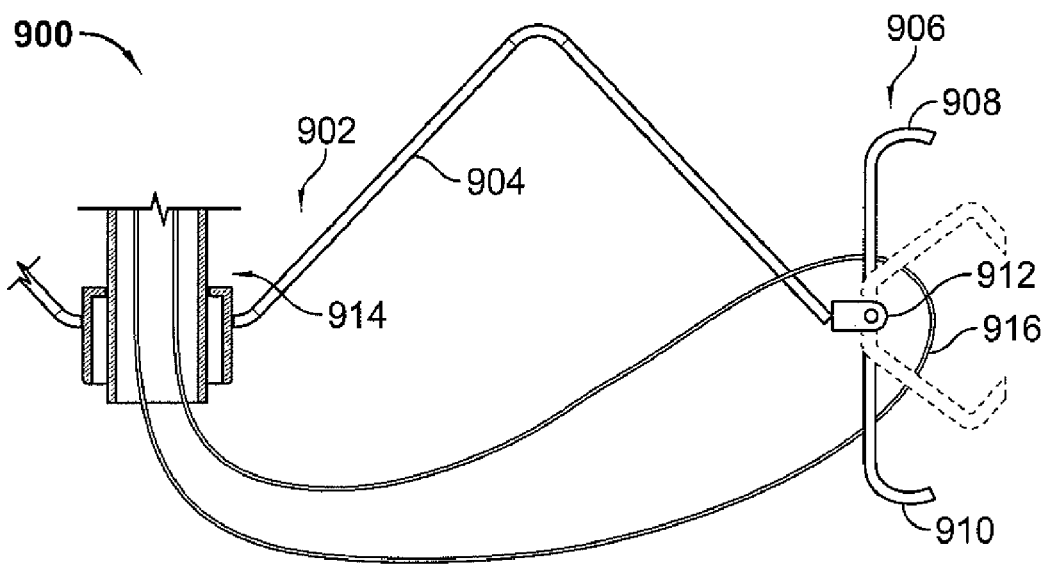

A modified version of the valve prosthesis 102 is embodied by the valve prosthesis 900, the latter being shown partially and schematically in FIG. 9. The valve prosthesis 900 may include a resilient element 902 having a leg 904 generally similar to the legs 116 associated with the above-described resilient element 112. The leg 904 may support a claw 906 having an upper jaw 908, a lower jaw 910, and a hinge 912 disposed between the upper and lower jaws 908, 910. The valve prosthesis 900 may further include a torsional spring (not shown) for biasing the upper and lower jaws 908, 910 of the claw 906 in favor of closure toward each other, and securely engaging the cardiac tissue of a patient's heart wall.

A deployment structure 914 may include a cord 916 attached to the upper and lower jaws 908, 910. A surgeon/clinician may be permitted to pull outward on the cord 916 to hold the claw 906 open during positioning of the claw 906. Once the claw 906 has begun to engage the cardiac tissue (e.g., an annulus A as shown in FIG. 2), the surgeon/clinician may be permitted to release the cord 916, allowing the spring bias to act on the upper and lower jaws 908, 910 and thereby allowing the claw 906 to affix itself to the cardiac tissue. Multiple instances (not shown) of the claw 906 may be provided in the valve prosthesis 900.

Figure 10:
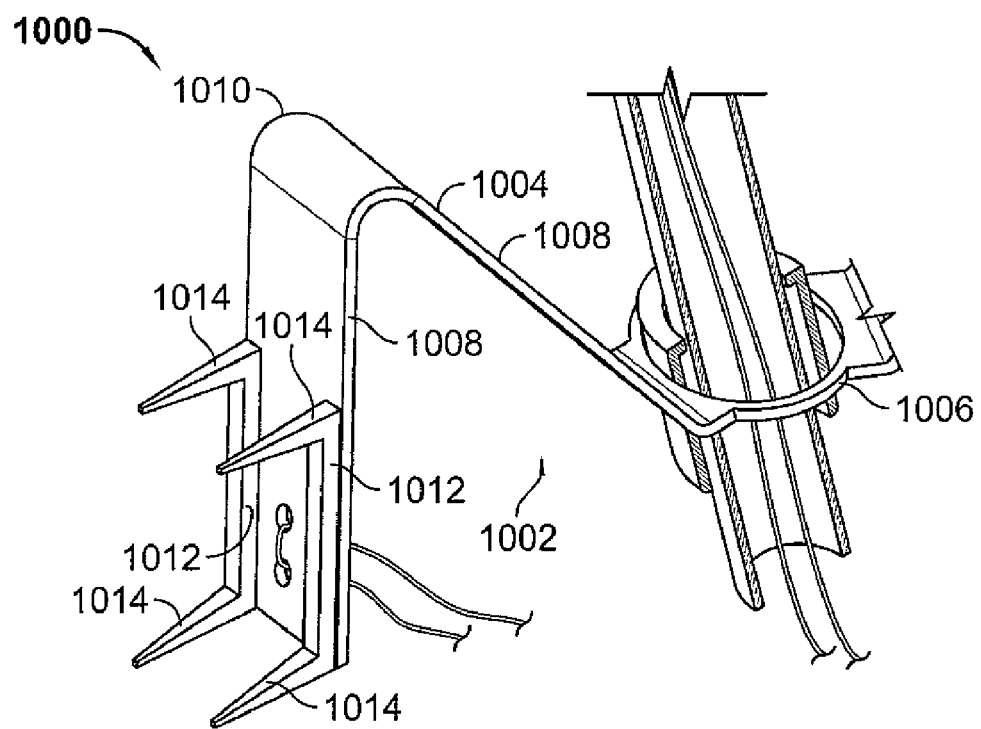
Figure 11:
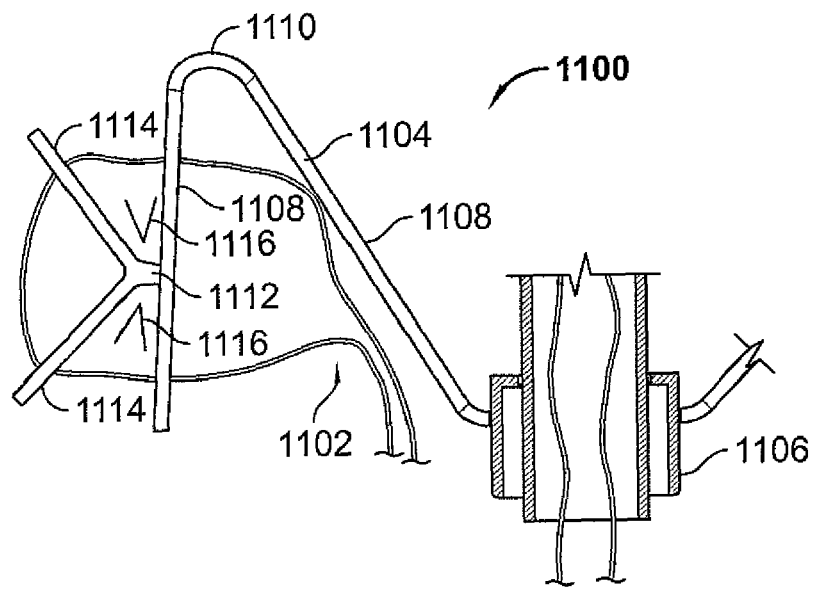
Figure 12:
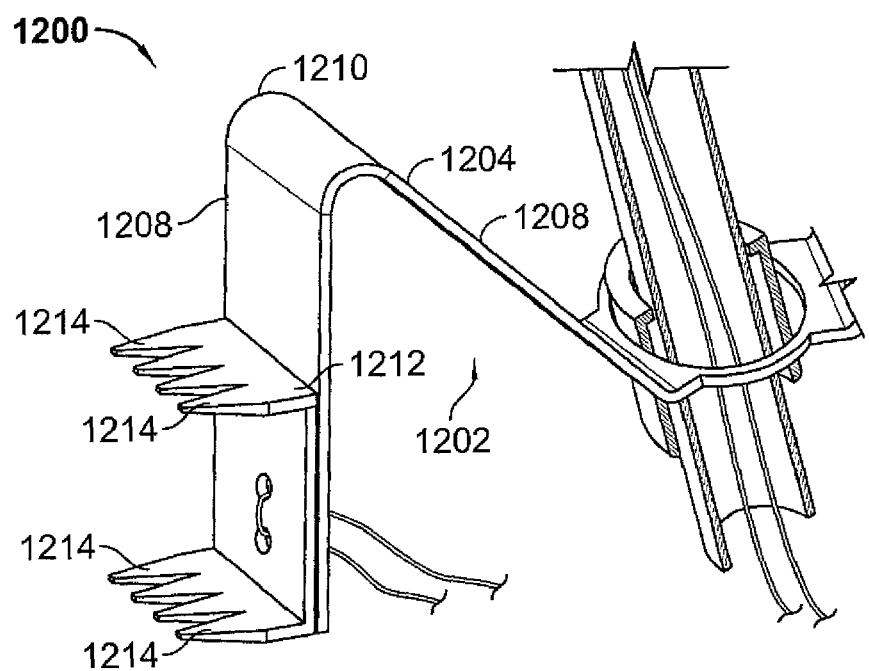

Respective alternative modified versions of the valve prosthesis 102 are further embodied by the valve prostheses 1000, 1100, and 1200, shown partially and schematically in FIGS. 10, 11 and 12, respectively. The valve prosthesis 1000 of FIG. 10 may include a resilient element 1002 having multiple instances of a leg 1004 extending from a hub 1006. The leg 1004 may itself be a spring, and may include at least two leaves 1008 joined at an arcuate or bend region 1010. The valve prosthesis 1000 may further include one or more engaging elements 1012, each of which may include a plurality of prongs 1014 for piercing and/or otherwise invasively engaging cardiac tissue as appropriate to secure the valve prosthesis 1000 in place relative to a diseased heart valve, and/or relative to an annulus associated therewith. The engaging element 1012 may be supported by one of the leaves 1008 of the leg 1004, and the valve prosthesis 1000 may include a plurality of sets of two engaging elements 1012 (e.g., having two prongs 1014 each) as shown in FIG. 10.

The valve prosthesis 1100 of FIG. 11 may include a resilient element 1102 having multiple instances of a leg 1104 extending from a hub 1106. The leg 1104 may itself be a spring, and may include at least two leaves 1108 joined at an arcuate or bend region 1110. The valve prosthesis 1100 may further include one or more engaging elements 1112, each of which may include two arms 1114 extending outward from a common point of connection in a V shape. The valve prosthesis 1100 may further include biasing springs (indicated schematically at reference numeral 1116) for urging the arms 1114 of the engaging elements 1112 together for purposes of closing the engaging element 1112 about an annulus associated with a patient's diseased heart valve. The engaging element 1112 may be supported by one of the leaves 1108 of the leg 1104, and the valve prosthesis 1100 may include a plurality of such engaging elements 1112.

The valve prosthesis 1200 of FIG. 12 may include a resilient element 1202 having multiple instances of a leg 1204 extending from a hub 1206. The leg 1204 may itself be a spring, and includes at least two leaves 1208 joined at an arcuate or bend region 1210. The valve prosthesis 1200 may further include one or more engaging elements 1212, each of which may include a plurality of teeth 1214 for engaging cardiac tissue as appropriate to secure the valve prosthesis 1200 relative to a diseased heart valve. The engaging element 1212 may be directly affixed to one of the leaves 1208 of the leg 1204 (e.g., the valve prosthesis 1200 may include a plurality of engaging elements 1212 having two rows of teeth 1214 each as shown in FIG. 12). In some embodiments (not separately shown), the engaging element 1212 may be hinged at a central location between the two rows of teeth 1214 such that the engaging element 1212 may be movable to at least some degree relative to the leg 1204. Accordingly, in at least some such embodiments, the engaging element 1212 may be utilized in the manner of a toothed claw otherwise structurally and functionally similar to the claw 906 described above with reference to FIG. 9.

Figure 13:
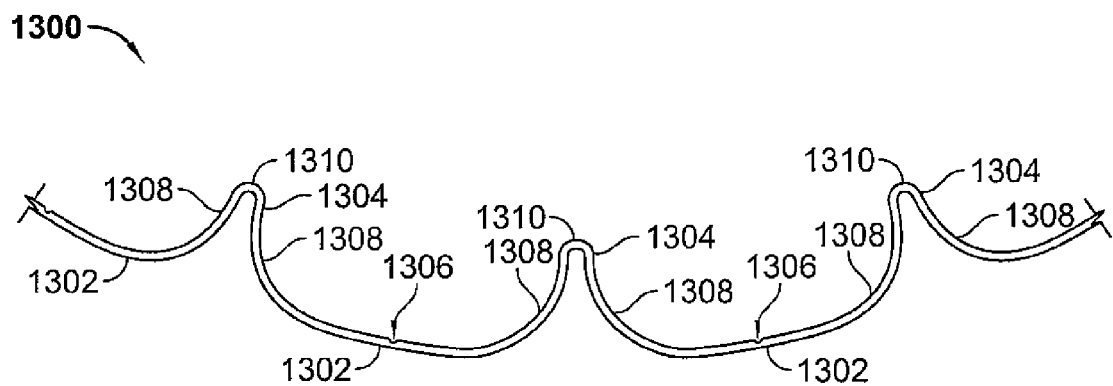
FIGS. 13 and 14 are respective side and perspective views of a flexible ring according to the present disclosure.
Figure 14:
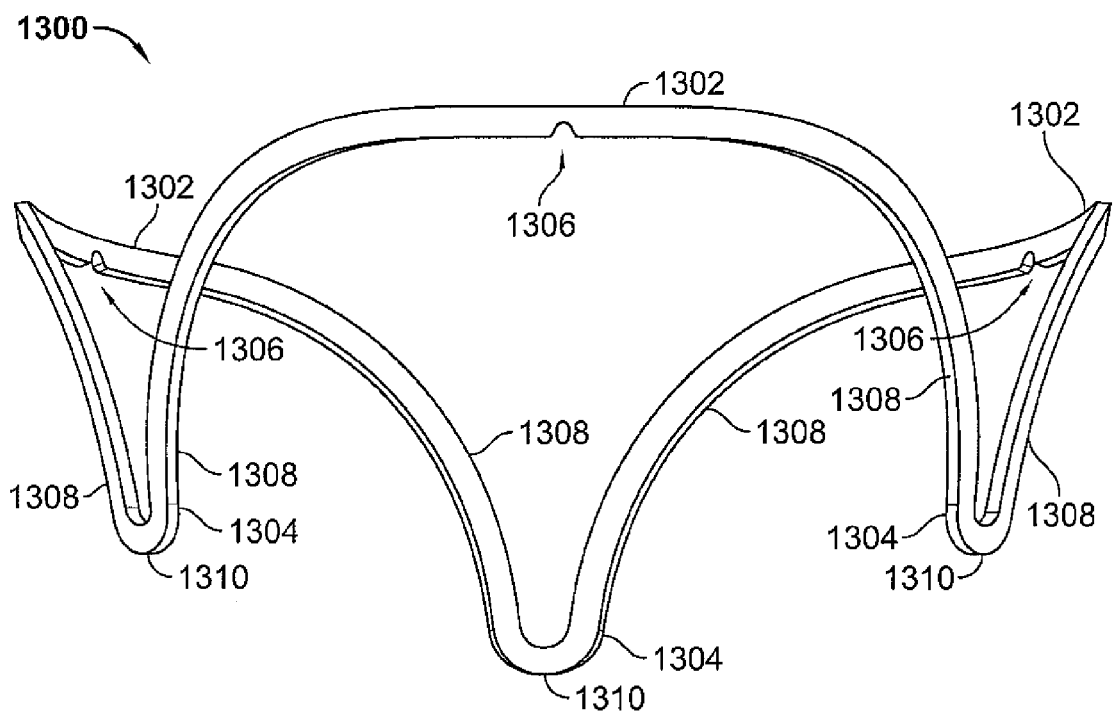

A variation of the above-discussed flexible ring 106 is embodied by a flexible ring 1300 illustrated in FIGS. 13 and 14. The flexible ring 1300 may be resilient such that it may tend (e.g., absent any substantial compressive forces) to expand outward to assume a three-dimensional shape (e.g., the three-dimensional shape shown FIG. 14), in which the flexible ring 1300 may have a not insubstantial vertical height, in addition to a characteristic lateral width or diameter. More particularly, the flexible ring 1300 may include multiple instances of a hoop segment 1302. The hoop segments 1302 may be contained within a common horizontal plane (e.g., upon the flexible ring 1300 being expanded out to its maximum width and height) wherein the hoop segments may be separated by and/or coupled via a corresponding number of instances of a coupling segment 1304 extending vertically relative to the common horizontal plane, constituting at least a portion of the height extent of the flexible ring 1300. Each hoop segment 1302 may further include a notch 1306 to facilitate secure coupling of one or more of a valve skirt similar to the above-described valve skirt 110, at least one leaflet membrane similar to the above-described leaflet membranes 108, and/or an associated annulus or cuff similar to that described above. For example, such coupling may be obtained via a knotted suture (not shown) at least partially lodged within the notch 1306 so as to restrict relative movement of the valve skirt, leaflet membrane, and/or cuff relative to and/or about a circumference of the flexible ring 1300. Each of the coupling segments 1304 may comprise a spring having two leaves 1308 joined at an arcuate or bend region 1310, whereby the flexible ring 1300 may be particularly amenable to being radially compressed and/or to assume a compact shape suitable for compressing a corresponding valve prosthesis (not separately shown) of which the flexible ring 1300 is a part, and/or passing such a prosthesis through a narrow-gauge catheter (not shown). More particularly, because the flexible ring 1300 may include intermittent breaks in its circumference in the plane of the hoop segments 1302 (e.g., associated with the coupling segments 1304), its geometry may further contribute to an elastic radial compressibility exhibited by the flexible ring 1300. The bend regions 1310 of the coupling segments 1304 may further serve as anchoring points functionally similar to the notches 1306. For example, such notches 1306 may be used as anchoring points for securing, and/or limiting a length extent of, commisure seams (not shown in FIGS. 13-14; see, e.g., corresponding structure illustrated and described below with reference to FIGS. 16-20) formed between corresponding leaflet membranes (not shown) of a heart valve prosthesis (not shown) incorporating the flexible ring 1300 in accordance with embodiments of the present disclosure.

Figure 15:
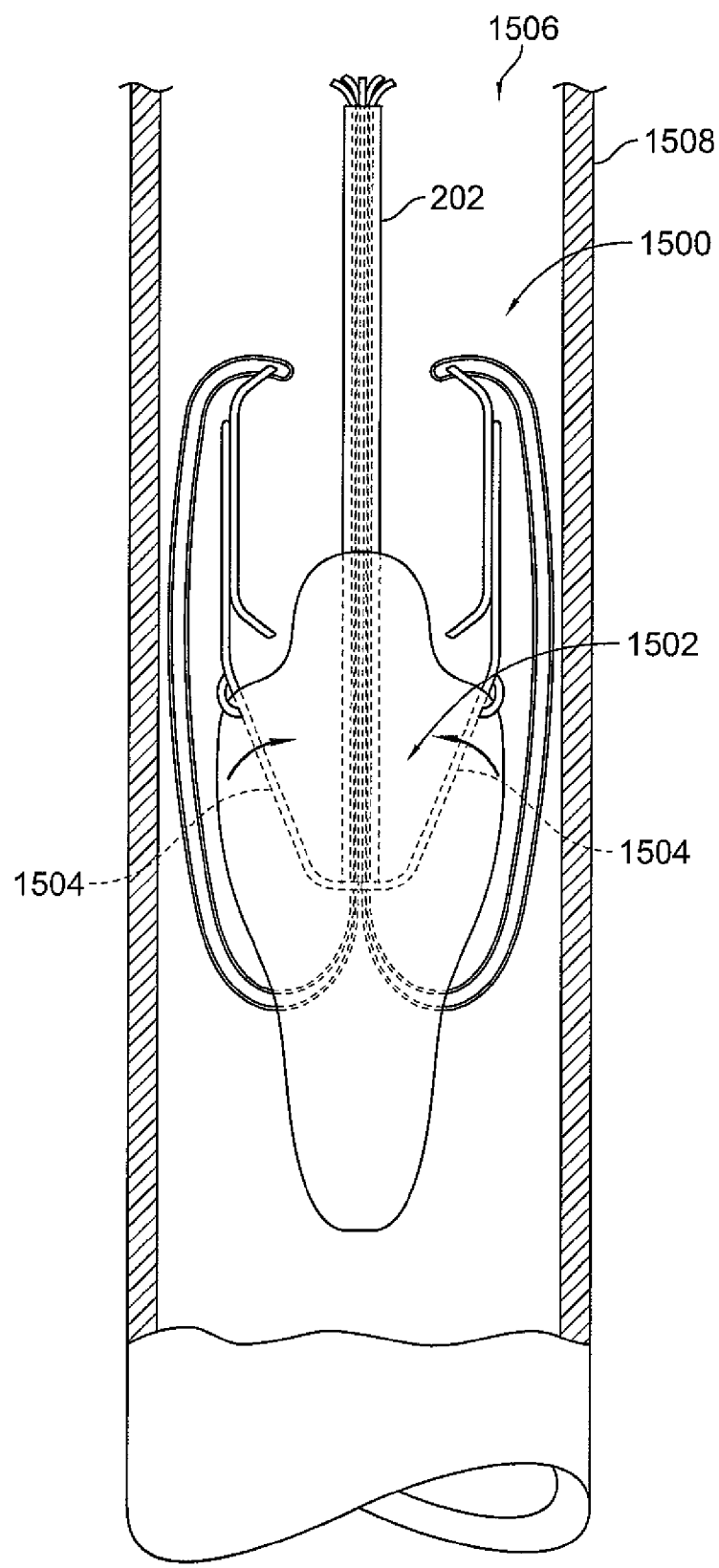
FIG. 15 is a schematic side view of an exemplary valve prosthesis contained within a delivery catheter in accordance with the present disclosure.
Figure 16:
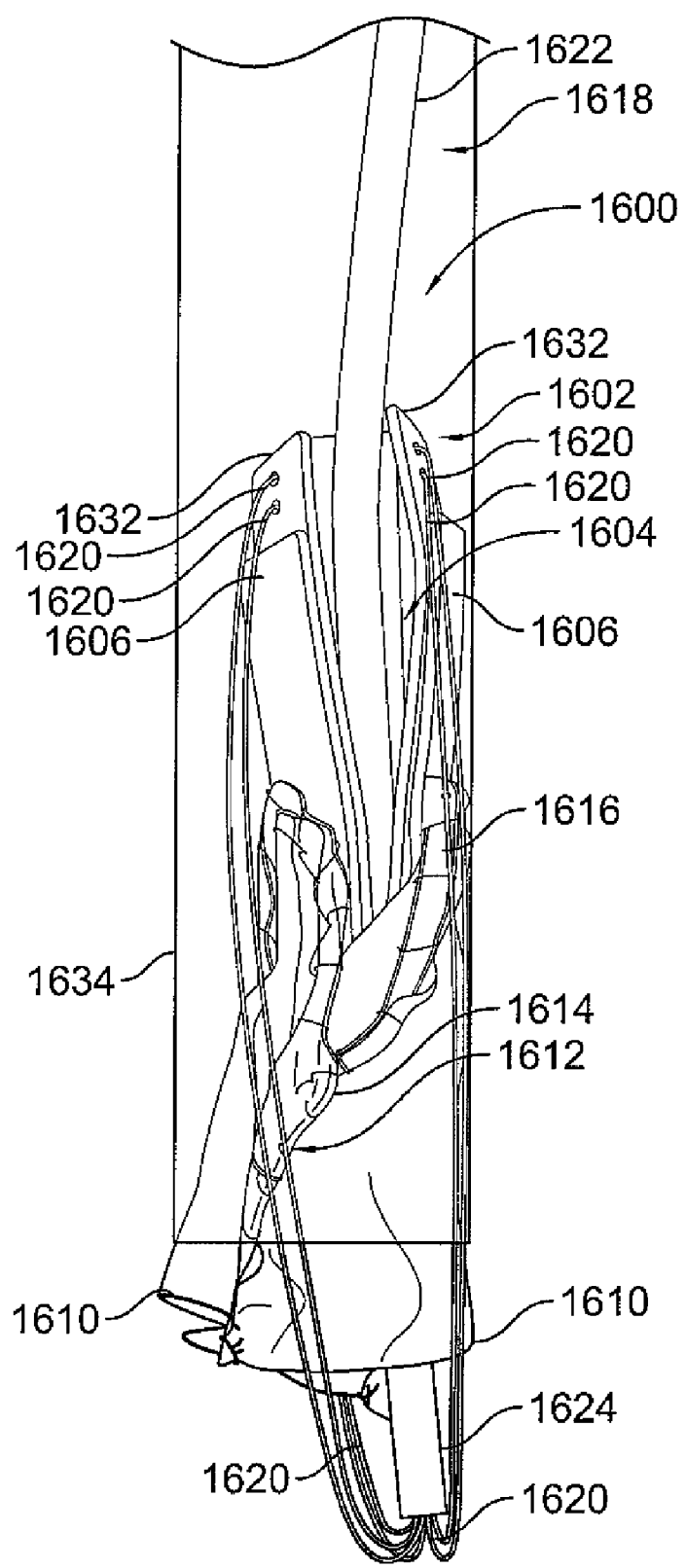
FIGS. 16, 17, 18, 19 and 20 are sequential side views of an exemplary valve prosthesis being outwardly deployed from within a delivery catheter in accordance with the present invention.
Figure 17:
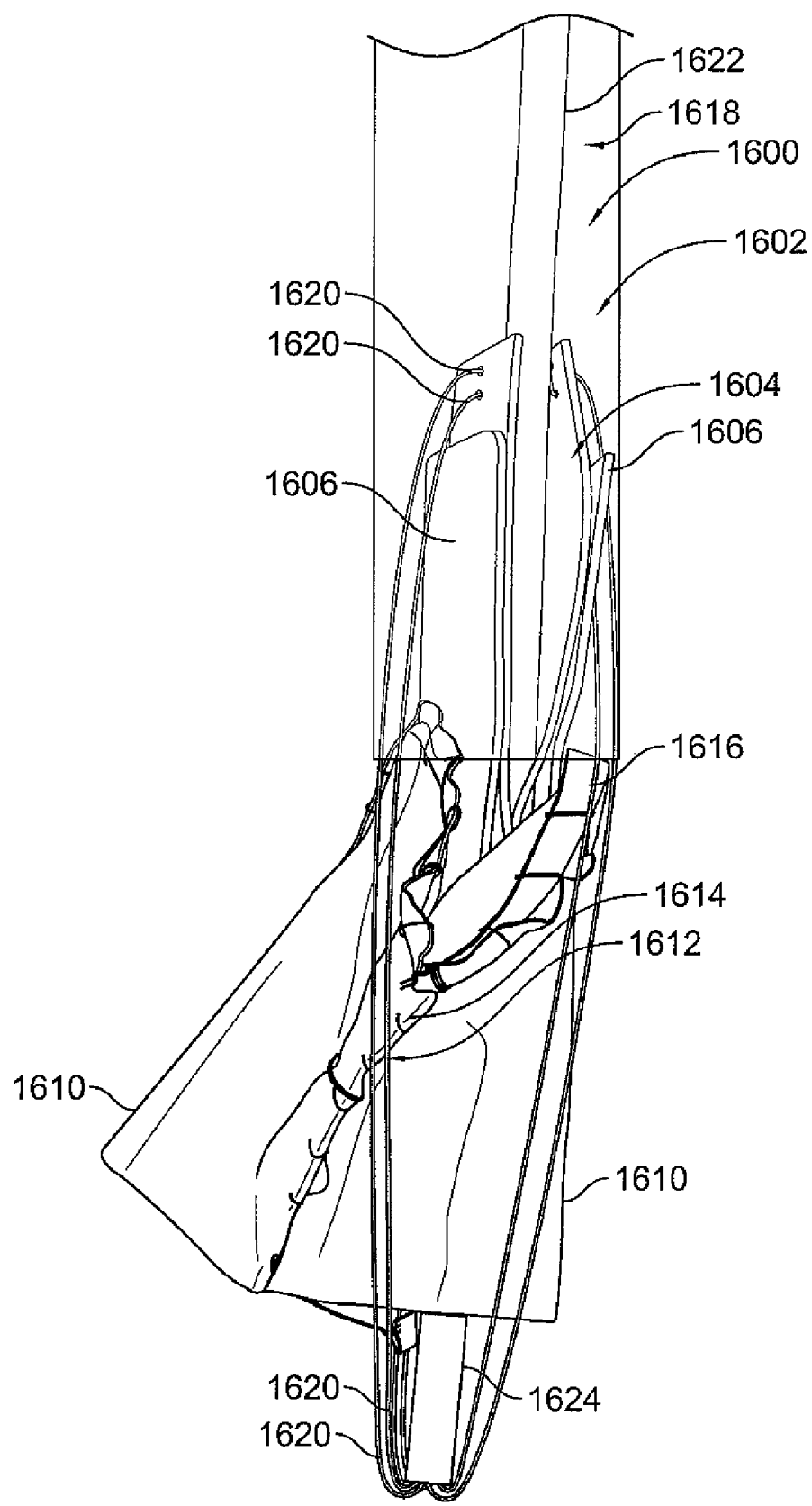
Figure 18:
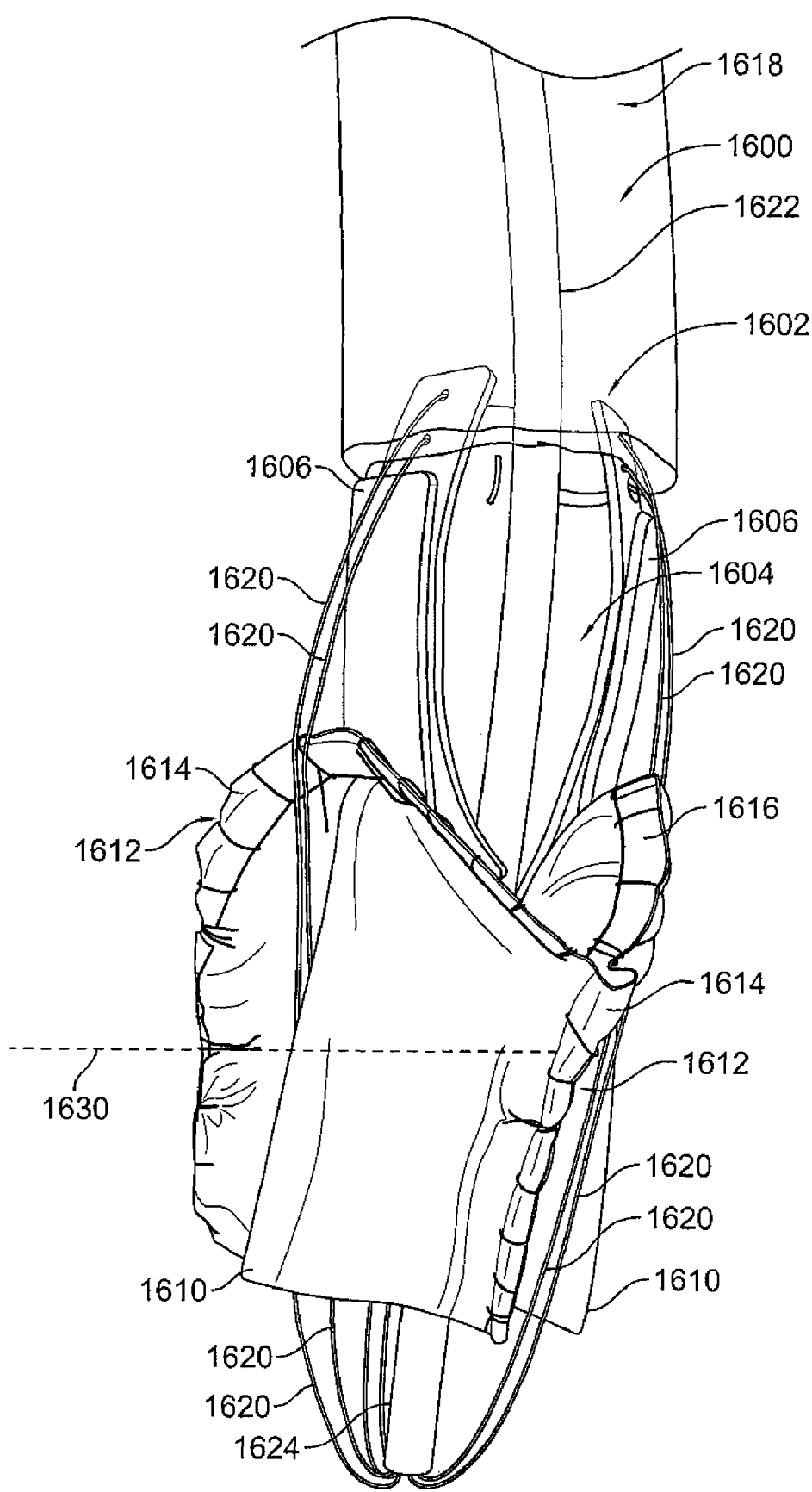
Figure 19:
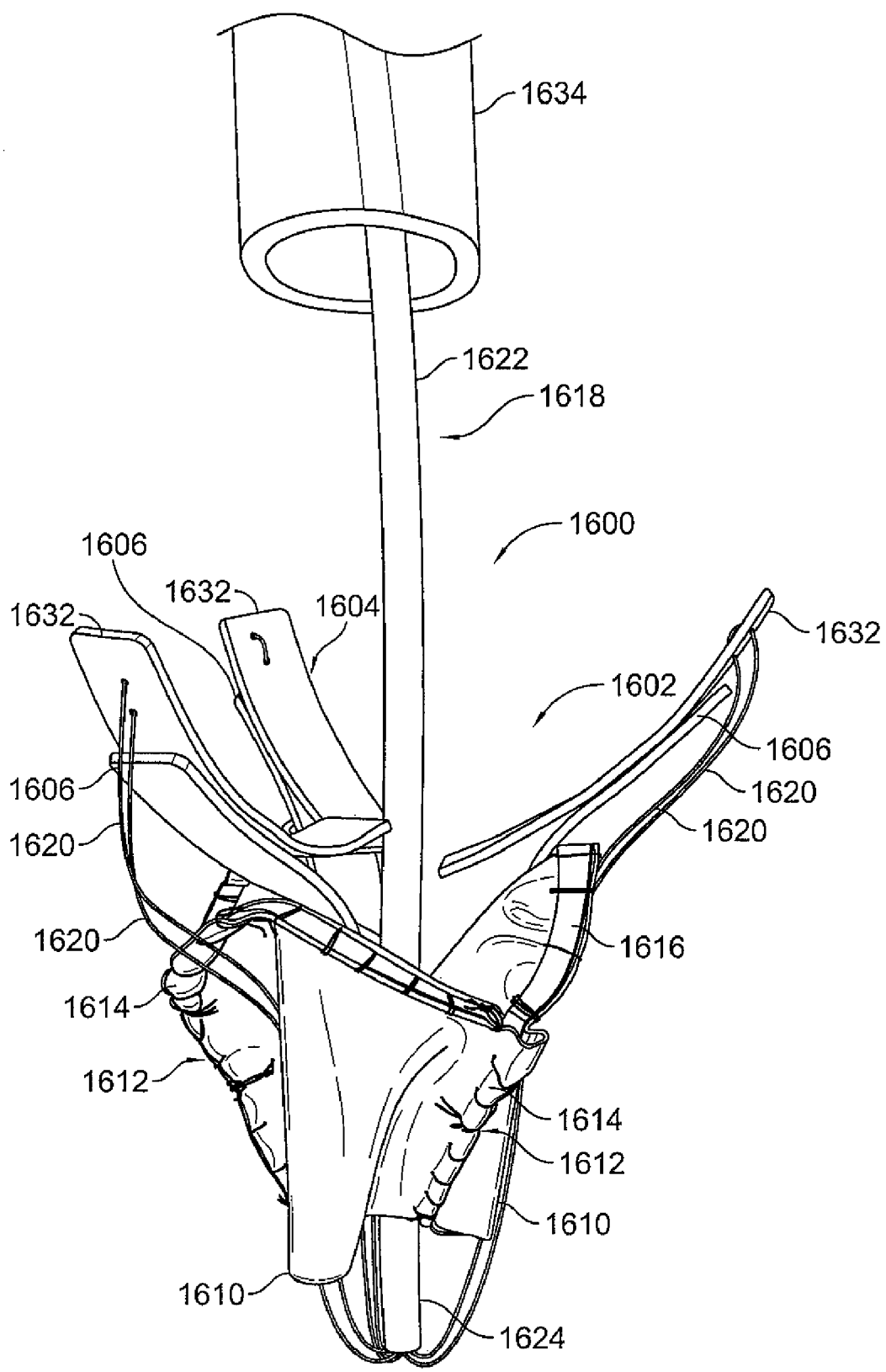

A variation of the valve prosthesis 102 in accordance with the present disclosure is embodied by a valve prosthesis 1500 illustrated in FIG. 15. The resilient element 1502 of the valve prosthesis 1500 may be structurally and functionally similar to the above-described resilient element 112. The legs 1504 of the resilient element 1502 may flex inwardly toward the delivery tube 202. For example, the legs 1504 may be adapted to flex inwardly toward the delivery tube 202 in a manner that facilitates an enhanced degree of radial compression of the valve prosthesis 1500. Such flexure of the legs 1504 may further permit the valve prosthesis 1500 to pass along a lumen 1506 of a catheter 1508 exhibiting a smaller internal diameter than would otherwise be the case.

A modified version of the valve prosthesis system 100 in accordance with the present disclosure is embodied by a valve prosthesis system 1600 illustrated in various stages of operation in FIGS. 16, 17, 18, 19, and 20. The valve prosthesis system 1600 may include a valve prosthesis 1602 that is a modified version of the valve prosthesis 102 including substantially all structural and functional features thereof, with at least some exceptions as discussed below. The valve prosthesis 1602 may include a resilient element 1604 having multiple instances of a leg 1606 extending radially outward from a hub 1608, and multiple instances of a leaflet membrane 1610. Commissures 1612 between the leaflet membranes 1610 may be partially closed, or at least limited in length via respective sutured seams 1614 formed between the leaflet membranes 1610. For example, the sutured seams 1614 may extend from a flexible ring 1616 of the valve prosthesis 1602, or from a location in spaced relation below the flexible ring 1616 (e.g., as in embodiments of the valve prosthesis (not specifically shown) in which each of the leaflet membranes 1610 forms a portion of a larger membrane structure of unitary construction), downward to a point coinciding with respective free ends or distal edges of the leaflet membranes 1610. The valve prosthesis system 1600 may further include a delivery structure 1618 that, in addition to having cables 1620 and a delivery tube 1622 structurally and functionally similar to corresponding aspects of the delivery structure 104, further includes a tower 1624 extending downward from the hub 1608.

Among other functions that may be provided thereby, the tower 1624 may at least participate in defining a central axis 1625 of the valve prosthesis system 1600, and may further introduce an axial (e.g., vertical or lengthwise) separation between an elevation (e.g., generally indicated at 1626 in FIG. 20) at which the legs 1606 meet the hub 1608 and an elevation (e.g., generally indicated at 1628 in FIG. 20) at which the cables 1620 extend, and/or are deployed, outward from the central axis 1625. As shown in FIGS. 16-20, such an arrangement may have the advantage of displacing and/or routing the cables 1620 generally away from an elevation (e.g., generally shown at 1630 in FIG. 18) occupied by the leaflet membranes 1610, and/or by the sutured seams 1614 disposed therebetween. More particularly, such an arrangement may advantageously reduce and/or eliminate a risk of the cables 1620 abrading or cutting the leaflet membranes 1610 and/or the sutures of the sutured seams 1614 during a process of deploying, adjusting a position of, and/or otherwise implanting the valve prosthesis 1602. Such a risk does not necessarily exist with respect to any particular embodiment of a heart valve prosthesis in accordance with the present embodiment. For example, embodiments in accordance with the present disclosure of the heart valve prosthesis 102 shown and described herein with reference to FIGS. 1, 2, 3A-3B, and 4A-4I exist in which such a risk is either remote, or for all practical purposes, non-existent. Nevertheless, it is contemplated that such a risk may exist with respect to at least some heart valve prosthesis embodiments in accordance with the present disclosure, including, for example, embodiments in which the particular dimensions of, or the particular materials specified for, the sutures of the sutured seams 1614, and/or the leaflet membranes 1610, are optimized for purposes of providing maximum functionality and/or durability in situ, but wherein such optimization unfortunately has the effect of leaving such components at increased risk of damage from frictional interaction with the cables 1620 during prosthesis implantation. In such circumstances, at least, the use of a tower 1624, or of another component structurally and/or functionally similar thereto, to introduce an appropriate axial separation between the cables 1620 and the leaflet membranes 1610, and/or between the cables 1620 and the sutured seams 1614, may provide a particular advantage.

Figure 20:
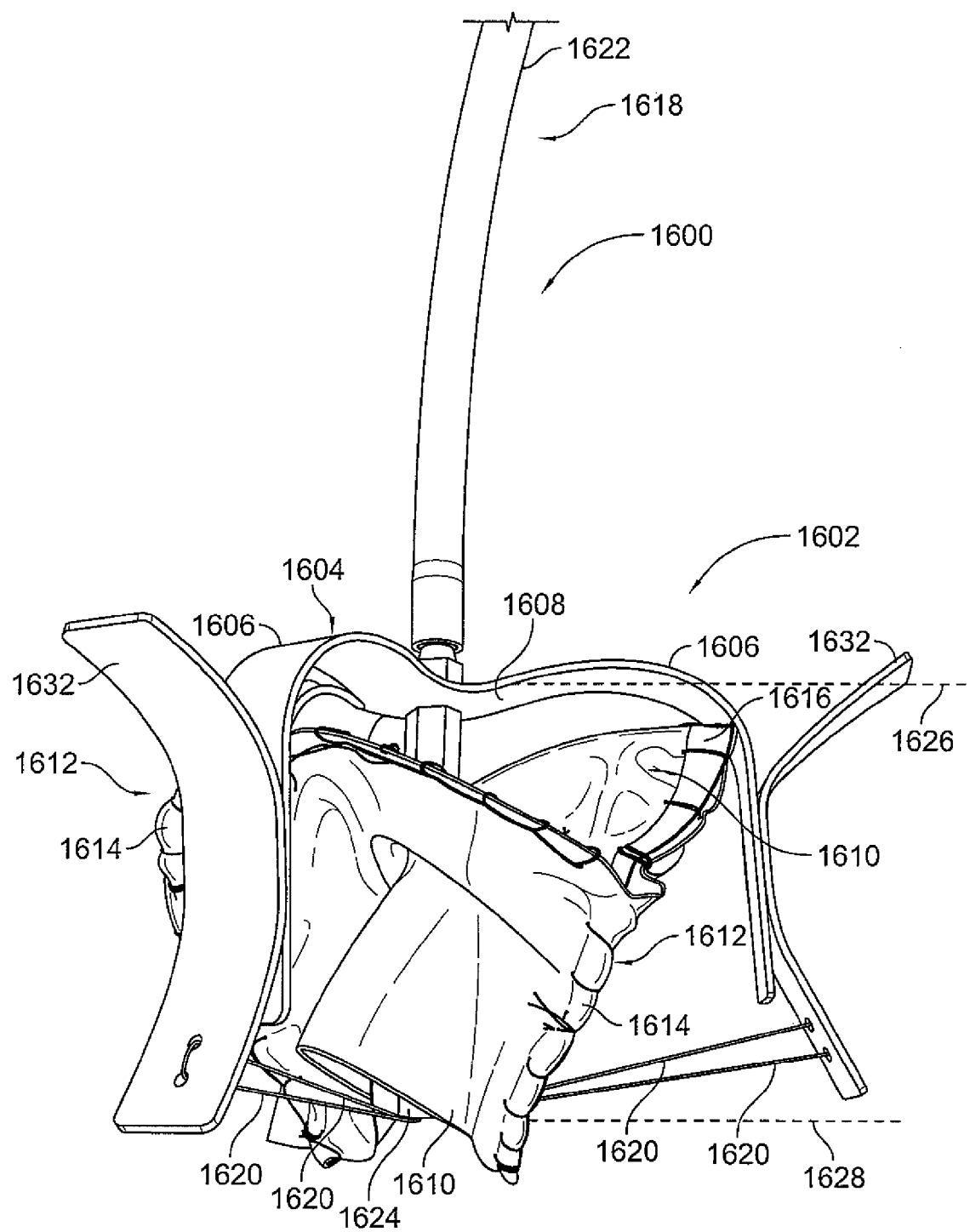

As is particularly evident in FIG. 20, such an arrangement may further permit additional energy and/or spring force to be built up within the resilient element 1604 by imparting significant flexure to the resilient element 1604 where the legs 1608 meet the hub 1606. For example, and as sequentially illustrated in FIGS. 16-20, a sufficient amount of flexure may be imparted thereby to the resilient element 1604 to cause the hub 1606 to be raised to an elevation substantially entirely above those of the respective positioning elements 1632 during a corresponding process of deployment from a catheter 1634, in which the positioning elements 1632 may be overturned or inverted relative to the flexible ring 1616 and the hub 1608 in preparation for placement of the valve prosthesis 1602 with respect to a patient's diseased heart valve. Such elevated placement of the hub 1608 relative to the positioning elements 1632 may further persist in the final in situ configuration of the valve prosthesis 1602 within the diseased heart valve (not specifically shown), such that an elevation of the hub 1608 may be and/or remain even with or above that of the corresponding annulus A (see FIG. 2 for comparison). Still further, in such circumstances, the legs 1608 may assume a final configuration relative to the hub 1606 such that: i) the legs 1608 either effectively no longer extend vertically upward from the hub 1608; or ii) an extent to which the legs 1608 continues to so extend upward from the hub 1606 is substantially reduced; and/or iii), the legs 1608 have substantially completely been overturned relative to the flexible ring 1616 so as to extend substantially completely downwardly from the hub 1608. Any one or all of these arrangements of the legs 1608 of the resilient element 1604 relative to the hub 1606 thereof and/or relative to the flexible ring 1616 may have the advantageous effect of reducing an occurrence of or an extent of eddies or turbulence in the flow of blood past or through the resilient element 1604. In such circumstances, a risk of undue tissue damage in the associated blood flow volume may be reduced. More particularly, to the extent such eddies and/or turbulence may be attenuated as described above, an extent and/or magnitude of a shear force characteristic of the flow of blood through the heart valve prosthesis 1602, and potentially associated with and/or causing such tissue damage, may be beneficially adjusted, limited, and/or reduced.

Figure 21:
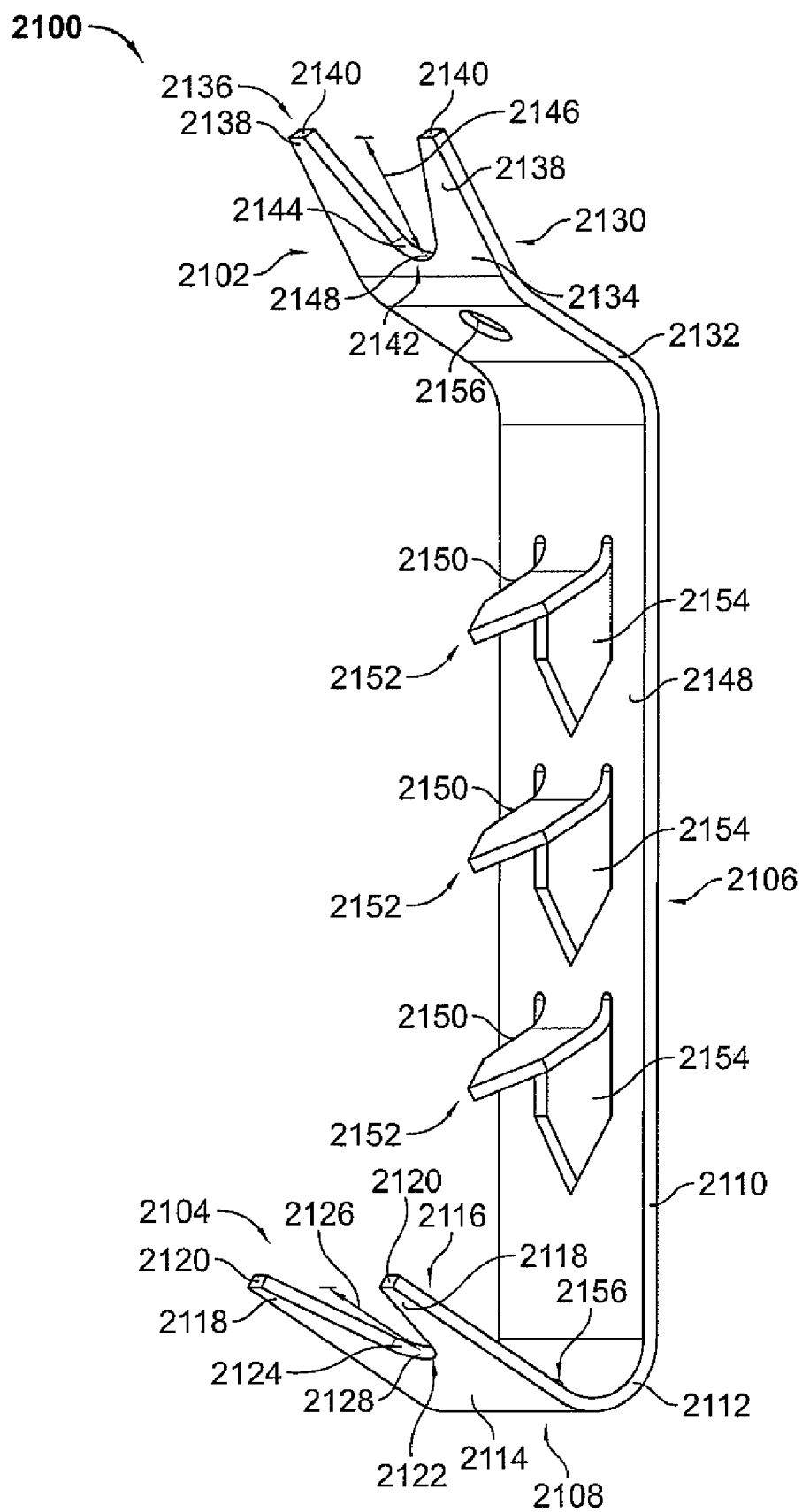
FIG. 21 is a schematic perspective view of a positioning element according to the present disclosure.

In accordance with exemplary embodiments of the present disclosure, a modified version of the positioning element 120 is embodied by the positioning element 2100 of FIG. 21. The positioning element 2100 may be fabricated from a metallic material. For example, the positioning element 2100 may be fabricated from a shape memory alloy (SMA, also known as a smart alloy, memory metal, or muscle wire) such as the nickel-titanium alloy Nitinol. The positioning element 2100 may include proximal and distal end regions 2102, 2104, and an intermediate region 2106 disposed between the proximal and distal end regions 2102, 2104.

The intermediate and distal end regions 2106, 2104 of the positioning element 2100 may collectively define a hook 2108 for invasively hooking and/or otherwise engaging cardiac tissue, such as leaflet tissue associated with a diseased heart valve (not separately shown), thereby at least partially anchoring the positioning element 2100 with respect to such valve. For example, the hook 2108 may include a shank portion 2110 at least partially defined by the intermediate region 2106 of the positioning element 2100, and a bend portion 2112 and a barb portion 2114 defined by the distal end region 2104 thereof. A free end 2116 of the barb portion 2114 may be sufficiently sharp and/or pointed to permit the barb portion 2114 to pierce the tissue of a heart valve leaflet. For example, the barb portion 2114 and the free end 2116 thereof may be sized, shaped, oriented, and/or configured to extend upward from the left ventricular side at least partially against the direction of blood flow through the native heart valve, and to permit the barb portion 2114 to pierce, connect with, and/or anchor with one or more of the heart valve leaflets.

The barb portion 2114 of the hook 2108 may take any suitable shape, including but not limited to the shape illustrated in FIG. 21, including wherein the barb portion 2114 is provided in the form of an upturned fork including a pair of tines 2118, each of which terminates in a point 2120. In accordance with embodiments of the present invention, each of the points 2120 of the tines 2118 is positionable against the tissue of a heart valve leaflet, and is of sufficient sharpness such that a moderate amount of upwardly directed force applied to the barb portion 2114 (e.g., from the shank portion 2110 and/or via the bend portion 2112, such as in the event of an upward pull by the surgeon on the positioning element 2100 during the implantation of a prosthesis of which the positioning element 2100 forms a part) can cause the tines 2118 to pierce the heart valve leaflet, and to plunge into the tissue thereof.

In accordance with embodiments of the present invention, the barb portion 2114 of the hook 2108 may further define a web region 2122 disposed between the tines 2118 and defining a curved surface 2124. The curved surface 2124 may be defined by a relatively large radius as compared to those which define the points 2120 of the tines 2118. In turn, the points 2120 may define a height dimension 2126 of the tines 2118 relative to a lowermost point 2128 on the web surface 2124. In such circumstances, the tines 2118 of the barb portion 2114 may be permitted to plunge into the tissue of a heart valve leaflet at least to a depth substantially equivalent to the height dimension 2126. Also, or alternatively, the radius associated with the web surface 2124 may be large enough, and/or the edges of the web surface 2124 may be sufficiently dull or otherwise rounded, to prevent further tearing or cutting into the tissue of a heart valve leaflet. In other words, the web surface 2124 may be of an appropriate size, shape and/or configuration to establish, in the form of the height dimension 2126, a practical limit in terms of a depth to which the tines 2118 will be allowed to plunge into the tissue of a heart valve upon exposure to ordinary manipulation and urging forces associated with heart valve prosthesis implantation.

While the barb portion 2114 of the hook 2108 is shown in FIG. 21 and described above to include wherein the barb portion 2114 is provided in the form of an upturned fork including a pair of tines 2118, each of which terminates in a point 2120, other configurations for the barb portion 2114 are possible. For example, such other configuration may include, but not necessarily be limited to: upturned forks for the barb portion including more than two tines; an upturned, non-forked, tissue-piercing element/spear/barb for the barb portion and provided with an alternatively-configured feature for limiting tissue piercing depth (e.g, in the form of a surrounding 'hilt' or an appropriate flange or other surface); an upturned, non-forked, tissue-piercing element/spear/barb for the barb portion and provided without a separate feature for limiting tissue piercing depth, etc.).

The proximal end region 2102 of the positioning element 2100 may define a hook 2130 for invasively hooking and/or otherwise engaging cardiac tissue, such as annulus tissue associated with a diseased heart valve (not separately shown), thereby at least partially anchoring the positioning element 2100 with respect to such valve. For example, the hook 2130 may include a bend portion 2132 and a barb portion 2134 defined by the proximal end region 2102 of the positioning element 2100. A free end 2136 of the barb portion 2134 may be sufficiently sharp and/or pointed to permit the barb portion 2134 to pierce the tissue of a heart valve annulus For example, the barb portion 2134 and the free end 2126 thereof may be sized, shaped, oriented, and/or configured to extend upward at least partially against the direction of blood flow through the native heart valve, and to permit the barb portion 2134 to pierce, connect with, and/or anchor with the heart valve annulus from the left ventricular side (e.g., from below a plane of the heart valve annulus).

The barb portion 2134 of the hook 2130 may take any suitable shape, including but not limited to the shape illustrated in FIG. 21, including wherein the barb portion 2114 is provided in the form of an upturned fork including a pair of tines 2138, each of which terminates in a point 2140. In accordance with embodiments of the present invention, each of the points 2140 of the tines 2138 is positionable against the annulus of a heart valve, and is of sufficient sharpness such that a moderate amount of upwardly directed force applied to the barb portion 2134 (e.g., via the bend portion 2132, such as in the event of an upward pull by the surgeon on the positioning element 2100 during the implantation of a prosthesis of which the positioning element 2100 forms a part) can cause the tines 2138 to pierce the heart valve leaflet, and to plunge into the tissue thereof.

In accordance with embodiments of the present invention, the barb portion 2134 of the hook 2130 may further define a web region 2142 disposed between the tines 2138 and defining a curved surface 2144. The curved surface 2144 may be defined by a relatively large radius as compared to those which define the points 2140 of the tines 2138. In turn, the points 2140 may define a height dimension 2146 of the tines 2138 relative to a lowermost point 2148 on the web surface 2144. In such circumstances, the tines 2138 of the barb portion 2134 may be permitted to plunge into the tissue of a heart valve leaflet at least to a depth substantially equivalent to the height dimension 2146. Also, or alternatively, the radius associated with the web surface 2144 may be large enough, and/or the edges of the web surface 2144 may be sufficiently dull or otherwise rounded, to prevent further tearing or cutting into the tissue of a heart valve leaflet. In other words, the web surface 2144 may be of an appropriate size, shape and/or configuration to establish, e.g., in the form of the height dimension 2146, a practical limit in terms of a depth to which the tines 2138 will be allowed to plunge into the tissue of a heart valve upon exposure to ordinary manipulation and urging forces associated with heart valve prosthesis implantation.

While the barb portion 2134 of the hook 2130 is shown in FIG. 21 and described above to include wherein the barb portion 2134 is provided in the form of an upturned fork including a pair of tines 2138, each of which terminates in a point 2140, other configurations for the barb portion 2134 are possible. For example, such other configuration may include, but are not necessarily limited to: upturned forks for the barb portion including more than two tines; an upturned, non-forked, tissue-piercing element/spear/barb for the barb portion and provided with an alternatively-configured feature for limiting tissue piercing depth (e.g, in the form of a surrounding 'hilt' or an appropriate flange or other surface); and an upturned, non-forked, tissue-piercing element/spear/barb for the barb portion and provided without a separate feature for limiting tissue piercing depth, etc.

The intermediate region 2106 disposed between the proximal and distal end regions 2102, 2104 may include an outward-facing side or surface 2148 defining a plurality of outwardly and downwardly extending barbs 2150, each of which terminates in a point 2152. In accordance with embodiments of the present invention, each of the points 2152 of the barbs 2150 may define a chevron associated with a correspondingly angled peak, be positionable against the tissue of a heart valve leaflet, and be of sufficient sharpness such that a moderate amount of downwardly directed force applied to the intermediate region 2106 (e.g., such as in the event of a downward push by the surgeon on the positioning element 2100 during the implantation of a prosthesis of which the positioning element 2100 forms a part) can cause the barbs 2150 to pierce corresponding adjacent portions of the heart valve annulus and/or leaflet, and to plunge into the tissue thereof In accordance with embodiments of the present invention, the outward-facing side or surface 2148 may further define apertures or through holes 2154 (e.g., of a size and shape roughly corresponding to those of the barbs 2150, as might result from the particular manner of forming the barbs 2150). In such circumstances, the apertures or through holes 2154 may be sized and/or shaped to encourage post-implantation ingrowth of heart tissue associated with the valve leaflet to which the positioning element 2100 is otherwise affixed or anchored as described herein.

While the intermediate region 2106 is shown in FIG. 21 and described above to describe barbs 2150 terminating in points 2152 define chevrons associated with a correspondingly angled peaks, other configurations for the points 2152 and/or for the barbs 2150 are possible. Also, and/or in the alternative, the intermediate region 2106 may include other or different elements than barbs for piercing the tissue of the heart valve leaflets. For example, such other configuration may include, but not necessarily be limited to, the intermediate region 2106 defining: downturned forks including two or more tines; and a downturned tissue-piercing element/spear/barb and provided with a depth-limitation feature other than (or in addition to) the outward-facing side or surface 2148 (e.g, in the form of a surrounding 'hilt' or other appropriate flange or surface), etc.

Still referring to FIG. 21, each of the proximal and distal end regions 2102, 2104 of the positioning element 2100 may include an aperture 2156, each of which may be sized and shaped to accommodate a filament or cord (e.g., a cord or cable having a diameter of 0.008 inches, ±0.002") being threaded through the positioning element 2100. The structure and particular function of the apertures 2156 are described in greater detail below with respect to a manner in which a heart valve prosthesis incorporating the positioning element 2100 may be remotely manipulated and implanted with respect to a diseased heart valve.

Turning now to FIGS. 22, 23, 24 and 25, an exemplary heart valve prosthesis 2200 including a set of three of the above-described positioning elements 2100 is schematically depicted. In accordance with exemplary embodiments of the present disclosure, the heart valve prosthesis 2200 may be a modified version of the heart valve prosthesis 102 shown and described above with respect to FIG. 1. For example, the present disclosure comprehends embodiments of the heart valve prosthesis 2200 featuring both similarities to, and differences from, the heart valve prosthesis 102.

As alluded to above, some features, aspects, and functions of the heart valve prosthesis 2200 may be substantially similar to corresponding features, aspects, and functions of the heart valve prosthesis 102. At least some other features, aspects, and functions of the heart valve prosthesis 2200, though at least somewhat different from corresponding features, aspects, and functions of the heart valve prosthesis 102, may still be considered analogous thereto. Accordingly, to the extent the above description of the various features, aspects, and functions of the heart valve prosthesis 102 is not inconsistent with the following description of the heart valve prosthesis 2200, the former is hereby incorporated within the latter.

Figure 22:
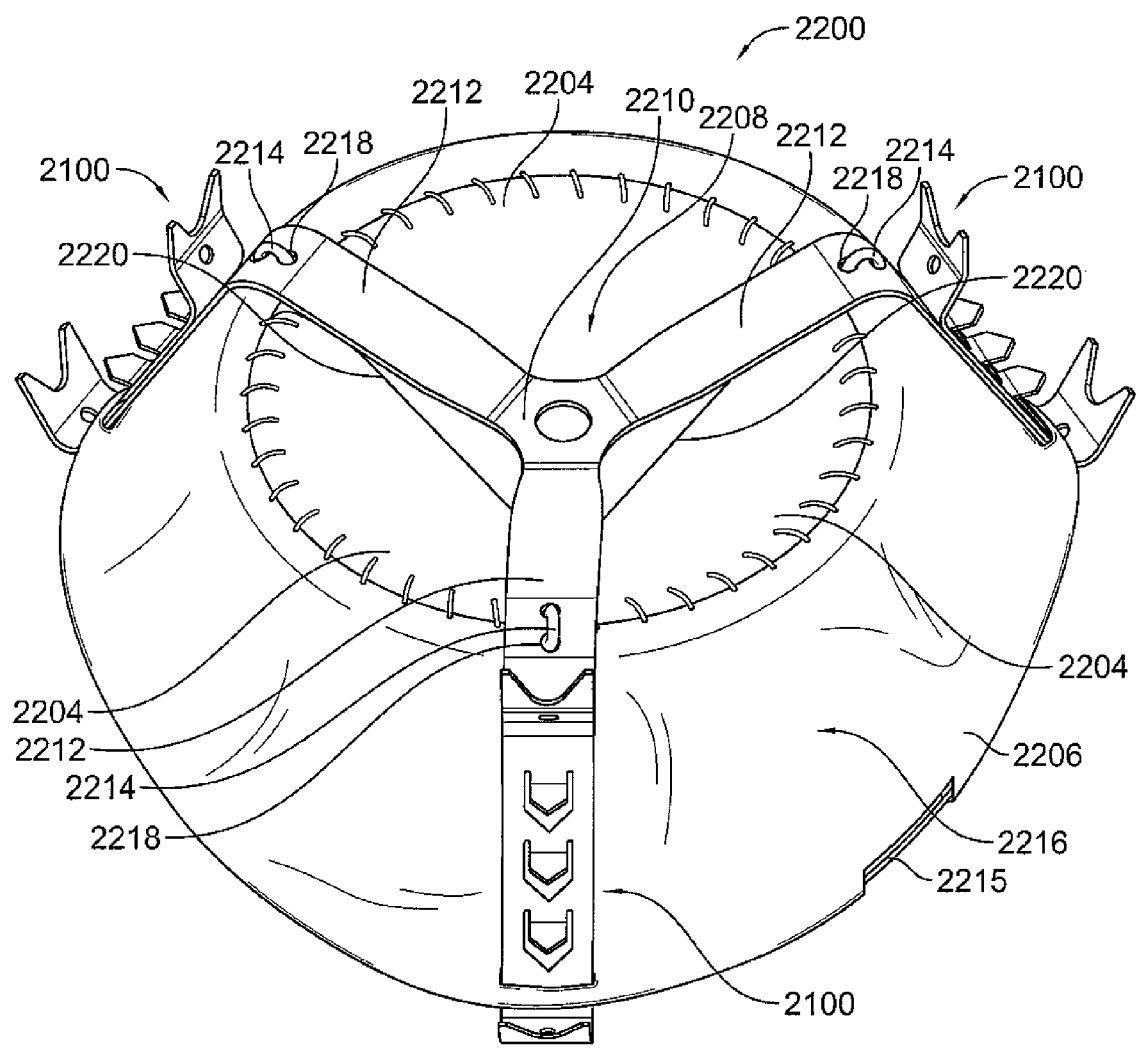
FIG. 22 is a schematic perspective view of a valve prosthesis incorporating the positioning element of FIG. 21.
Figure 23:
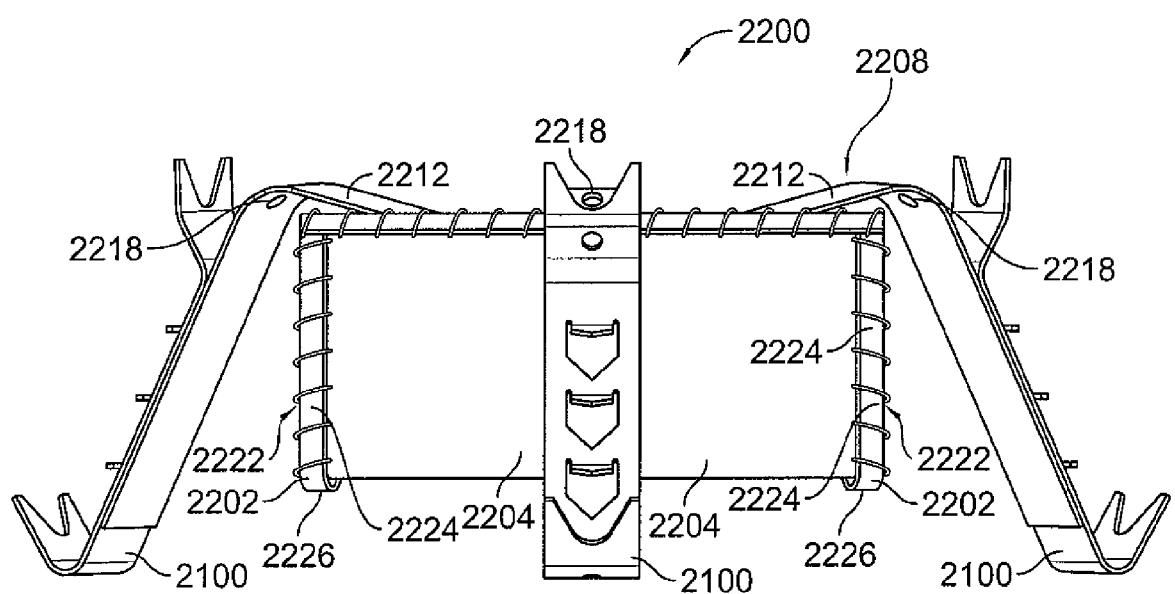
FIG. 23 is a side elevational view of the valve prosthesis of FIG. 22.
Figure 24:
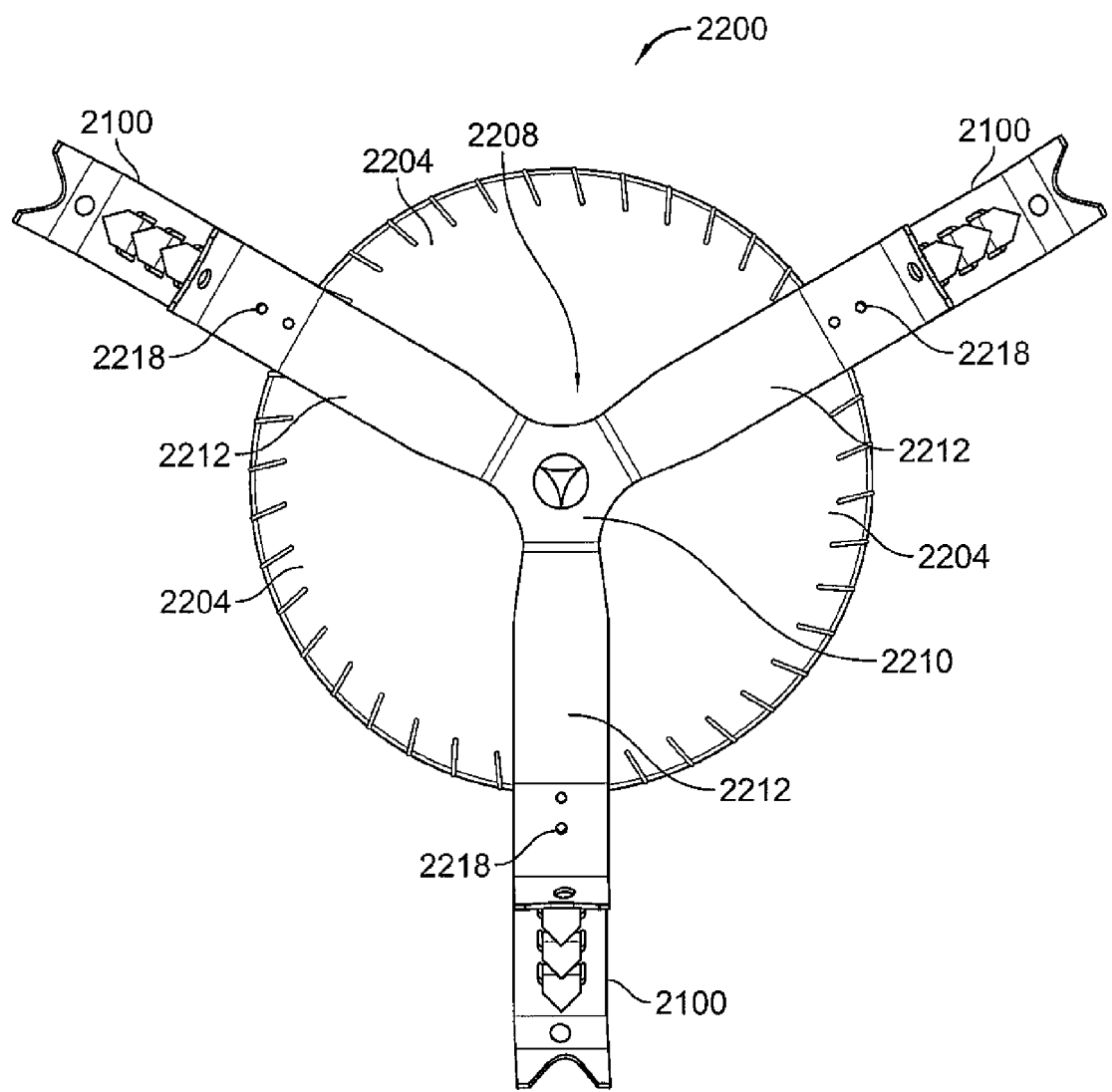
FIG. 24 is a top plan view of the valve prosthesis of FIG. 22.
Figure 25:
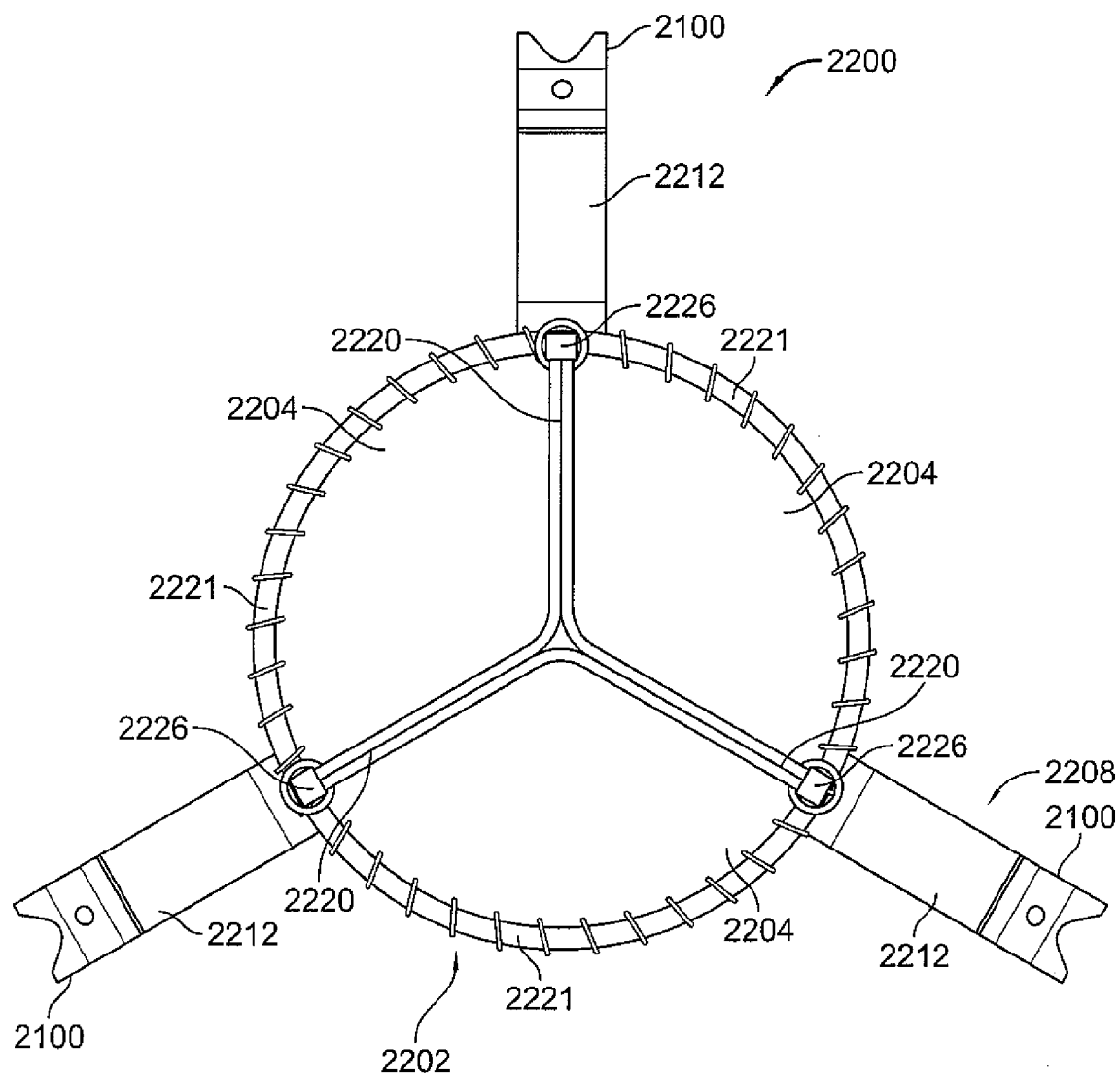
FIG. 25 is a bottom plan view of the valve prosthesis of FIG. 22.

The heart valve prosthesis 2200 may include a flexible ring 2202 (e.g., a resilient ring). Mounted with respect to the flexible ring 2202 may be a plurality (e.g., three (3)) of leaflet membranes 2204, a skirt 2206, and a resilient element 2208 (for purposes of convenience and to facilitate discussion of other components of the heart valve prosthesis 2200, the skirt 2206 shown in FIG. 22 is omitted from each of FIGS. 23, 24 and 25). The resilient element 2208 may include a hub 2210 and a plurality (e.g., three (3)) of legs 2212, each of the legs 2212 extending from the hub 2210 (e.g., in a regular radial arrangement, spaced by about 120° relative to each other) and being movably mounted with respect to the flexible ring 2202 via individual ones of a corresponding plurality (e.g., three (3)) of mounting elements 2214.

Each of the flexible ring 2202 and the resilient element 2208 may be fabricated from a metallic material. For example, the flexible ring 2202 and the resilient element 2208 may be fabricated from a shape memory alloy (SMA, also known as a smart alloy, memory metal, or muscle wire) such as the nickel-titanium alloy Nitinol. The valve prosthesis 2200 may further include a corresponding plurality (e.g., three (3)) of instances of the above-described positioning element 2100, each positioning element 2100 being attached to one of the legs 2212 of the resilient element 2208.

As shown in the exemplary embodiment of FIGS. 22, 23, 24 and 25, each of the leaflet membranes 2204 may assume an inwardly-bowed orientation when mounted with respect to the flexible ring 2202. More or fewer of the leaflet membranes 2204 may be employed without departing from the spirit or scope of the present disclosure, provided the desired blood flow functionality is achieved. The leaflet membranes 2204 may be fabricated from xenograft tissue and/or from synthetic membrane materials and may be secured to the flexible ring 2202 through conventional means (e.g., via sutures) such that each of the plurality of leaflet membranes 2204 extends downwardly with respect to the flexible ring 2202. Alternatively, or in addition, the leaflet membranes 2204 may comprise bovine pericardium tissue optimized for size and rapid closure function.

The skirt 2206 may be configured and dimensioned to control for perivlvular leakage (i.e., a reverse-flow of blood about the periphery of the heart valve prosthesis 2200). For example, the skirt 2206 may be generously sized for purposes of accommodating irregular valve openings in such a manner as to normalize them for implantation of the heart valve prosthesis 2200 to minimize any leakage at the device/annulus interface. As shown in FIG. 22, the skirt 2206 may extend to a full extent of the flexible ring 2202, e.g., around the entire circumference of the flexible ring 2202. The skirt 2206 may be formed from a single, contiguous structure, or may be defined by a plurality of adjacent and/or overlapping elements that, together, extend along the circumference of the flexible ring 2202, including (but not necessarily limited to) examples in which the skirt 2206 departs from the substantially circular shape thereof depicted in FIG. 22. For instance, some such examples of the skirt 2206 (not shown) may include wherein an outer peripheral edge of the skirt 2206 between the radial stations of the legs 2212 bows radially outward and/or downward, thereby approximating, to at least some extent, the appearance of the leaves of a three-leaf clover. Some other such examples of the skirt 2206 may include wherein an outer peripheral edge of the skirt bows outward both at the radial stations of the legs 2212, and between the radial stations of the legs 2212, forming a total of six leaves or "lobes". According to exemplary embodiments of the present disclosure, and as particularly shown in FIG. 22, the skirt 2206 may be sutured with respect to the flexible ring 2202.

The skirt 2206 may be fabricated from a variety of materials that are suitably flexible and/or pliable materials, while also being compatible with heart valve tissue. For example, and in accordance with embodiments of the present disclosure, the material of the skirt 2206 may include or define features or characteristics such as to facilitate tissue ingrowth from the heart valve annulus or valve leaflets, and/or to permit the skirt 2206 to become embedded within the surrounding valve tissue, which may be useful in terms of scaling the valve prosthesis 2200 against a reverse flow of blood around its periphery in situ. For example, the skirt 2206 may be fabricated with two layers of polyester double velour and/or Dacron fabric cut to the designed shape with a fabricated cutting die. An inner diameter of the skirt 2206 may be sewn, e.g., with polyester thread, to the flexible ring 2202. A portion of the skirt 2206 may pass at least partially above the positioning elements 2100. For example, an outer diameter of the skirt 2206 may pass above the positioning elements 2100 below the lowermost barb 2150 (FIG. 21), and may be sewn (not shown) closed to capture a hoop 2215 of small diameter Nitinol wire to provide radial force against the native valve surface. One or more integral radial Nitinol wires may further be incorporated as part of the skirt 2206 and secured to the resilient element 2208 to provide support to and eliminate the skirt 2206 from 'flipping' or buckling. Portions of the skirt 2206 may be sewn or otherwise affixed to the positioning elements 2100. Additionally, and/or in the alternative, the skirt 2206 may be omitted and replaced with a radially-extending bumper (not shown) fabricated from a foam or foam-like material, such as an open cell, articulating urethane or PTFE foam or polyester felt in appropriate thickness and/or density.

As shown in FIGS. 22, 23, 24 and 25, each leg 2212 of the resilient element 2208 may be configured to exhibit, and/or adapted to assume, an arcuate shape or bend in the vicinity of an upper margin of the flexible ring 2202. The mounting elements 2214 may be of any suitable shape, design, configuration, and/or attachment technique relative to the skirt 2206 and/or relative to the legs 2212 to permit rotational and/or overturning motion of the legs 2212 relative to one or more of, or relative to each of, the skirt 2206, the flexible ring 2202, and the hub 2210. For example, the mounting elements 2214 may be substantially C-shaped, and/or donut shaped. Each of the mounting elements 2214 may, for example, be coupled (e.g., fixedly joined) to the skirt 2206 adjacent an upper surface 2216 thereof, and may pass through a pair of corresponding apertures 2218 formed in each leg 2212. (As an alternative, the mounting elements 2214 may be integrally formed as part of the skirt 2206.) The skirt 2206 may be tacked, adhered, or otherwise joined to the underside of one or more of the legs 2212, and/or to one or more of the positioning elements 2100, where the same are positioned above the skirt 2206.

Each of the positioning elements 2100 may be coupled (e.g., fixedly joined) to a corresponding leg 2212 of the resilient element 2208, e.g., through a weld between an inner surface of the positioning element 2100 and a corresponding outer surface of the leg 2212. The positioning elements 2100 may be dimensioned such that the proximal ends thereof extend above an upper margin of the flexible ring 2202 (e.g., when the valve prosthesis 2200 assumes the orientation depicted in FIGS. 22, 23, 24 and 25). The proximal and distal ends of the positioning elements 2100 may be spaced by a distance that facilitates positioning of the valve prosthesis 2200 relative to a heart valve annulus (e.g., relative to a mitral valve annulus), as described in greater detail below. For example, the proximal and distal ends of the positioning elements 2100 may be space by between about seven (7) millimeters and about twenty-five (25) millimeters. As discussed above, the positioning elements 2100 and the legs 2212 may be fabricated from a material that permits at least some degree of flexibility/deformation (e.g., elastic deformation), such as stainless steel or Nitinol of an appropriate thickness/gauge. Other materials for the positioning elements 2100 and/or the legs 2212 are possible.

Each individual subassembly of a leg 2212 and a positioning element 2100 may be substantially vertically aligned with and/or disposed directly above a respective one of a plurality (e.g., three (3)) of commissures 2220 formed between adjacent ones of the plurality of leaflet membranes 2204. (In other words, none of the subassemblies of a leg 2212 and a positioning element 2100 is necessarily either substantially or at least partially vertically aligned above any particular one of the plurality of leaflet membranes 2204.). In such circumstances, the leaflet membranes 2204 may occupy and/or function within the peripheral space between the radial stations of the legs 2212 and the positioning elements 2100, as opposed to the peripheral space beneath such structure. Such an arrangement may be advantageous for at least the following reason(s): promoting uniform blood flow about the legs 2212, preventing the leaflet membranes 2204 from contacting the legs 2212, and permitting the positioning elements 2100 and the legs 2212 to engage native tissue independent of leaflet membrane movement.

The flexible ring 2202 may be a variation of the above-discussed flexible ring 106 of FIG. 1, and/or may share some features of the above-discussed flexible ring 1300 illustrated in FIGS. 13 and 14. The flexible ring 2202 may be resilient in that it may tend (e.g., absent any substantial compressive forces) to expand outward to assume a three-dimensional shape (e.g., the three-dimensional shape shown in FIG. 22), in which the flexible ring 2202 may have a non insubstantial vertical height, in addition to a characteristic lateral width or diameter. More particularly, and referring particularly to FIGS. 23 and 25, the flexible ring 2202 may include multiple instances of a hoop segment 2221. The hoop segments 2221 may be contained within a common horizontal plane (e.g., upon the flexible ring 2202 being expanded out to its maximum width and height) wherein the hoop segments 2221 may be separated by and/or coupled via a corresponding number of instances of a retainer 2222 extending vertically and/or substantially perpendicularly relative to the common horizontal plane, constituting at least a portion of the height extent of the flexible ring 2202 and comprising first and second arms 2224 joined by a distal bend 2226. The retainers 2222 may function to receive and retain at least a peripheral portion of the commissures between the leaflet membranes 2204. Each individual hoop segment 2221 may be associated with a corresponding one of the plurality of leaflet membranes 2204, in that each of the leaflet membranes may be coupled (e.g., sutured) to the flexible ring substantially solely along a corresponding one of the individual hoop segments 2221. In turn, each retainer 2222 may be associated with an interface between adjacent ones of the plurality of leaflet membranes 2204. In such circumstances, wherever corresponding outer peripheral edges of an adjacent pair of the leaflet membranes 2204 meet, the same are bound up and/or sealed along their entire height between the arms 2224 of a corresponding retainer 2222 (e.g., from the common horizontal plane defined by the hoop segments 2221 down to the distal bend 2226).

Turning now to FIGS. 26A, 26B, 26C, 26D, 26E, 26F and 26G, an exemplary sequence of steps for percutaneously delivering and positioning the above-discussed valve prosthesis 2200 in a desired anatomical location is schematically depicted. In accordance with exemplary embodiments of the present disclosure, the sequence of steps shown in FIGS. 26A-26G may be a modified version of the sequence of steps for percutaneously delivering and positioning the heart valve prosthesis 102 shown and described above with respect to FIGS. 4A-4I. For example, the present disclosure comprehends embodiments of the sequence of steps for percutaneously delivering and positioning the above-discussed valve prosthesis 2200 featuring both similarities to, and differences from, the sequence of steps for percutaneously delivering and positioning the heart valve prosthesis 102 shown and described above with respect to FIGS. 4A-4I.

As alluded to above, some features and aspects of the sequence of steps shown in FIGS. 26A-26G may be substantially similar to the sequence of steps shown and described above with respect to FIGS. 4A-4I. At least some other features and aspects of the sequence of steps shown in FIGS. 26A-26G, though at least somewhat different from corresponding features and aspects of the sequence of steps shown and described above with respect to FIGS. 4A-4I, may still be considered analogous thereto. Accordingly, to the extent the above description of the sequence of steps shown in FIGS. 4A-4I is not inconsistent with the following description of the sequence of steps shown in FIGS. 26A-26G, the former is hereby incorporated within the latter.

Figure 26A:
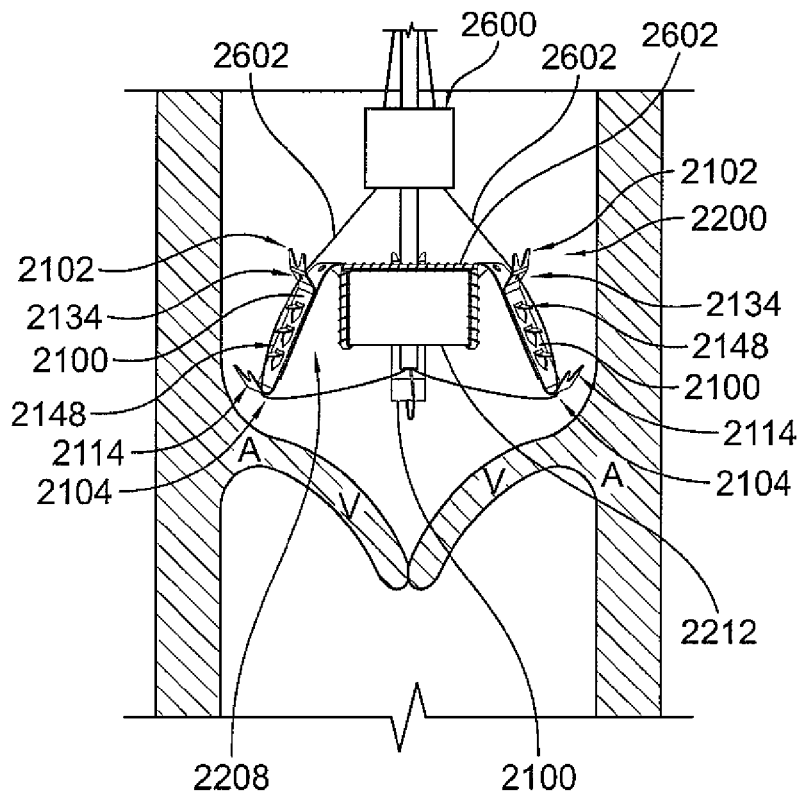
FIGS. 26A, 26B, 26C, 26D, 26E, 26F and 26G are schematic side views illustrating percutaneous placement of the heart valve prosthesis of FIGS. 22-25 relative to an annulus according to exemplary embodiments of the present disclosure.

As shown in FIGS. 26A, upon the valve prosthesis 2200 exiting, for example, the distal end of a catheter (not shown) at the desired anatomical location (e.g., adjacent a mitral valve), resilient properties of several components of the valve prosthesis 2200, particularly the flexible ring 2202 and the legs 2212 of the resilient element 2208, may cause the flexible ring 2202 to automatically assume a non-deformed/uncompressed shape, and to cause the positioning elements 2100 to become overturned or inverted by rotating both outwardly and downwardly past the horizontal. In such non-deformed/uncompressed shape, the outer surfaces 2148 of the positioning elements 2100 may face generally outward, and the barbed portions 2134, 2114 of the proximal and distal end regions 2102, 2104 extend generally outwardly and/or upwardly.

Figure 26B:
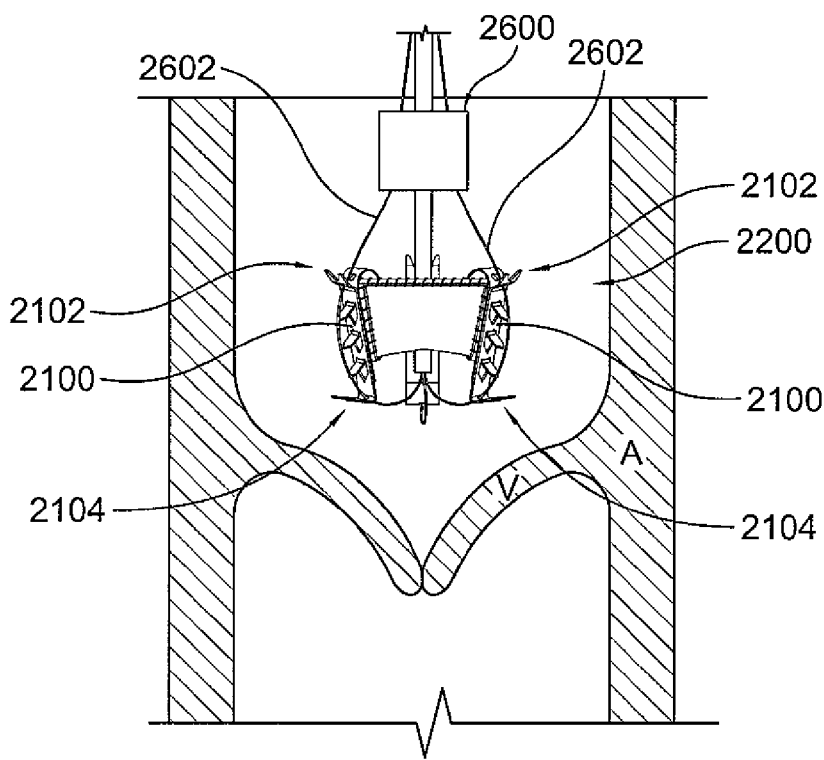
Figure 26C:
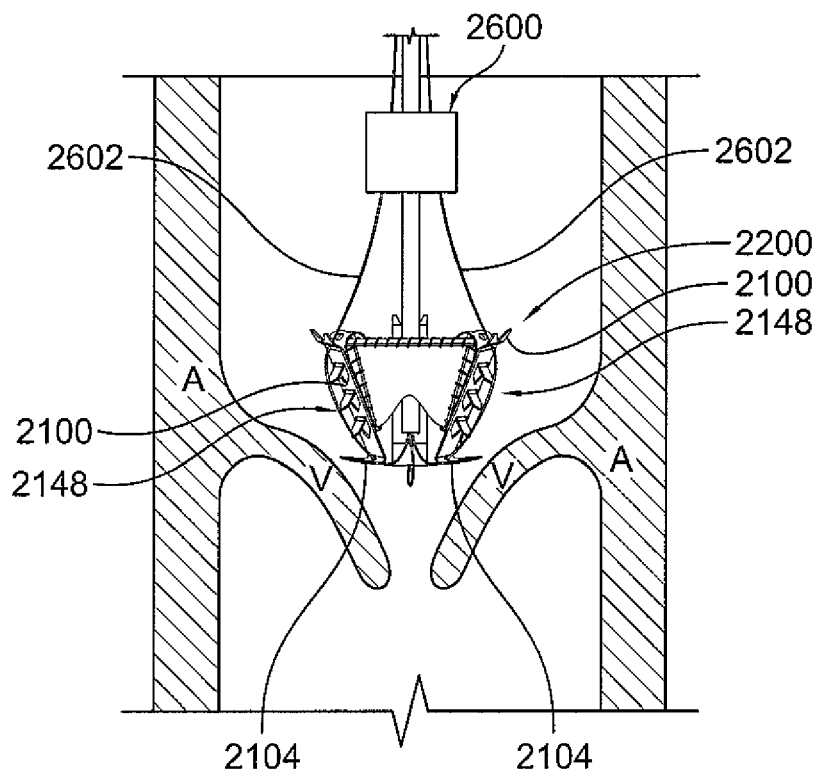
Figure 26D:
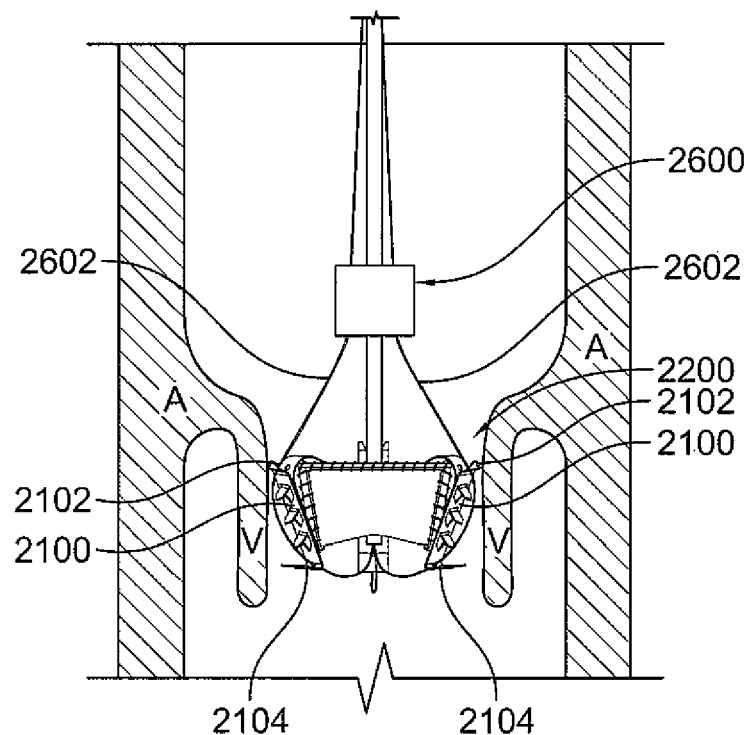

From the orientation of the valve prosthesis 2200, and more particularly, of the positioning elements 2100 thereof, shown in FIG. 26A, the surgeon/clinician may employ a prosthesis positioning apparatus 2600 to deflect both the distal 2104 and proximal 2102 end regions of the positioning elements 2100 inward, thereby generally radially compressing the valve prosthesis 2200, as shown in FIG. 26B. More particularly, the surgeon may pull upward very snugly on respective lengths of three separate instances of a cord 2602 (e.g., a metallic cable, such as a Nitinol cable, having a diameter of 0.008", ±0.002") to pull all of the positioning elements 2100 radially inward in the manner of a cinching movement, after which the barbed portions of the proximal and distal end regions of the positioning elements 2100 are still observed to extend generally outwardly and/or upwardly. The valve prosthesis 2200 may then be remotely lowered by the surgeon/clinician down into the mitral valve as shown in FIGS. 26C and 26D, in which step the surgeon/clinician may use employ the radially-compressed distal end regions 2104 of the positioning elements 2100 in the manner of a 'plow' to push the valve leaflets V to some extent radially outwardly (e.g., to accommodate the insertion of the valve prosthesis 2200 within the diseased valve), and by which step the surgeon/clinician may place the proximal end regions 2102 of the positioning elements 2100 at a general elevation of the annulus A in preparation for further implantation steps.

Figure 26E:
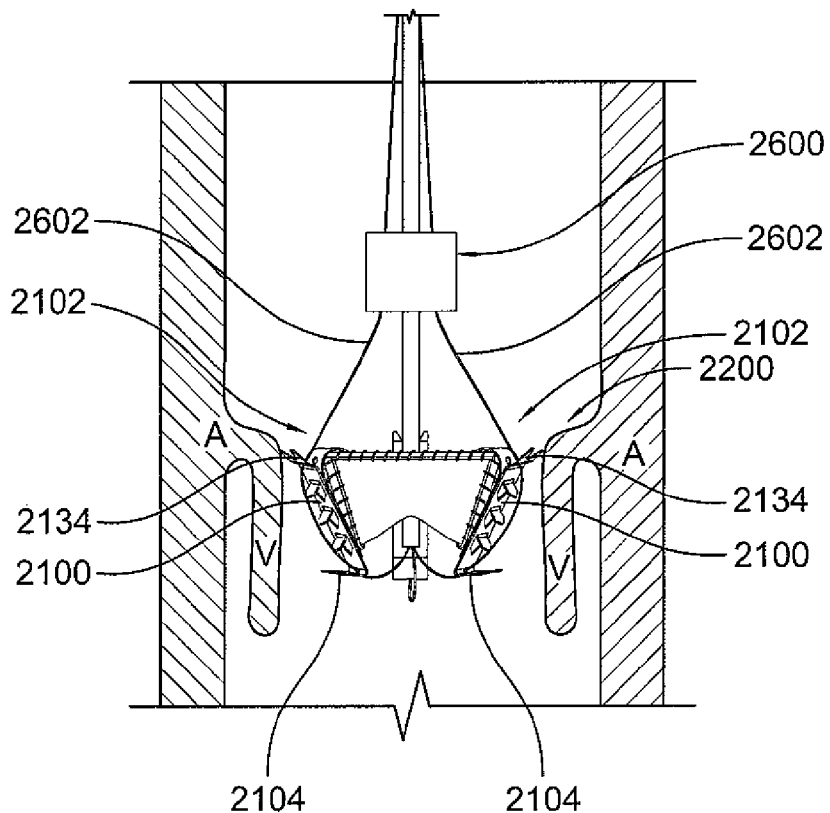
Figure 26F:
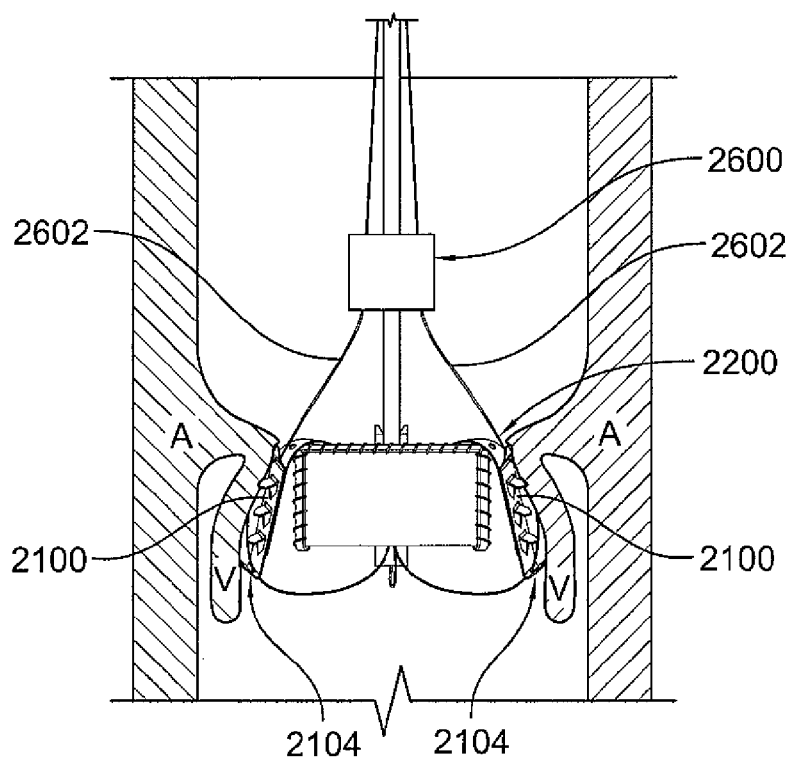
Figure 26G:
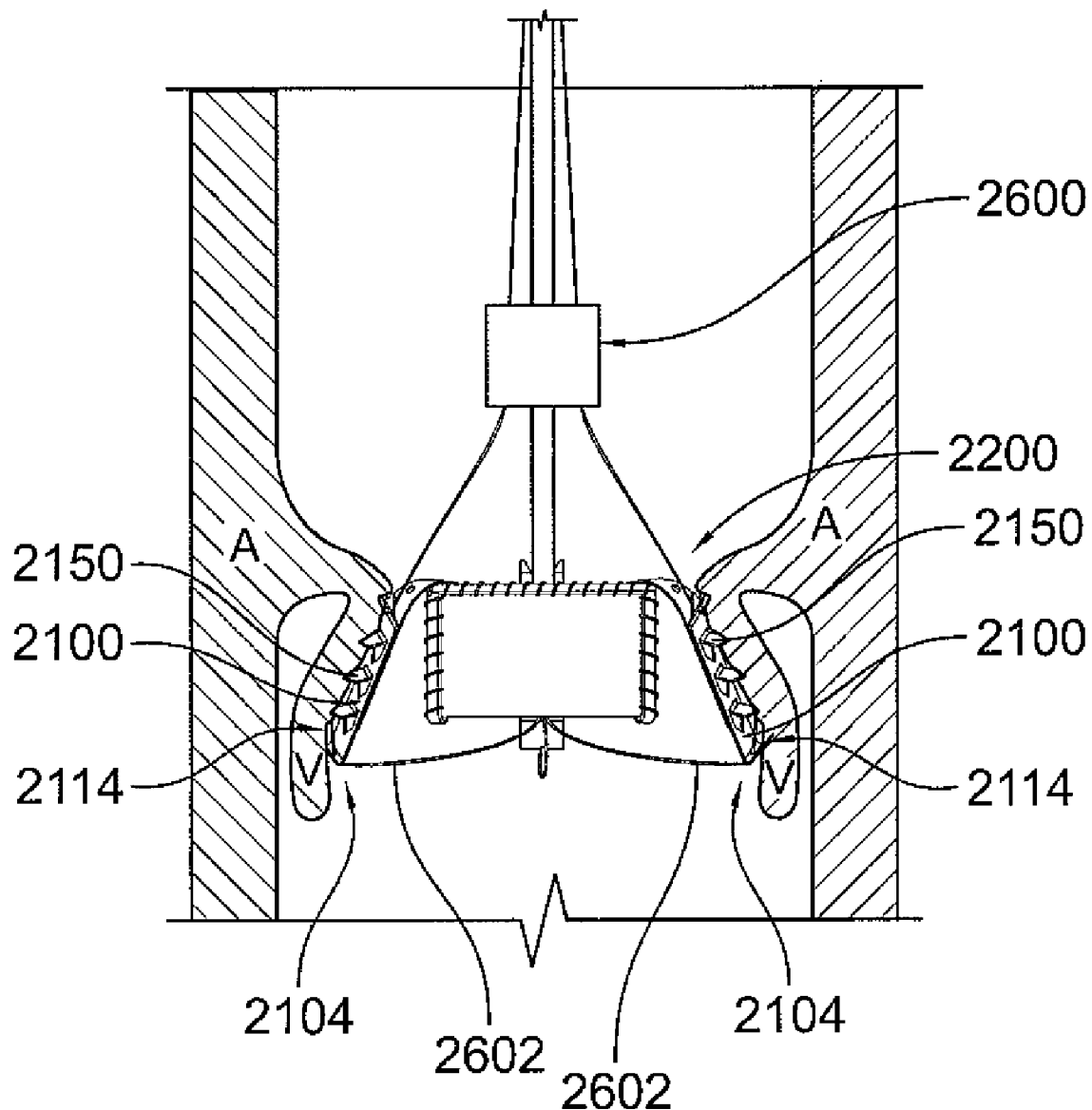

The surgeon/clinician may then carefully begin to release tension on the cords 2602 as shown in FIG. 26E in such a way as to permit the proximal end regions 2102 of the positioning elements 2100 to extend and expand radially outwardly against corresponding tissue of the annulus A, while still largely preventing the distal end regions 2104 thereof to extend or expand away from each other (e.g., causing the distal end regions of the positioning elements to remain more or less cinched together as compared to the proximal end regions thereof), after which the surgeon/clinician may then execute a short upward pull on the valve prosthesis 2200 to cause the barbed portions of the proximal end regions of the positioning elements to pierce, connect, anchor with, and/or become lodged within the ventricular side (e.g., the left ventricular side) of the tissue of the annulus A. Turning now to FIG. 26F, the surgeon/clinician may now release the remaining tension on the cords 2602 to permit the distal end regions 2104 of the positioning elements 2100 to extend or expand outward to sweep the valve leaflets V further radially outwardly). Turning now to FIG. 26G, the surgeon/clinician may then execute another short upward pull on the valve prosthesis 2200, thereby causing the barbed portions 2114 of the distal end regions 2104 of the positioning elements 2100 to pierce, connect, anchor with, and/or become lodged within the tissue of the valve leaflets V. In the process of tensioning and relaxing the cords 2602 to execute the second of the two above-described upward pulls on the valve prosthesis 2200, and/or to execute any further upward pulls thereof that may be desired or be deemed necessary, the surgeon/clinician may further cause the downward-extending barbs 2150 of the intermediate region to pierce and/or become lodged within the ventricular side tissue of the annulus A and/or the of valve leaflets V. In this manner, the valve prosthesis 2200 employs differently-directed tissue-piercing elements to become very securely lodged in place and/or affixed with respect to the annulus A and valve leaflets V of the diseased mitral valve. Among other advantages, this effectively ensures that the valve prosthesis 2200 will not move vertically to any functionally significant extent from the desired location with respect to the diseased valve once the implantation process has been completed in accordance with the present disclosure.

Figure 27:
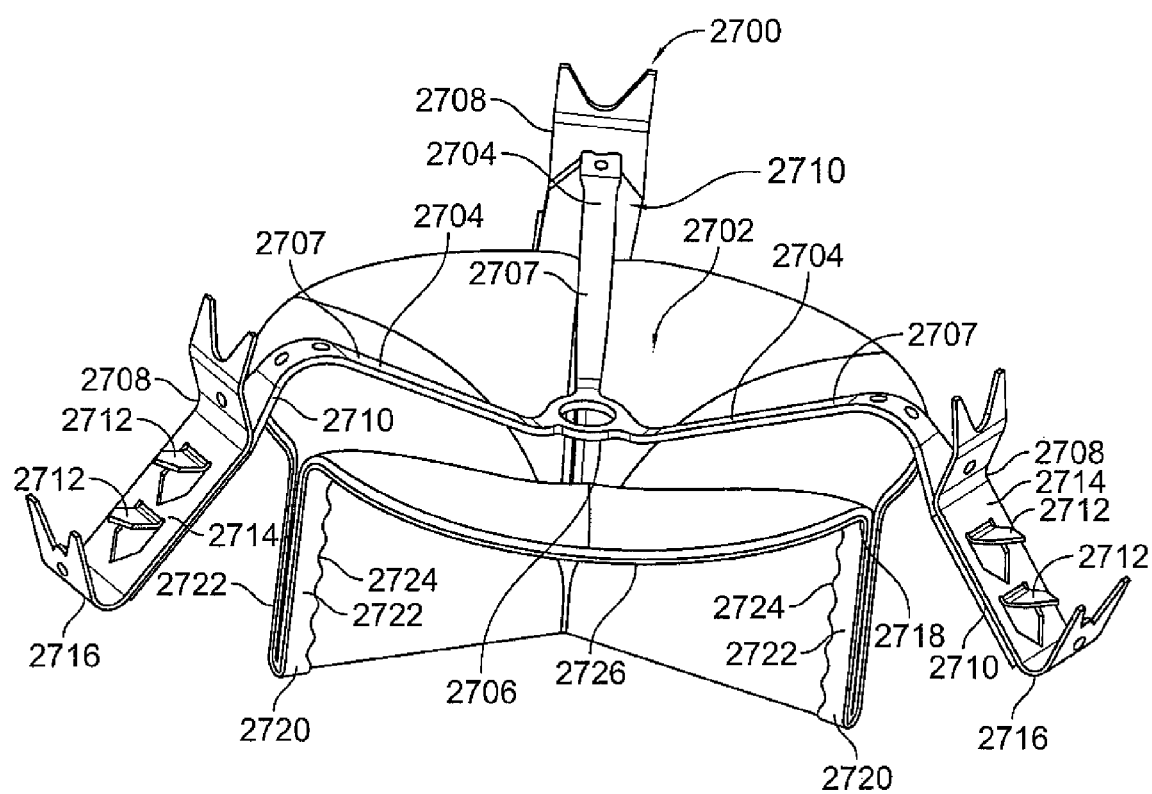
FIG. 27 is a schematic perspective view of a variation of the valve prosthesis of FIG. 22 according to exemplary embodiments of the present disclosure.

Turning now to FIG. 27, another exemplary heart valve prosthesis 2700 including a set of three of the above-described positioning elements 2100 is shown. In accordance with exemplary embodiments of the present disclosure, the heart valve prosthesis 2700 may be a variation of the heart valve prosthesis 2200 shown and described above with respect to FIGS. 22-25. More particularly, the heart valve prosthesis 2700 includes a resilient element 2702 substantially similar to the resilient element 2208 of the heart valve prosthesis 2200, at least except as discussed below. The resilient element 2702 may include legs 2704 and a hub 2706 exhibiting relatively narrowed profiles as compared to at least some embodiments of the legs 2212 and the hub 2210 of the heart valve prosthesis 2200 for purposes of reducing the area of the resilient element 2702 (e.g., down to about 0.095 square inches or less). Advantages provided by such a reduced profile may include reduced interference with blood flow through the heart valve prosthesis 2700, and reduced potential that the leaflets of the heart valve prosthesis 2700 will contact and/or become abraded by the legs 2704. For example, a first elongate region 2707 of each legs 2704 that extends outward from the hub 2706 (e.g., forming an angle of between about 45° and about 85° from the central axis, such as an angle of approximately 64° therefrom) may exhibit up to a one-third or greater reduction in breadth as compared to the legs 2212 of the heart valve prosthesis 2200. For another example, the hub 2706 may exhibit up to a one-third or greater reduction in breadth as compared to the hub 2210 of the heart valve prosthesis 2200. Alternatively, and/or in addition, the legs 2706 may be partially or substantially completely replaced with struts or wires (not shown) (e.g., a pair of two closely-spaced wires extending in parallel and exhibiting the same or similar hoop strength as the legs 2706 and/or the legs 2212).

The resilient element 2702 may further include positioning elements 2708 exhibiting an abbreviated overall length as compared to one or more embodiments of the positioning elements 2100 of the heart valve prosthesis 2200, thereby affording a relatively shorter and/or more slender profile without any degradation in fixation. Advantages provided by such a reduced length in the positioning elements 2708 may include allowing complete unfolding of the heart valve prosthesis 2700 adjacent a diseased native heart valve (e.g., within the left atrium), facilitating the advancement of same within in the atrium (e.g., in the left atrium) during introduction of the heart valve prosthesis 2700 into the heart valve annulus, and facilitating orientation and reorientation of the heart valve prosthesis 2700 with respect to the heart valve annulus after such introduction. (A second elongate region 2710 of each leg 2704 that extends outward from the first elongate region 2707 thereof (e.g., forming an included angle of between about 85° and about 125°, such as an included angle of approximately 104°), may exhibit a somewhat larger breadth dimension than the first elongate region 2707 to facilitate attachment (e.g., via welding) of the positioning elements 2708 to the legs 2704.) Instead of three barbs, the positioning elements 2708 may feature two barbs 2712. The barbs 2712 may, for example, be spaced approximately ⅛ inch apart along a surface 2714 of the positioning element 2708, pointing generally downward (e.g., away from the atrium and toward the ventriclular cavity) and outward at an angle of between about 50° and about 70° with respect to the surface 2714, such as an angle of approximately 60° with respect thereto. A lower, distal end 2716 of each positioning element 2708 may be curved into a 120 degree sweep. Cable guide holes (not shown) may also be formed in the barbs 2712.

The heart valve prosthesis 2700 further includes a flexible ring 2718 substantially similar to the flexible ring 2202 of the heart valve prosthesis 2200, at least except as discussed below. The flexible ring 2718 may include regularly spaced (e.g., by 120°) retainers 2720 defining arms 2722 for receiving leaflet commissures, wherein detents 2724 (e.g., 'scallops' useful as sewing detents) are formed in the arms 2722. As a whole, and in accordance with embodiments of the present disclosure, the retainers 2720 may positioned in rotational alignment with the legs 2704 and the positioning elements 2708. Alternatively (not shown), the retainers 2720 may be positioned out of phase therewith (e.g., 60° out of phase), a configuration which in at least some instances facilitates a process of folding and/or collapsing the overall frame structure of the heart valve prosthesis 2700. The flexible ring 2718 may further include hoop segments 2726 extending between the retainers 2720.

Turning now to FIGS. 28A, 28B, 28C, 28D, 28E, and 28F, an exemplary sequence of steps for percutaneously delivering and positioning the above-discussed valve prosthesis 2200 in a desired anatomical location is schematically depicted. In accordance with exemplary embodiments of the present disclosure, the sequence of steps shown in FIGS. 28A-26F may be a variation of the sequence of steps for percutaneously delivering and positioning the heart valve prosthesis 2200 shown and described above with respect to FIGS. 26A-26G. A system and associated method for remotely manipulating the resilient element 2208 (FIG. 22), positioning elements 2100, and the skirt 2206 of the heart valve prosthesis 2200 of FIGS. 22 is depicted in a series of schematic views illustrating the heart valve prosthesis 2200 from a vantage point below the distal ends 2104 of the positioning elements 2100 (e.g., as the heart valve prosthesis might appear if viewed from the ventricular cavity during implantation with respect to a diseased heart valve).

Figure 28A:
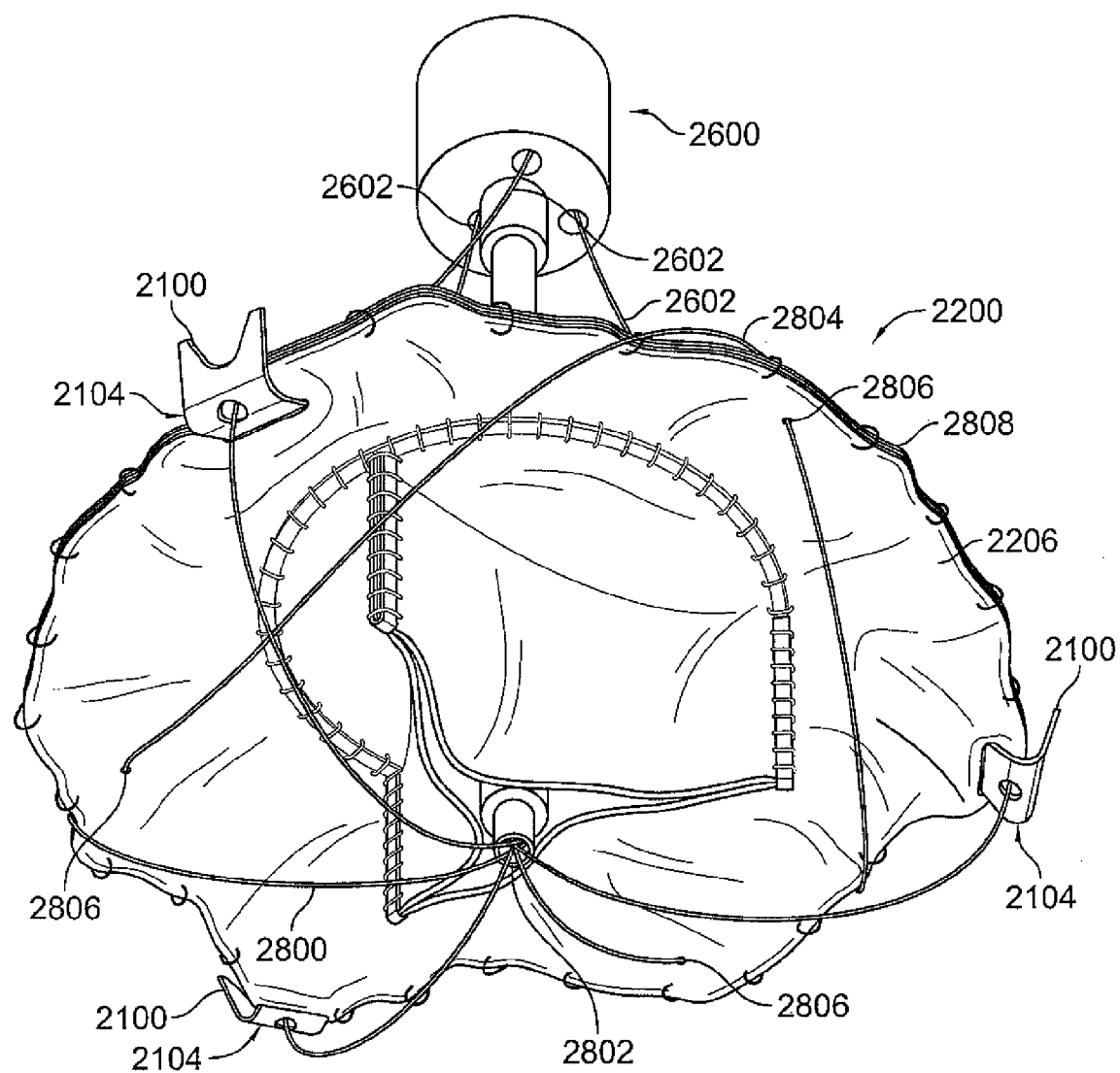
FIGS. 28A, 28B, 28C, 28D, 28E and 28F are schematic perspective views illustrating a system and method of remotely manipulating the positions and orientations various components of the heart valve prosthesis of FIGS. 22-25 in accordance with exemplary embodiments of the present disclosure.

As shown in FIGS. 28A, which corresponds at least in part to FIG. 26A and the description thereof provided above, in addition to the three separate instances of a cord 2602 for manipulating the resilient element 2208 (FIG. 22) and the positioning elements 2100, the prosthesis positioning apparatus 2600 may include a separate cord 2800 extending outward from a distal end of a cord distribution tube 2802 to form a loop 2804 for manipulating the skirt 2206. For example, the skirt 2206 may include a plurality of perforations 2806 provided along a outer peripheral edge 2808 of the skirt 2206 through which the loop 2804 of cord 2800 may be threaded.

Figure 28B:
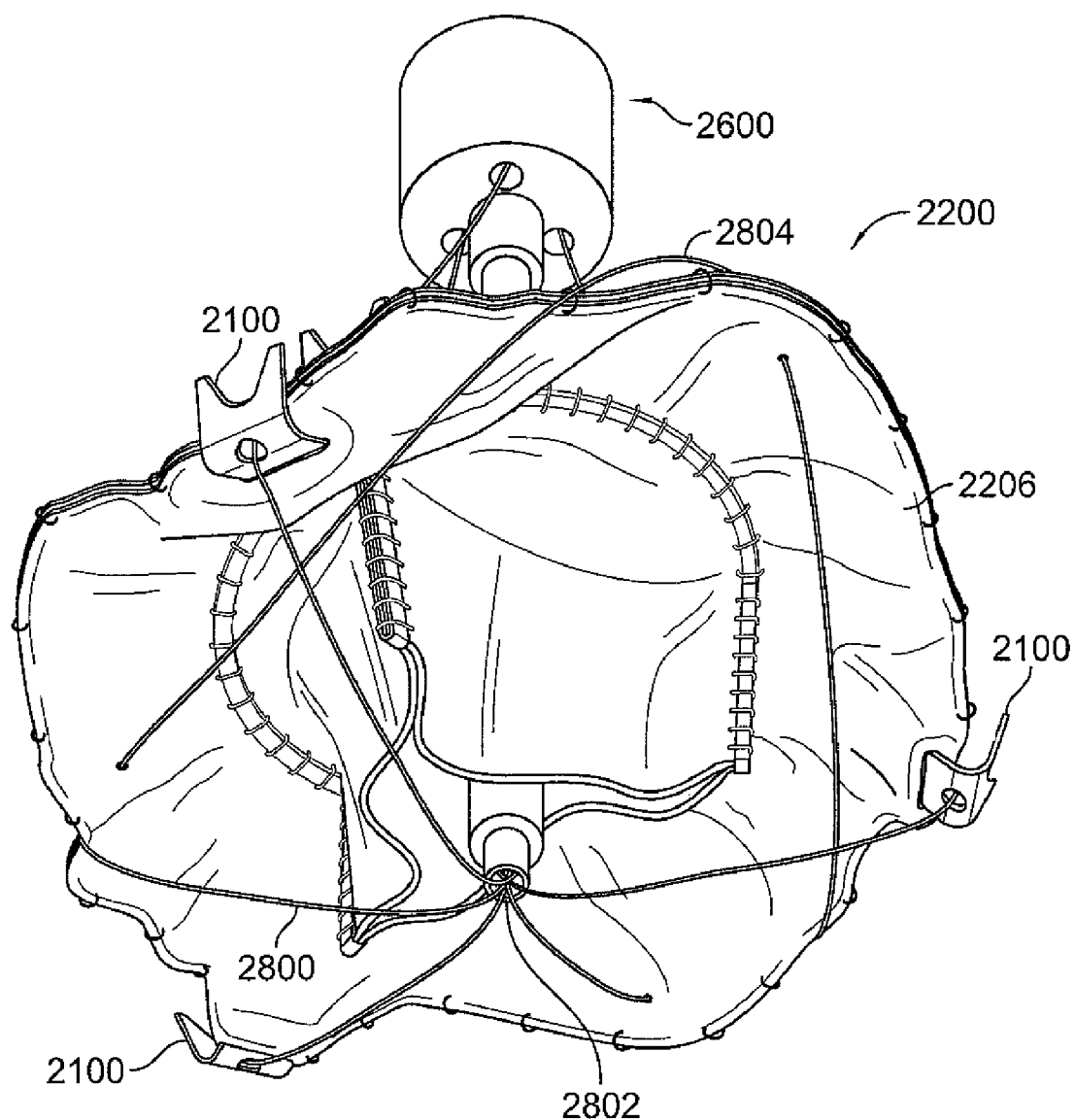
Figure 28C:
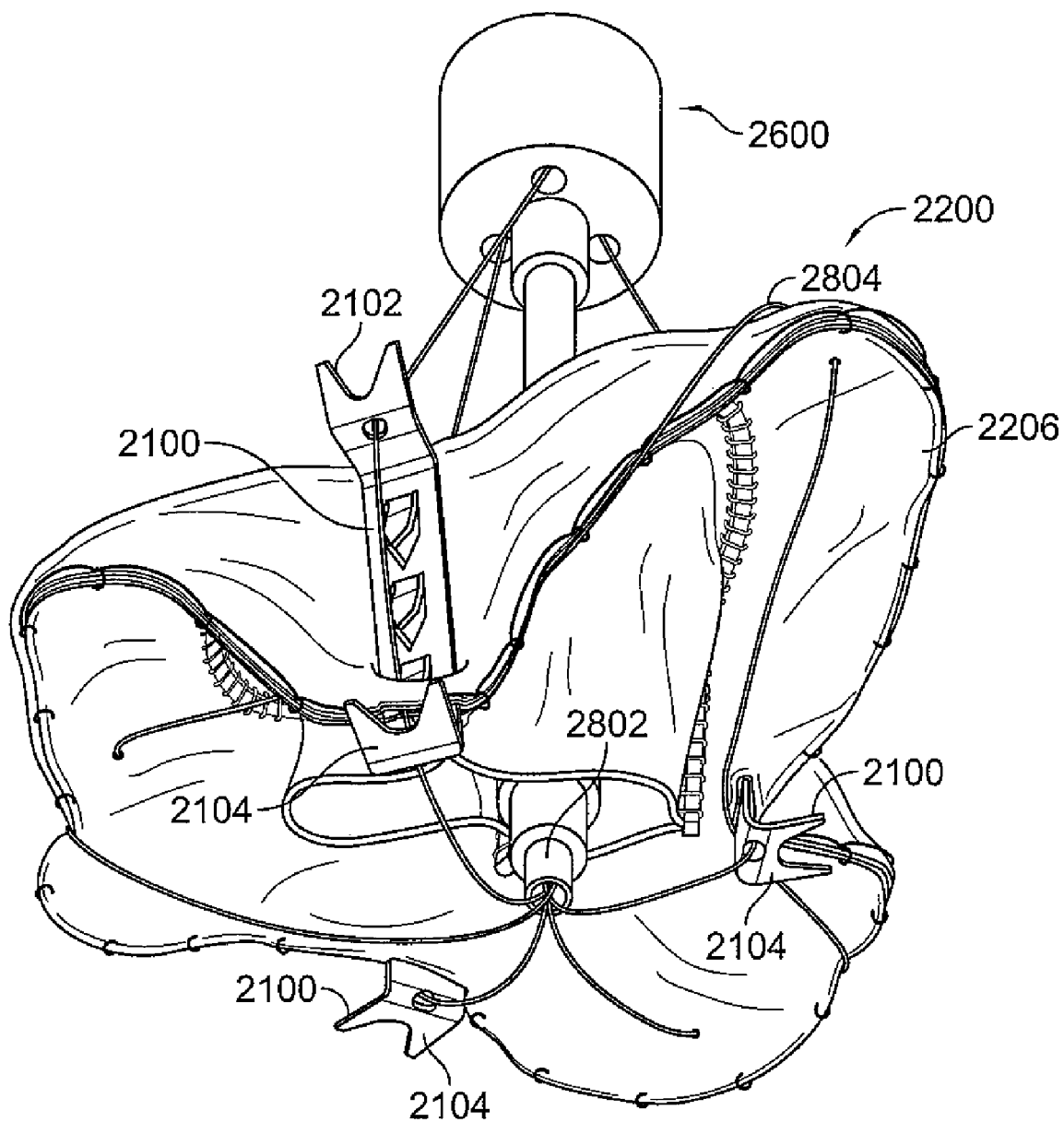
Figure 28D:
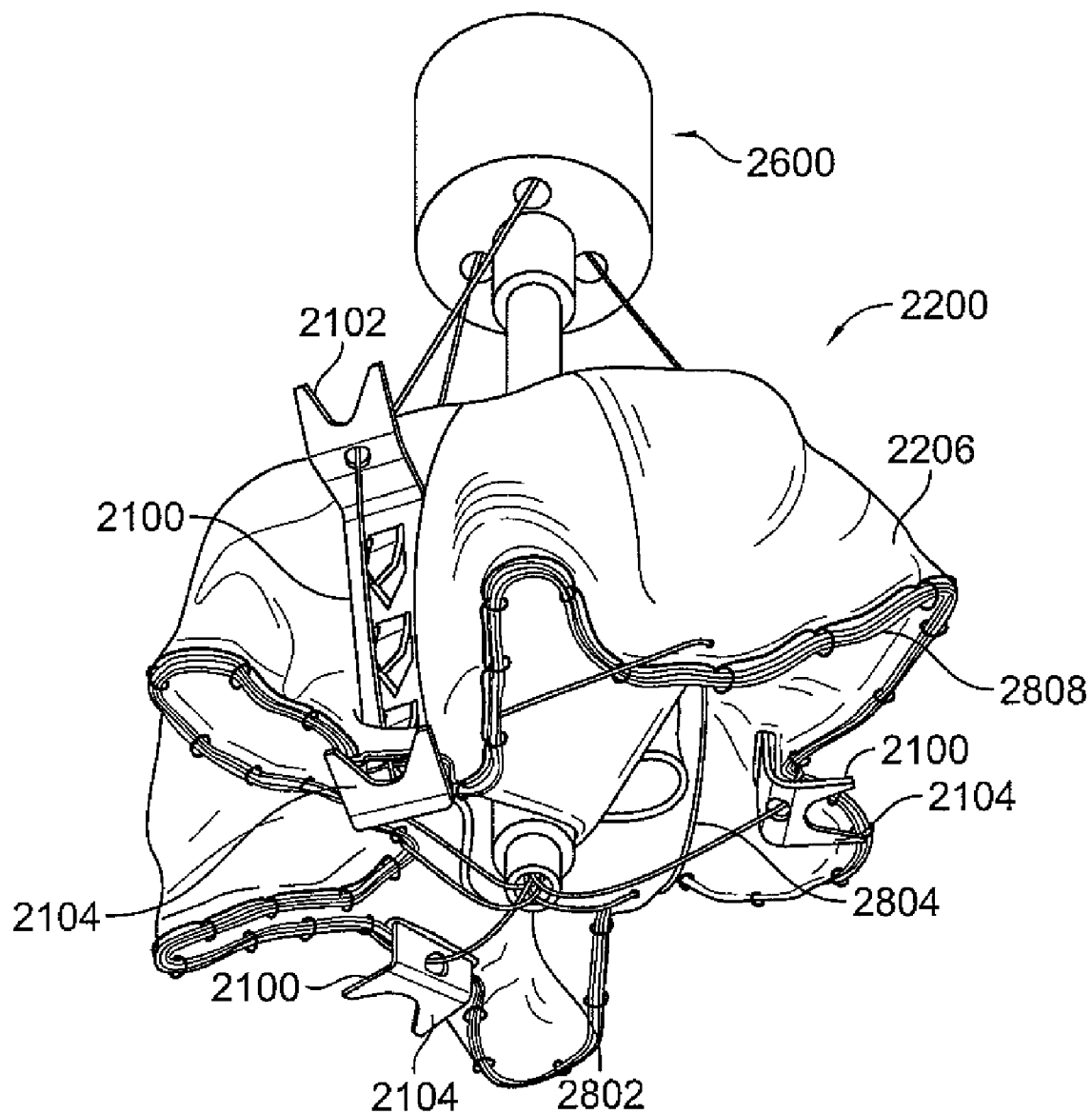

From the orientation of the valve prosthesis 2200, and more particularly, of the positioning elements 2100 thereof, shown in FIG. 28A, the surgeon/clinician may employ the prosthesis positioning apparatus 2600 to deflect both the distal 2104 and proximal 2102 (FIG. 21) end regions of the positioning elements 2100 inward, thereby generally radially compressing the valve prosthesis 2200, as shown in sequence in FIGS. 28B, 28C, and 28D. At the same time, the surgeon may pull upward very snugly on respective lengths of the cord 2800 (e.g., a metallic cable, such as a Nitinol cable, having a diameter of 0.008", ±0.002") to pull the peripheral edge 2808 of the skirt radially inward in the manner of a cinching movement. The valve prosthesis 2200 may then be remotely lowered by the surgeon/clinician down into the mitral valve (see FIGS. 26C and 26D) whereby the surgeon/clinician may place the proximal end regions 2102 of the positioning elements 2100 at a general elevation of the annulus A (see FIG. 26D) in preparation for further implantation steps.

Figure 28E:
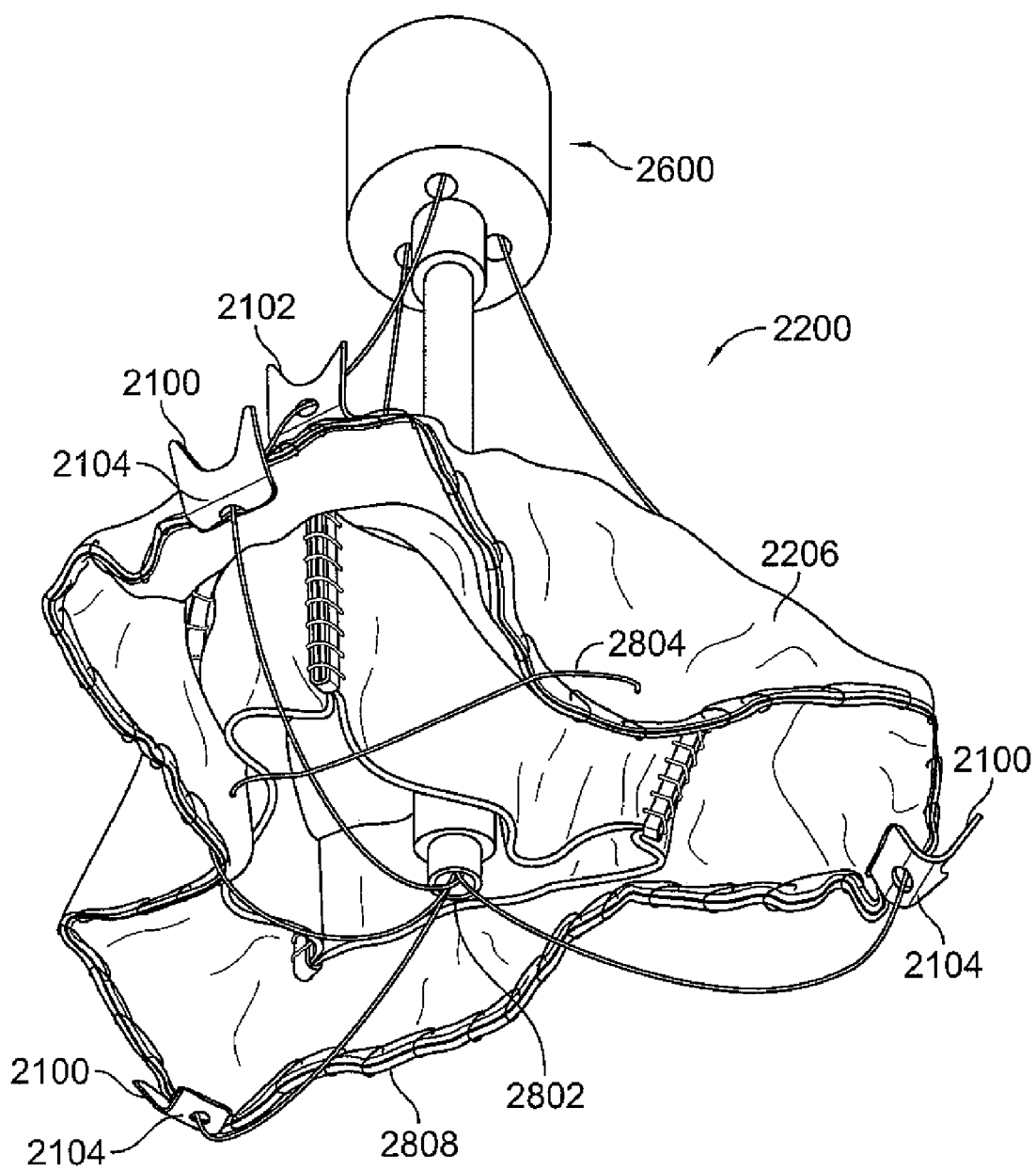
Figure 28F:
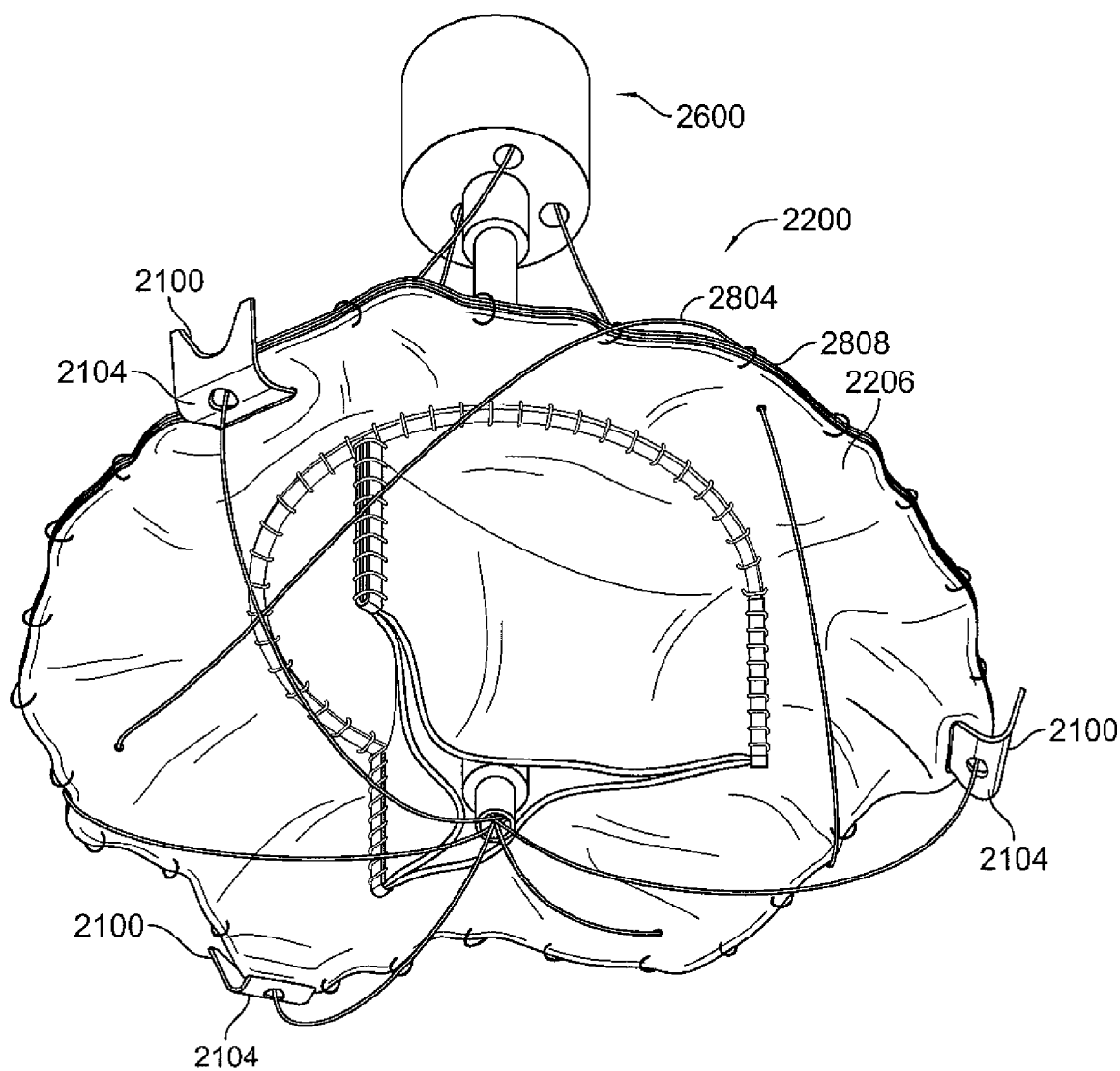

The surgeon/clinician may then carefully begin to release tension on the cords 2602 as shown in FIG. 28E in such a way as to permit the proximal, and then the distal end regions 2102, 2104 of the positioning elements 2100, along with the barbs 2150 thereof to extend outward, engage, and pierce corresponding tissue (e.g., left ventricular side tissue) of the annulus A and/or of the valve leaflets V (see FIGS. 26E, 26F, and 26G). Turning now to FIG. 28F, the surgeon/clinician may now release the tension on the cord 2800 to permit the peripheral edge 2808 of the skirt 2206 to extend or expand outward under the force of the one or more resilient elements (e.g., the hoop 2215 (FIG. 22) of small diameter Nitinol wire) embedded within it. In this manner, the valve prosthesis 2200 may be effectively sealed against a reverse flow of blood around its periphery in situ.

Although implementations of the invention have been described in detail above, those skilled in the art will readily appreciate that many additional modifications are possible without materially departing from the novel teachings and advantages of the invention. Any such modifications are intended to be included within the scope of the invention as defined in the following claims.

The invention claimed is:

1. A valve prosthesis, comprising:
   a. a resilient ring;
   b. a plurality of leaflet membranes mounted with respect to the resilient ring; and
   c. a plurality of positioning elements movably mounted with respect to the resilient ring, each of the positioning elements defining a proximal tissue engaging region including a first elongate tissue-piercing element, a distal tissue engaging region spaced apart from the proximal tissue engaging region along a direction of blood flow through the valve prosthesis and including a second elongate tissue-piercing element, and an intermediate tissue engaging region disposed between the proximal and distal tissue engaging region and including a third elongate tissue-piercing element;
   wherein the proximal, distal, and intermediate tissue-engaging regions are cooperatively configured and dimensioned to simultaneously engage separate corresponding areas of the tissue of an anatomical structure so as to stabilize a position of the valve prosthesis with respect to the anatomical structure, including wherein for purposes of so simultaneously engaging the separate corresponding areas of tissue, at least one of the first, second, and third elongate tissue-piercing elements is pointed at least partially opposite the direction of blood flow, and at least another thereof is pointed at least partially along the direction of blood flow; and
   wherein at least one of the proximal and distal tissue engaging regions further defines an arcuate surface for engaging the corresponding area of tissue so as to limit a depth to which the respective first or third elongate tissue-piercing element may become lodged therewithin.

2. The valve prosthesis according to claim 1, wherein at least one of the first and third elongate tissue-engaging elements is a fork tine.

3. The valve prosthesis according to claim 1, wherein the second elongate tissue-piercing element is chevron-shaped barb.

4. The valve prosthesis according to claim 1, wherein for purposes of so simultaneously engaging the separate corresponding areas of tissue, the first elongate tissue-piercing element is pointed at least partially opposite the direction of blood flow, and the second elongate tissue-piercing element is pointed at least partially along the direction of blood flow.

5. The valve prosthesis according to claim 1, wherein for purposes of so simultaneously engaging the separate corresponding areas of tissue, the third elongate tissue-piercing element is pointed at least partially opposite the direction of blood flow, and the second elongate tissue-piercing element is pointed at least partially along the direction of blood flow.

6. The valve prosthesis according to claim 1, wherein for purposes of so simultaneously engaging the separate corresponding areas of tissue, two of the first, second, and third elongate tissue-piercing elements are pointed at least partially opposite the direction of blood flow, and the other thereof is pointed at least partially along the direction of blood flow.

7. The valve prosthesis according to claim 1, wherein each of the plurality of positioning elements is adapted to substantially completely invert by rotating relative to the resilient ring between a first position in which the at least two of the first, second, and third elongate tissue-piercing elements point at least partially along the direction of blood flow for facilitating positioning of the valve prosthesis within a delivery catheter, and a second position in which the at least two of the first, second, and third elongate tissue-piercing elements point at least partially opposite the direction of blood flow for engaging tissue.

8. The valve prosthesis according to claim 1, wherein the resilient ring includes multiple instances of a hoop segment defining a hoop plane and separated by a corresponding number of instances of gap within the hoop plane.

9. The valve prosthesis according to claim 1, wherein the resilient ring includes multiple instances of a hoop segment defining a hoop plane for coupling with a separate respective one of the plurality of leaflet membrane and a corresponding number of instances of a retainer for forming a separate respective interface between respective adjacent ones of the plurality of leaflet membranes.

10. The valve prosthesis according to claim 1, wherein the resilient ring defines a circular or elliptical peripheral geometry.

11. The valve prosthesis according to claim 1, wherein the resilient ring is adapted to be implanted with respect to a diseased heart valve such that the first tissue-piercing element lodges within tissue associated with an annulus of the diseased heart valve, and the second tissue-piercing element lodges within tissue associated with a leaflet of the diseased heart valve.

12. The valve prosthesis according to claim 1, further comprising a skirt mounted with respect to the resilient ring for at least partially sealing against a reverse flow of blood around a periphery of the valve prosthesis.

13. A valve prosthesis comprising:
   a. a resilient ring;
   b. a plurality of leaflet membranes mounted with respect to the resilient ring; and
   c. a plurality of positioning elements movably mounted with respect to the resilient ring, each of the positioning elements defining a proximal tissue engaging region including a first elongate tissue-piercing element, a distal tissue engaging region spaced apart from the proximal tissue engaging region along a direction of blood flow through the valve prosthesis and including a second elongate tissue-piercing element, and an intermediate tissue engaging region disposed between the proximal and distal tissue engaging region and including a third elongate tissue-piercing element;
   wherein the proximal, distal, and intermediate tissue-engaging regions are cooperatively configured and dimensioned to simultaneously engage separate corresponding areas of the tissue of an anatomical structure so as to stabilize a position of the valve prosthesis with respect to the anatomical structure, including wherein for purposes of so simultaneously engaging the separate corresponding areas of tissue, at least one of the first, second, and third elongate tissue-piercing elements is pointed at least partially opposite the direction of blood flow, and at least another thereof is pointed at least partially along the direction of blood flow;
   a hub disposed substantially centrally with respect to a peripheral geometry of the resilient ring, and
   a plurality of legs directed radially with respect to the resilient ring and mounted with respect to (i) the hub and (ii) a corresponding positioning element of the plurality thereof.

14. The valve prosthesis according to claim 13, wherein at least one leg of the plurality of legs is mounted with respect to the positioning element such that the positioning element is substantially rotationally fixed with respect to the leg.

15. The valve prosthesis according to claim 13, wherein at least one leg of the plurality of legs includes an intermediate joint and corresponding leg lengths extending from the joint for allowing the leg to collapse against itself for facilitating positioning of the valve prosthesis within a delivery catheter.

16. A valve prosthesis comprising:
   a. a resilient ring;
   b. a plurality of leaflet membranes mounted with respect to the resilient ring; and
   c. a plurality of positioning elements movably mounted with respect to the resilient ring, each of the positioning elements defining a proximal tissue engaging region including a first elongate tissue-piercing element, a distal tissue engaging region spaced apart from the proximal tissue engaging region along a direction of blood flow through the valve prosthesis and including a second elongate tissue-piercing element, and an intermediate tissue engaging region disposed between the proximal and distal tissue engaging region and including a third elongate tissue-piercing element;
   wherein the proximal, distal, and intermediate tissue-engaging regions are cooperatively configured and dimensioned to simultaneously engage separate corresponding areas of the tissue of an anatomical structure so as to stabilize a position of the valve prosthesis with respect to the anatomical structure, including wherein for purposes of so simultaneously engaging the separate corresponding areas of tissue, at least one of the first, second, and third elongate tissue-piercing elements is pointed at least partially opposite the direction of blood flow, and at least another thereof is pointed at least partially along the direction of blood flow; and
   wherein each positioning element of the plurality thereof includes a pair of apertures for permitting the positioning element to be releasably engaged by a corresponding filament looped through the apertures of the pair thereof for remotely controlling a rotational position of the positioning element during implantation of the valve prosthesis.

* * * * *